United States Patent
McCool et al.

(10) Patent No.: US 10,486,107 B2
(45) Date of Patent: Nov. 26, 2019

(54) REVERSE OSMOSIS MEMBRANES AND SEPARATIONS

(71) Applicants: ExxonMobil Research and Engineering Company, Annandale, NJ (US); Georgia Tech Research Corporation, Atlanta, GA (US)

(72) Inventors: Benjamin A. McCool, Annandale, NJ (US); Harry W. Deckman, Clinton, NJ (US); Ryan P. Lively, Atlanta, GA (US); Dong-Yeun Koh, Atlanta, GA (US); Randall D. Partridge, Califon, NJ (US)

(73) Assignees: ExxonMobil Research and Engineering Company, Annandale, NJ (US); Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 15/347,993

(22) Filed: Nov. 10, 2016

(65) Prior Publication Data

US 2017/0144106 A1 May 25, 2017

Related U.S. Application Data

(60) Provisional application No. 62/367,168, filed on Jul. 27, 2016, provisional application No. 62/367,175, filed on Jul. 27, 2016, provisional application No. 62/254,792, filed on Nov. 13, 2015.

(51) Int. Cl.
*B01D 69/08* (2006.01)
*B01D 61/02* (2006.01)
(Continued)

(52) U.S. Cl.
CPC ......... *B01D 61/025* (2013.01); *B01D 53/228* (2013.01); *B01D 61/002* (2013.01);
(Continued)

(58) Field of Classification Search
None
See application file for complete search history.

(56) References Cited

U.S. PATENT DOCUMENTS 4,510,047 A    4/1985   Thompson
4,571,444 A *   2/1986   Black .................. B01D 61/025
                                                  208/308
(Continued)

FOREIGN PATENT DOCUMENTS

EP         0428052 A2    11/1990
JP       2013094744 A2    5/2013

OTHER PUBLICATIONS

International Search Report and Written Opinion PCT/US2016/061263 dated Mar. 9, 2017.
(Continued)

*Primary Examiner* — Tam M Nguyen
(74) *Attorney, Agent, or Firm* — Edmonds & Cmaidalka, P.C.

(57) ABSTRACT

Asymmetric membrane structures are provided that are suitable for various types of separations, such as separations by reverse osmosis. Methods for making an asymmetric membrane structure are also provided. The membrane structure can include at least one polymer layer. Pyrolysis can be used to convert the polymer layer to a porous carbon structure with a higher ratio of carbon to hydrogen.

15 Claims, 21 Drawing Sheets

(51) Int. Cl.

| | | |
|---|---|---|
| *C07C 15/08* | (2006.01) | |
| *B01D 53/22* | (2006.01) | |
| *B01D 61/00* | (2006.01) | |
| *C07C 7/00* | (2006.01) | |
| *B01D 67/00* | (2006.01) | |
| *B01D 69/12* | (2006.01) | |
| *B01D 71/02* | (2006.01) | |
| *C07C 5/27* | (2006.01) | |
| *C07C 7/14* | (2006.01) | |
| *C07C 7/144* | (2006.01) | |
| *C02F 1/44* | (2006.01) | |
| *C02F 103/08* | (2006.01) | |

(52) U.S. Cl.
CPC ....... *B01D 61/007* (2013.01); *B01D 67/0067* (2013.01); *B01D 69/08* (2013.01); *B01D 69/12* (2013.01); *B01D 69/125* (2013.01); *B01D 71/021* (2013.01); *B01D 71/022* (2013.01); *C02F 1/441* (2013.01); *C07C 5/2732* (2013.01); *C07C 7/005* (2013.01); *C07C 7/14* (2013.01); *C07C 7/144* (2013.01); *C07C 15/08* (2013.01); *B01D 2323/30* (2013.01); *B01D 2325/022* (2013.01); *B01D 2325/04* (2013.01); *C02F 2103/08* (2013.01)

(56) References Cited

U.S. PATENT DOCUMENTS

| | | | |
|---|---|---|---|
| 4,685,940 A | 8/1987 | Soffer et al. | |
| 5,234,597 A * | 8/1993 | Welmers | B01D 61/025 210/634 |
| 5,470,482 A | 11/1995 | Holt | |
| 5,750,820 A | 5/1998 | Wei | |
| 5,972,079 A | 10/1999 | Foley et al. | |
| 6,376,733 B1 | 4/2002 | Ferraro et al. | |
| 7,581,589 B2 * | 9/2009 | Roes | C10G 1/002 166/267 |
| 7,638,674 B2 * | 12/2009 | Rice | C07C 5/277 585/738 |
| 8,083,813 B2 * | 12/2011 | Nair | E21B 36/04 44/300 |
| 8,471,087 B2 * | 6/2013 | Diaz | B01D 3/143 585/802 |
| 8,529,757 B2 | 9/2013 | Go et al. | |
| 8,697,929 B2 | 4/2014 | Ou et al. | |
| 9,010,547 B2 * | 4/2015 | Chu | B01D 67/0013 210/500.29 |
| 9,079,138 B2 * | 7/2015 | Nemser | B01D 61/027 |
| 9,248,413 B2 * | 2/2016 | Sano | B01D 53/228 |
| 9,289,729 B2 * | 3/2016 | Roy | B01D 71/56 |
| 9,475,010 B2 * | 10/2016 | Hoelzl | B01D 69/02 |
| 9,861,940 B2 * | 1/2018 | Koehler | B01D 69/125 |
| 10,150,083 B2 * | 12/2018 | Weiss | B01D 71/021 |
| 10,186,724 B2 * | 1/2019 | Gasda | H01M 8/0668 |
| 2005/0045029 A1 | 3/2005 | Colling et al. | |
| 2008/0071126 A1 | 3/2008 | Ou et al. | |
| 2008/0237126 A1 * | 10/2008 | Hoek | B01D 67/0079 210/637 |
| 2009/0149686 A1 | 6/2009 | Leflaive et al. | |
| 2011/0155662 A1 | 6/2011 | Liu et al. | |
| 2014/0100406 A1 | 4/2014 | Liu et al. | |
| 2014/0250669 A1 * | 9/2014 | Charkoudian | B01D 67/0093 29/458 |
| 2015/0321147 A1 | 11/2015 | Fleming et al. | |

OTHER PUBLICATIONS

Koros et al., "Water and Beyond: Expanding the Spectrum of Large-Scale Energy Efficient Separation Processes", AIChE Journal, Jul. 31, 2012, pp. 2624-2633, vol. 58, iss. 9, John Wiley & Sons, Inc.

Xu et al., "Olefins-selective asymmetric carbon molecular sieve hollow fiber membranes for hybrid membrane-distillation processes for olefin/paraffin separations", Journal of Membrane Science, 2012, pp. 314-323, vol. 423-424, iss. 15, Elsevier, ScienceDirect.

Minceva et al., "Modeling and simulation of a simulated moving bed for the separation of p-ylene", Industrial and Engineering Chemistry Research, 2002, pp. 3454-3461, vol. 41. iss. 14, ACS Publications.

Kiyono et al., "Effect of pyrolysis atmosphere on separation performance of carbon molecular sieve membranes", Journal of Membrane Science, 2010, pp. 2-10, vol. 359, iss. 1, Elsevier, ScienceDirect.

Kiyono et al., "Effect of polymer precursors on carbon molecular sieve structure and separation performance properties", Carbon, 2010, pp. 4432-1141, vol. 48, iss. 15, Elsevier, ScienceDirect.

Kiyono et al., "Generalization of effect of oxygen exposure on formation and performance of carbon molecular sieve membranes", Carbon, 2010, pp. 4442-4449, vol. 48 iss. 15, Elsevier, ScienceDirect.

Williams et al., "Gas separation by carbon membranes", Advanced Membrane Technology and Applications, 2010, pp. 599-631, John Wiley & Sons, Inc.

Vu et al., "Effect of condensable impurity in CO2/CH4 gas feeds on performance of mixed matrix membranes using carbon molecular sieves", Journal of membrane science. 2003, pp. 233-239, vol. 221, iss. 1, Elsevier, ScienceDirect.

Rungta et al., "Carbon molecular sieve dense film membranes derived from Matrimid® for ethylene/ethane separation", Carbon, 2012, pp. 1488-1502, vol. 50, iss. 4, Elsevier, ScienceDirect.

Ma et al., "Carbon molecular sieve gas separation membranes based on an intrinsically microporous polyimide precursor", Carbon. 2013, pp. 88-96, vol. 62, Elsevier, ScienceDirect.

Xu et al., "Matrimid® derived carbon molecular sieve hollow fiber membranes for ethylene/ethane separation", Journal of Membrane Science, 2011, pp. 138-147, vol. 380, iss. 1, Elsevier, ScienceDirect.

Cussler, "On separation efficiency", AIChE Journal, 2012, pp. 3825-3831, vol. 58, iss. 12, John Wiley & Sons, Inc.

Wade, "Distillation plant development and cost update", Desalination. 2001, pp. 3-12, vol. 136, iss. 1-3, Elsevier, ScienceDirect.

Avlontis et al., "Energy consumption and membrane replacement cost for seawater RO desalination plants", Desalination, 2003, pp. 151-158, vol. 157, iss 1-3, Elsevier, ScienceDirect.

White, "Development of large-scale applications in organic solvent nanofiltration and pervaporation for chemical and refining processes", Journal of membrane science, 2006, pp. 26-35, vol. 286, iss. 1, Elsevier, ScienceDirect.

Bhore et al., "New membrane process debottlenecks solvent dewaxing unit", Oil and Gas Journal, 1999, pp. 67-74, vol. 97, iss. 46, Pettroleum Pub. Co.

Gould et al., "Membrane separation in solvent lube dewaxing", Environmental Progress, 2001, pp. 12-16, vol. 20, iss. 1, John Wiley & Sons, Inc.

Silva et al. "Solvent transport in organic solvent nanofiltration membranes",Journal of membrane science, 2005, pp. 4-59, vol. 262, iss. 1, Elsevier, ScienceDirect.

Lin et al., "Nanofiltration membrane cascade for continuous solvent exchange", Chemical Engineering Science, 2007, pp. 2728-2736, vol. 62, iss. 10, Elsevier, ScienceDirect.

Schmidt et al., "Characterisation of organic solvent nanofiltration membranes in multi-component mixtures: Phenomena-based modelling and membrane modelling maps", Journal of Membrane Science, 2013, pp. 183-199, vol. 445, iss. 15, Elsevier, ScienceDirect.

Whu et al., "Nanofiltration studies of larger organic microsolutes in methanol solutions", Journal of Membrane Science, 2000, pp. 159-172, vol. 170, Elsevier, ScienceDirect.

Wijmans et al., "The solution-diffusion model: a review", Journal of membrane science, 1995, pp. 1-21, vol. 107, iss. 1, Elsevier, ScienceDirect.

See Toh et al., "Polymeric membranes for nanofiltration in polar aprotic solvents," Journal of Membrane Science, 2007, pp. 3-10, vol. 301, iss. 1, Elsevier, ScienceDirect.

Razdan et al., "Novel membrane processes for separation of organics", Current Science, 2003, pp. 761, vol. 85. iss. 6.

(56) References Cited

OTHER PUBLICATIONS

Gibbins et al., "Observations on solvent flux and solute rejection across solvent resistant nanofiltration membranes", Desalination, 2002, pp. 307-313, vol. 147, iss. 1, Elsevier, ScienceDirect.

See Toh et al., "The influence of membrane formation parameters on the functional performance of organic solvent nanofiltration membranes", Journal of membrane science, 2007, pp. 236-250, vol. 299, iss. 1, Elsevier, ScienceDirect.

Guizard et al., "Potentiality of organic solvents filtration with ceramic membranes. A comparison with polymer membranes", Desalination, 2002, pp. 275-280, vol. 147, iss. 1, Elsevier, ScienceDirect.

Kingsbury et al., "A morphological study of ceramic hollow fibre membranes", Journal of Membrane Science, 2009, pp. 134-140, vol. 328, iss. 1, Elsevier, ScienceDirect.

PCT/US2016/061251 International Search Report and Written Opinion dated Feb. 21, 2017.

Bhuwania et al., "Engineering substructure morphology of asymmetric carbon molecular siev hollow fiber membranes", Carbon, Sep. 1, 2014, pp. 417-434, vol. 76, Elsevier, ScienceDirect.

Koresh et al., "Molecular Siev Carbon Permselective Membrane. Part I. Presentation of a New Device for Gas Mixture Separation", Separation Science and Technology, Jun. 5, 1983, pp. 723-745, vol. 18, No. 8.

Koh, et al., "Reverse osmosis molecular differentiation of organic liquids using carbon molecular sieve membranes", Science, Aug. 19, 2016, pp. 804-807, vol. 353, No. 6301, American Association for the Advancement of Science.

PCT/US2016/061259 International Search Report and Written Opinion dated Feb. 23, 2017.

International Preliminary Report on Patentability in PCT Application No. PCT/US2016/061251 dated May 24, 2018, 12 pages.

European Office Action in European Application No. 1679830.0 dated Jun. 20, 2018, 4 pages.

Final Office Action dated Jan. 14 2019 for U.S. Appl. No. 15/347,978 (7 pages).

Notice of Allowance and Fees Due dated Mar. 13, 2019 for U.S. Appl. No. 15/347,978 (8 pages).

U.S. Appl. No. 15/348,010 Notice of Allowability dated Sep. 7, 2018 (6 pages).

\* cited by examiner

REVERSE OSMOSIS MEMBRANES AND SEPARATIONS

CROSS-REFERENCE TO RELATED APPLICATIONS

This application claims priority to U.S. Provisional Application Ser. No. 62/367,175 and U.S. Provisional Application Ser. No. 62/367,168 both filed on Jul. 27, 2016, and U.S. Provisional Application Ser. No. 62/254,792 filed on Nov. 13, 2015 each of which are herein incorporated by reference in their entirety.

FIELD

This description is related to membranes for various separations, such as separation by reverse osmosis, and corresponding methods for making and using such membranes.

BACKGROUND

Many petroleum refining and chemical production processes include one or more separation processes for isolating desirable products. Membrane separations are a potentially desirable method of separation due to the low energy requirements for performing a separation. However, use of membrane separations is limited to situations where a suitable membrane is available for performing a commercial scale separation.

Separation of para-xylene from other $C_8$ aromatics is an example of a separation that is difficult to perform via a boiling point separation. Current commercial methods involve selective crystallization or simulated moving bed chromatography to separate para-xylene from ortho- and meta-xylene. These methods are energy and/or equipment intensive.

U.S. Pat. No. 4,510,047 describes regenerated cellulose membranes for use in reverse osmosis separation of hydrocarbonaceous compounds, such aromatic extraction solvents. The regenerated cellulose membranes are susceptible to pore swelling in the presence of such solvents.

U.S. Pat. No. 4,571,444 describes methods for separating alkylaromatic compounds from aromatic solvents using asymmetric polyimide fiber membranes. The membrane is described as being suitable for at least partially separating benzene, toluene, and/or ethyl benzene from single ring aromatic compounds that are alkylated with a $C_8$ to $C_{20}$ alkyl group.

SUMMARY

In various aspects, a membrane structure comprising a first membrane layer and a second membrane layer is provided. The first membrane layer can comprise a porous carbon layer and/or a porous metal structure. Optionally, the porous carbon layer or porous metal structure can have a pore volume of at least 0.2 cm³/g of pores with a median pore size of at least 20 nm. The second membrane layer of the membrane structure can comprise a porous carbon layer having a BET surface area of at least about 100 m²/g (or at least about 300 m²/g), the second membrane layer having a pore size distribution comprising a smallest substantial pore size peak having a median pore size of about 3.0 Angstroms to about 50 Angstroms. Optionally, the smallest substantial pore size peak can have a median pore size of about 3.0 Angstroms to about 10 Angstroms, or about 5.8 Angstroms to about 6.8 Angstroms. Optionally, the membrane structure can correspond to a hollow fiber membrane structure. Optionally, the substantial pore size peak corresponding to the smallest median pore size can have a median pore size when the membrane structure is exposed to a liquid for separation that differs by 10% or less (or 5% or less or 2% or less) from the median pore size when the membrane structure is not exposed to the liquid for separation.

In some aspects, a method is provided for making a membrane structure comprising a first membrane layer and a second membrane layer. In aspects where the membrane structure comprises a plurality of porous carbon layers, the method can include forming a membrane structure comprising a first membrane layer and a second membrane layer, the first membrane layer having a pore volume of at least 0.02 cm³/g of pores with a median pore size of at least 20 nm, the second membrane layer comprising a partially fluorinated ethylene and/or propylene polymer having a BET surface area of less than 50 m²/g; cross-linking the membrane structure to form a cross-linked membrane structure having a storage modulus of at least about 200 MPa at 100° C.; pyrolyzing the cross-linked membrane structure at a pyrolysis temperature of about 450° C. to about 650° C. in a substantially inert atmosphere to form a pyrolyzed membrane structure, the first membrane layer of the pyrolyzed membrane structure having a pore volume of at least 0.2 cm³/g of pores with a median pore size of at least 20 nm, the second membrane layer of the pyrolyzed membrane structure having a BET surface area of at least about 100 m²/g (or at least about 300 m²/g), the second membrane layer having a pore size distribution comprising a smallest substantial pore size peak having a median pore size of about 3.0 Angstroms to about 50 Angstroms. Optionally, the smallest substantial pore size peak can have a median pore size of about 3.0 Angstroms to about 10 Angstroms, or about 5.8 Angstroms to about 6.8 Angstroms. Optionally, the membrane structure can correspond to a hollow fiber membrane structure. Optionally, the first membrane layer and the second membrane layer can each independently correspond to a polymer comprising a polyimide polymer, a partially fluorinated ethylene polymer, a partially fluorinated propylene polymer, a polyimide polymer, a polyamide-imide polymer, a polyetherimide polymer, or a combination thereof. Optionally, the the first membrane layer and/or the second membrane layer can be a partially fluorinated ethylene and/or propylene polymer, such as polyvinylidene fluoride.

In aspects where the membrane comprises a first membrane layer corresponding to a porous metal structure and a second membrane layer corresponding to a porous carbon layer, the method can include forming an extruded structure, cast structure, or combination thereof comprising a mixture of metal particles having a characteristic dimension of about 2.0 µm to about 5.0 µm and a binder, the binder optionally being a polymer binder. The extruded structure, cast structure, or combination thereof can then be calcined at a temperature of about 800° C. to about 1300° C. to form a porous metal structure having a pore volume of at least about 0.2 cm³/g of pores with a median pore size of at least about 20 nm. A polymer layer can then be formed on a surface of the porous metal structure. Optionally, the polymer layer can be cross-linked. The optionally cross-linked polymer can then be pyrolyzed at a pyrolysis temperature of about 450° C. to about 650° C. in a substantially inert atmosphere to form an asymmetric membrane structure comprising the pyrolyzed polymer layer, the pyrolyzed polymer layer having a BET surface area of at least about 100 m²/g, the pyrolyzed polymer layer having a pore size distribution comprising a smallest substantial pore size peak having a median pore size of about 3.0 Angstroms to about 50 Angstroms. Optionally, the smallest substantial pore size peak can have a median pore size of about 3.0 Angstroms to about 10 Angstroms, or about 5.8 Angstroms to about 6.8 Angstroms. Optionally, the membrane structure can correspond to a hollow fiber membrane structure. Optionally, the polymer can comprise a polyimide polymer, a partially fluorinated ethylene polymer, a partially fluorinated propylene polymer, a polyimide polymer, a polyamide-imide polymer, a polyetherimide polymer, or a combination thereof. Optionally, the polymer can correspond to a partially fluorinated ethylene and/or propylene polymer, such as polyvinylidene fluoride.

In still other aspects, methods for using a membrane structure to separate components can be provided, such as methods for performing a separation under liquid phase conditions. A liquid phase separation can correspond to, for example, a reverse osmosis or a forward osmosis separation. The methods can include performing a membrane separation on a feed stream comprising a first component and a second component. Depending on the aspect, the first component and the second component can comprising a hydrocarbon, a hydrocarbonaceous compound, an inorganic compound, or a combination thereof. For example, in some aspects the first component can correspond to water. In other aspects, the first component and the second component can correspond to hydrocarbonaceous and/or hydrocarbon compounds. The feed stream can include, for example, 5 wt % to 95 wt % of the first component. The separation can result in formation of a permeate enriched in the first component and a retentate depleted in the first component. The membrane separation can be performed by exposing the feed stream to a membrane structure comprising a first membrane layer and a second membrane layer under reverse osmosis conditions or forward osmosis conditions, the reverse osmosis conditions or forward osmosis conditions comprising a feed pressure of at least 0.2 MPag, the second membrane layer comprising a porous carbon layer having a pore size distribution comprising a smallest substantial pore size peak having a median pore size of about 3.0 Angstroms to about 50 Angstroms. Optionally, the membrane can correspond to a membrane structure as described herein and/or a membrane structure formed according to a method of making a membrane structure as described herein.

DETAILED DESCRIPTION

Figure 1:
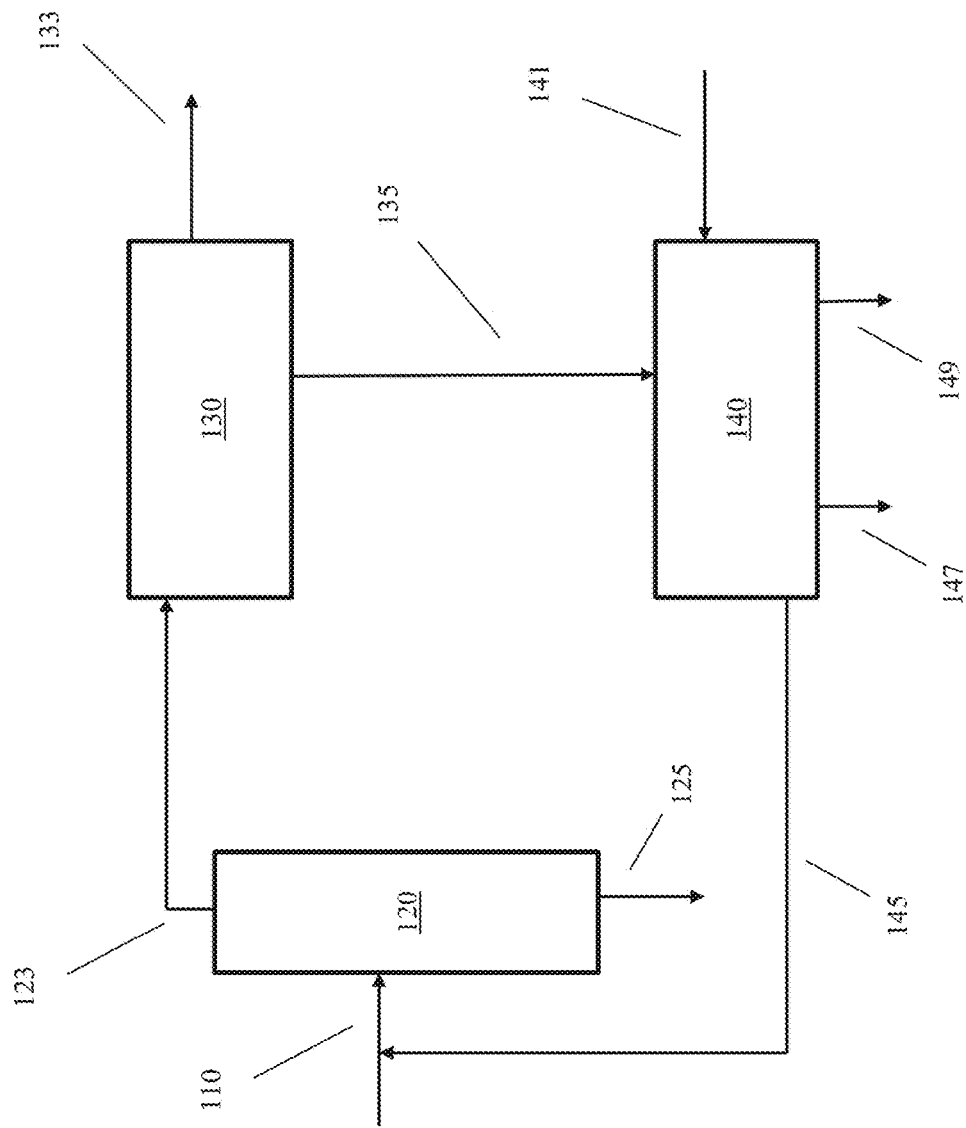
FIG. 1 schematically shows a process configuration for separation a stream of higher purity para-xylene from a mixed aromatic input stream.

In various aspects, asymmetric membrane structures are provided that are suitable, for example, for hydrocarbon reverse osmosis of small hydrocarbons. In a specific example, an asymmetric membrane structure can have an amorphous pore network with a smallest or controlling pore size that is suitable for separation of para-xylene (p-xylene) from ortho-xylene (o-xylene) and meta-xylene (m-xylene). Methods for making an asymmetric membrane structure from polyvinylidene fluoride (or another partially fluorinated monomer) are also provided. An example of a suitable asymmetric membrane structure can be a hollow fiber membrane. When a polymer is used to form a membrane structure, the membrane structure can be subsequently cross-linked and/or pyrolyzed prior to use. Cross-linking of the membrane structure can stabilize various portions of the membrane structure, so that desired properties are achieved and/or maintained during a subsequent pyrolysis step.

Pyrolysis can then be used to convert the polymeric membrane structure to a porous carbon structure with a higher ratio of carbon to hydrogen.

In this discussion, the notation "$C_x$" refers to a hydrocarbon stream having at least 50 wt % of hydrocarbons containing "x" number of carbons. The notation "$C_{x+}$" refers to a hydrocarbon stream having at least 50 wt % of hydrocarbons containing "x" or more carbons. For these definitions, a hydrocarbon stream is defined to include streams where at least a portion of the compounds in the stream contain heteroatoms other than carbon and hydrogen.

Asymmetric Membrane Structure

In various aspects, the membranes described herein can correspond to membranes having an asymmetric membrane structure. In an asymmetric membrane structure, a first membrane layer can correspond to a selective layer while a second membrane layer can correspond to a porous support layer. In aspects where a polymer is initially used to form a membrane structure, unless otherwise specified, the properties described in this section correspond to the properties of the membrane structure after any cross-linking and/or pyrolysis.

The first membrane layer or selective layer can have an amorphous interconnected pore structure. The amorphous interconnected pore structure can allow for selective separation of compounds based on molecular size under conditions suitable for hydrocarbon reverse osmosis. Because passage of permeating species through the selective layer is constrained during a separation, the selective layer can be relatively thin to maintain a desirable transport rate across the membrane. For example, the thickness of the selective layer can be about 0.08 µm to about 5 µm. Depending on the aspect the thickness of the selective layer can be about 0.1 µm to about 5 µm, or about 0.1 µm to about 3 µm, or about 0.1 µm to about 2.0 µm, or about 0.1 µm to about 1.5 µm, or about 0.1 µm to about 1.0 µm, or about 0.1 µm to about 0.5 µm.

To provide a sufficient number of pores for transport, the selective layer can have a surface area as measured by nitrogen adsorption (BET) of at least about 100 m$^2$/g, or at least about 200 m$^2$/g, or at least about 300 m$^2$/g, or at least about 500 m$^2$/g, or at least about 600 m$^2$/g, or at least about 700 m$^2$/g of pores having a pore size between 5 Angstroms and 100 Angstroms, or between 5 and 75 Angstroms, or between 5 and 50 Angstroms, or between 5 Angstroms and 35 Angstroms, or between 5 Angstroms and 20 Angstroms. The pores in the selective layer can have any type of pore size distribution, such as a unimodal distribution, a bimodal distribution, or a multi-modal distribution.

Based in part on the interconnected nature of the amorphous pore structure, the transport characteristics of the selective layer can be defined based on the substantial pore size peak in the pore size distribution (such as pore width distribution) corresponding to the smallest median pore size. A substantial pore size peak is defined herein as a peak in a pore size distribution corresponding to at least 5 vol % of the pore volume. The pore size corresponding to a maximum height of a pore size peak in the pore size distribution can be referred to as a median pore size. The width of a pore size peak can be characterized based on the width of a pore size peak at half of the maximum height.

Depending on the nature of the selective layer, the substantial pore size peak corresponding to the smallest median pore size can have a median pore size of 3.0 Angstroms to 50 Angstroms, or 3.0 Angstroms to 20 Angstroms, or 5 Angstroms to 50 Angstroms, or 5.0 Angstroms to 20 Angstroms, or 10 Angstroms to 50 Angstroms, or 10 Angstroms to 20 Angstroms. For example, in some aspects, the substantial pore size peak corresponding to the smallest median pore size can have a median pore size of 3 Angstroms to 10 Angstroms, or 3.0 Angstroms to 9.0 Angstroms, or 3.0 Angstroms to 8.0 Angstroms, or 3.0 Angstroms to 7.0 Angstroms, or 3.0 Angstroms to 6.0 Angstroms, or 4.0 Angstroms to 10 Angstroms, or 4.0 Angstroms to 9.0 Angstroms, or 4.0 Angstroms to 8.0 Angstroms, or 4.0 Angstroms to 7.0 Angstroms, or 4.0 Angstroms to 6.0 Angstroms, or 5.0 Angstroms to 10 Angstroms, or 5.0 Angstroms to 9.0 Angstroms, or 5.0 Angstroms to 8.0 Angstroms, or 5.0 Angstroms to 7.0 Angstroms, or 5.0 Angstroms to 6.0 Angstroms, or 6.0 Angstroms to 11 Angstroms, or 6.0 Angstroms to 10 Angstroms, or 6.0 Angstroms to 9.0 Angstroms, or 6.0 Angstroms to 8.0 Angstroms, or 6.0 Angstroms to 7.0 Angstroms. In other aspects, the substantial pore size peak corresponding to the smallest median pore size can have a median pore size of 10 Angstroms to 15 Angstroms, or 15 Angstroms to 20 Angstroms. In still other aspects, the substantial pore size peak corresponding to the smallest median pore size can have a median pore size of 10 Angstroms to 20 Angstroms, or 20 Angstroms to 30 Angstroms, or 30 Angstroms to 40 Angstroms, or 40 Angstroms to 50 Angstroms.

For separation of ortho-xylene and/or meta-xylene from para-xylene and/or ethylbenzene, the selective layer can have a substantial pore size peak corresponding to a smallest median pore size of about about 5.8 Angstroms to about 6.8 Angstroms, or about 6.0 Angstroms to about 7.0 Angstroms, or about 6.0 Angstroms to about 6.8 Angstroms. As an example, a selective layer can have a substantial pore size peak corresponding to a smallest median pore size of about 6.0 Angstroms to about 6.5 Angstroms, such as about 6.2 Angstroms.

It is noted that the various pore sizes described above correspond to pore sizes present in the selective layer both when the membrane structure is exposed to a liquid and when a liquid is not present. For example, the substantial pore size peak corresponding to the smallest median pore size can have a size when a liquid for separation is present that differs by 10% or less, or 5% or less, or 2% or less from the size when the membrane structure is not exposed to a liquid for separation. This is in contrast to various "swellable" polymer membrane structures that exhibit a change (typically increase) in pore size when exposed to a liquid for separation. A liquid for separation can correspond to a component being separated or to a solvent and/or carrier for components being separated. Examples of suitable solvents include, but are not limited to, water, hydrocarbons that are a liquid at 25° C. and 1 bar (100 kPa), alcohols that are a liquid at 25° C. and 1 bar (100 kPa), or combinations thereof.

Another way of characterizing the amorphous pore network can be based on the width of the substantial pore size peak corresponding to the smallest median pore size. The width of the pore size distribution for the smallest median pore size can impact the ability of the selective layer to act as a separation membrane. For an effective separation, the width of the smallest median pore size peak can be characterized relative to the difference in the molecular diameters of the target compounds being separated. In some aspects, the width of the substantial pore size peak corresponding to the smallest median pore size (i.e., at half of the peak height) can be about 75% or less of the difference in molecular diameter between target compounds for separation, or about 60% or less, or about 50% or less, or about 40% or less. The target compounds for separation can also be defined in part based on the relative molecular diameters and the relative molecular weights of the compounds. In some aspects, the difference in relative molecular diameters for the target compounds for separation can be about 3.0 Angstroms or less, or about 2.5 Angstroms or less, or about 2.0 Angstroms or less, or about 1.5 Angstroms or less, or about 1.1 Angstroms or less. Additionally or alternately, the molecular weights of the target compounds for separation can differ by about 20 g/mol or less, or about 15 g/mol or less, or about 10 g/mol or less. It is noted that for some separations, the target compounds may have approximately the same molecular weight (i.e., the molecular weights for separation differ by less than 0.1 g/mol). An example is separation of p-xylene from m-xylene and/or o-xylene. In this discussion, target compounds that effectively have the same molecular weight to within 0.1 g/mol of sensitivity are defined as being included in the definition of compounds that differ by about 20 g/mol or less, or about 15 g/mol or less, or about 10 g/mol or less.

The second layer can provide structural support for the first layer while having a sufficiently open pore network to allow for viscous flow across the second layer within the pore structure. This can correspond to having a median pore size in the second layer of at least about 20 nm, but any convenient pore size up to tens of microns can potentially be suitable so long as the porous structure is structurally stable under reverse osmosis conditions. In some aspects, a suitable pore volume for the second layer can be at least about 0.2 cm$^3$/g, or at least about 0.3 cm$^3$/g. The thickness of the second layer can be any convenient thickness that provides suitable structural support, such as 20 microns to 200 microns.

Another indicator of structural integrity can be the storage modulus for the membrane structure. In various aspects, the membrane structure can have a storage modulus of at least about 100 MPa, or at least about 200 MPa, or at least about 300 MPa, or at least about 400 MPa, at a temperature of 100° C., or a temperature of 200° C., or a 300° C.

Depending on the nature of how the membrane structure is fabricated, a transition region can be present between the first selective layer and the second support layer. The transition region can have any convenient thickness, but typically will be on the order of a few microns or less. In some aspects, the transition region can have a gradient of pore properties that transitions from the properties of the first selective layer to the properties of the second support layer.

Another way of characterizing a membrane structure is from single component transport studies. One use for single component transport studies is to characterize the defect density of a membrane. In various aspects, the membrane structures described herein can correspond to membrane structures with low defect densities. Without being bound by any particular theory, it is believed that membrane structures composed of partially fluorinated polymers can be formed with low defect densities, such as by spinning of a partially fluorinated polymer to form a hollow fiber membrane structure. The low defect density from the partially fluorinated polymer membrane structure can be carried over to a porous carbon membrane structure that is formed after pyrolysis. The pyrolysis of a partially fluorinated polymer membrane structure and/or cross-linking of such a membrane structure may also assist with reducing the number of defects present in a membrane structure.

Defects provide nonselective permeation pathways through a membrane, which can diminish, reduce, or minimize the selectivity of a membrane for a desired separation. Flow through these nonselective permeation pathways can increase significantly as the transmembrane pressure is increased. This increase is proportionally faster than the increase in transmembrane pressure. Defect density in a membrane structure can be characterized by permeation studies in which the feed is pressurized and the permeate is drawn off at atmospheric pressure ($P^{permeate}$~14.7 psi). The temperature of the study can be chosen such that the feed and permeate are in the liquid phase. Preferred temperatures for the study can be between 0° C. and 200° C.; or 10° C. and 150° C.; or 20° C. and 100° C.; or 25° C. and 75° C. Molar flux, $\mathcal{N}_i$, (Moles/(Meter$^2$ Second) through the membrane is measured as a function of the feed pressure ($P^{feed}$). Initial feed pressures for the study can be selected so that $P^{feed}$ is at least 3 times greater than $P^{permeate}$, or at least 6 times greater than $P^{permeate}$, or preferably at least 10 times greater than $P^{permeate}$. In some aspects, the characterization can be started with as high a feed pressure as possible. This can be in a range from 200 to 800 psia or from 400 psia to 750 psia. In a high quality membrane with an acceptable number of defects, the permeance, $\mathcal{N}_i/(P^{feed}-P^{permeate})$ can increase by less than a factor of 5 when the feed pressure is doubled and by less than a factor of 10 when the feed pressure is quadrupled. In a higher quality membrane with fewer defects, the permeance, $\mathcal{N}_i/(P^{feed}-P^{permeate})$ can increase by less than a factor of 3 when the feed pressure is doubled or by less than a factor of 6 when the feed pressure is quadrupled. In a very high quality membrane with even fewer defects, the permeance, $\mathcal{N}_i/(P^{feed}-P^{permeate})$ can change by less than a factor of 2 when the feed pressure is doubled and by less than a factor of 4 when the feed pressure is quadrupled. In an even higher quality membrane with yet fewer defects, the permeance, $\mathcal{N}_i/(P^{feed}-P^{permeate})$ changes by less than a factor of 1.15 when the feed pressure is doubled and by less than a factor of 1.25 when the feed pressure is quadrupled. It is also possible to characterize the membrane quality using permeate pressures in a range between 0.5 and 10 bara, or 1 and 5 bara, so long as the permeate is in the liquid phase. Thus, membrane quality can generally be characterized for pressures between about 50 kPa and 1000 kPa, or between about 1.0 MPa and about 5.5 MPa, or between about 2.0 Mpa and about 5.0 MPa. In performing single component permeation studies to characterize the defect density of the membrane, it is generally preferred to use a molecule that has a minimum dimension slightly larger than the characteristic pore size of the membrane. In this discussion, a characteristic dimension of a membrane with an amorphous, interconnected membrane structure can correspond to the median pore size of the smallest substantial peak in the pore size (i.e. pore width) distribution. Ideally the minimum molecular dimension is about 0.5 to 0.6 Angstroms greater than the characteristic dimension of the pores in the membrane, or is about 1.0 to 1.2 Angstroms greater than the characteristic dimension of the pores in the membrane, or is about 2.0 to 2.2 Angstroms greater than the characteristic dimension of the pores in the membrane, or is about 5.0 to 5.3 Angstroms greater than the characteristic dimension of the pores in the membrane, or is about 10.0 to 10.4 Angstroms greater than the characteristic dimension of the pores in the membrane. The minimum dimension of a wide range of molecules has been documented in the literature. Additionally or alternatively, those skilled in the art can calculate the minimum molecular dimension using quantum chemical calculations. For a membrane with a characteristic size of about 6 Angstroms, ortho-xylene can be used to characterize the defect density, because it has a minimum molecular size of about 0.5 to 0.6 Angstroms greater than the characteristic size.

For a membrane with an acceptable number of defects, the pore size can also be characterized by performing single component permeation studies with two different sized molecules. The molecules are chosen to bracket the characteristic pores size of the membrane. For a membrane with a narrow pore size distribution the molecules can differ in their minimum dimension by 0.5 to 2 angstrom. For a membrane with a wider pore size distribution, the molecules can be chosen such that their minimum dimension differs by 2 to 4 angstroms. For a membrane with yet a wider pore size distribution the minimum molecular dimension can differ by 4 to 20 angstroms. For an acceptable reverse osmosis membrane, the ratio of single component permeances measured at the same temperature and pressure conditions with a transmembrane pressure, ($P^{feed} - P^{permeate}$), greater than 10 bara can be used to characterize the pore size distribution. In various aspects, the ratio of single component permeances can be greater than 2, preferably greater than 6, more preferably greater than 10, and even more preferably greater than 20 for at least one pair of molecules used to characterize the pore size distribution of the membrane. Optionally, the comparative single component permeation studies can be performed at higher transmembrane pressures, such as transmembrane pressures of at least 20 bara, or at least 30 bara, or at least 50 bara, or at least 100 bara. The width of the pore size distribution can then be taken from the smallest molecular size difference that produces an acceptable ratio of permeances. For a membrane with a characteristic size of about 6 Angstroms, a comparison of single component para-xylene and ortho-xylene permeation can be used to characterize the pore size. Membranes with a ratio of single component permeances measured at the same temperature and pressure conditions with a transmembrane pressure greater than 2 are considered to be selective, with a ratio greater than 10 they are considered to be very selective and with a ratio greater than 20 are considered to be extremely selective.

Example of Making an Asymmetric Structure—Hollow Fiber

One method for making an asymmetric membrane structure having a first (selective) layer and a second (porous support) layer can be to first make an asymmetric hollow fiber structure. A suitable material for forming an asymmetric hollow fiber structure is polyvinylidene fluoride (PVDF). Other partially fluorinated ethylene polymers, partially fluorinated propylene polymers, and partially fluorinate ethylene-propylene co-polymers can also be suitable materials. In this description, a partially fluorinated ethylene polymer is defined as an ethylene polymer having an average number of fluorines per monomer unit of 1 to 3. Similarly, a partially fluorinated propylene polymer is defined as a propylene polymer having an average number of fluorines per polymer backbone carbon pair of 1 to 3.

In other aspects, other types of polymers can also be suitable for formation of an asymmetric membrane structure. Other examples of suitable polymers can include, but are not limited to, polyimide polymers (such as Matrimid® 5218, available from Ciba Specialty Chemicals), polyamide-imide polymers (such as Torlon® polymers available from Solvay Specialty Polymers), polyetherimide polymers (such as Ultem® resins available from SABIC), and partially or fully fluorinated polyethylene and/or polypropylene polymers (or co-polymers), such as polyvinylidene fluoride or polytetrafluoroethylene. More generally, suitable polymers may include glassy polymers, polymers with high intrinsic microporosity, and/or polymers that when are known to form a porous carbon structure when the cross-linked polymer is exposed to pyrolysis conditions.

A hollow fiber asymmetric membrane structure can be formed by using a co-annular spinneret with two types of PVDF solutions (or other partially fluorinated polymer solutions). In a dual-layer hollow fiber spinning process, polymer solutions comprising solvent, non-solvent, and polymer can be prepared. For the core polymer solution, dimethylacetamide (DMAc) can be used as a solvent and mixture of lithium chloride (LiCl) and water can be used as non-solvents. For the sheath polymer solution, a mixture of dimethylacetamide and tetrahydrofuran can be used as solvents and ethanol can be used as a non-solvent. For both core and sheath polymer solutions, poly(vinylidene) fluoride can be used as a polymer source. Asymmetric double layer hollow fibers can be created via nonsolvent phase inversion technique, which is known as dry jet wet-quench spinning. The aforementioned polymer solutions can be extruded through a spinneret into a non-solvent quench bath and further taken-up on a spinning drum at desired speed.

In various aspects, the sheath layer and core layer in a hollow fiber structure can be further processed to form a first layer and second layer as described above. Examples of suitable processing can include cross-linking of the polymer and pyrolysis of the cross-linked polymer. Prior to the further processing, the core layer can be a porous layer similar to the porous or second layer of the membrane structure. In some aspects, the pore volume of the core layer prior to further processing can be at least about 0.02 cm$^3$/g, with the pore volume corresponding to pores with a median pore size of at least about 20 nm. Prior to the further processing, the sheath layer can be a dense layer, but the sheath layer can have a different pore structure than the first layer as described above. For example, when PVDF is used as the polymer, the sheath layer prior to further processing can have a surface area (BET nitrogen adsorption) of about 100 m$^2$/g or less, or about 50 m$^2$/g or less, or about 30 m$^2$/g or less. This type of low surface area can indicate a sheath layer with limited permeability due to the limited availability of pores.

Cross-Linking of Polymer Structure

In aspects where an asymmetric membrane structure is formed using a polymer, such as a polymer formed from partially fluorinated ethylene or propylene, the membrane structure can be cross-linked. Any convenient cross-linking method suitable for cross-linking of both the first dense (sheath) layer and the second porous (core) layer can be used.

An example of a suitable cross-linking method can be to immerse the membrane structure in a methanol-based cross-linking solution. The cross-linking solution can be formed by dissolving sodium hydroxide and p-xylylenediamine in methanol. Additionally, magnesium oxide powders can be added to the solution as an HF sink. The membrane structure can be immersed into the solution and slowly stirred at room temperature for a desired period of time, such as 12 hours to 96 hours. In some aspects, selection of a different cross-linking agent may result in a different smallest median pore size in the selective layer.

Prior to and/or after cross-linking the membrane structure (such as a hollow fiber structure) can be solvent exchanged and dried. Examples of suitable fluids for solvent exchange are methanol and water. An example of a drying procedure can be drying under a pressure of less than 100 kPa, or less than 10 kPa, or less than 1 kPa, at a temperature between 50° C. and 150° C.

Pyrolysis of Polymer Membrane Structure

After any optional cross-linking, a polymer membrane structure can be pyrolyzed. Pyrolysis of the polymer membrane structure can convert a least a portion of the polymer structure to a more carbonaceous material. In other words, the carbon to hydrogen ratio in the membrane structure can be increased. After pyrolysis, the layers of the membrane structure can be referred to as porous carbon layers. Depending on the pore size, the selective layer can alternatively be referred to as a carbon molecular sieve.

Pyrolysis can be performed by heating the membrane structure in an inert atmosphere, such as an atmosphere comprising nitrogen and/or a noble gas (e.g. argon). The atmosphere can have a reduced or minimized content of oxygen, such as less than 50 vppm, or less than 10 vppm. During pyrolysis, the membrane structure can be heated in the inert atmosphere according to a desired heating profile until a target temperature is achieved. The target temperature for pyrolysis can be between 400° C. to 650° C. For example, the pyrolysis temperature can be at least about 400° C., or at least about 450° C., or at least 500° C., or at least 550° C., and/or about 650° C. or less, or about 600° C. or less. The target temperature can be maintained for a period of time, such as 0.5 hours to 5 hours. The heating profile for achieving the target temperature can be any convenient profile. Optionally, the heating profile can include multiple heating rates. For example, the initial temperature ramp can be at a higher rate, such as 10° C./min, with the temperature ramp being reduced to one or more lower values as the temperature in the pyrolysis oven approaches the target temperature. In general, the temperature ramp rate can range from 0.1° C./min to 25° C./min with as many temperature ramp rates as desired, depending on the nature of the desired profile. Optionally, the heating profile can maintain one or more temperatures other than the target pyrolysis temperature for a period of time.

Example of Making an Asymmetric Structure—Porous Metal Support

In the prior example, a dual layer hollow fiber structure was formed by using a dual-layer spinning process. Another option for making an asymmertric structure can be to first form a hollow fiber structure and then add a coating layer to provide the asymmetric structure. This can allow for separate processing conditions for the core or first layer and the additional coating layer, such as higher severity conditions for the core layer or higher severity conditions for the additional coating layer.

When forming an asymmetric structure by first forming a hollow fiber structure and then adding a coating layer, the initial hollow fiber structure can correspond to a metal or metal-enhanced fiber structure. For example, metal particles can be mixed with a binder, such as a polymer binder, for extrusion using a hollow fiber spinning system. The resulting extruded hollow fiber can then be calcined/sintered to remove the binder and form a porous metal structure. More generally, a porous metal structure can be formed using any convenient type of process that allows for extrusion (or other formation) of a layer or other structure. For example, a mixture of metal particles and polymer binder can be extruded to form a sheet of a desired thickness. The sheet can then be calcined as described below to remove the polymer portion and form a porous metal support structure having (roughly) the shape of the extruded sheet. An asymmetric structure can then be formed by depositing a coating layer of a desired polymer on the sheet of porous metal support structure. As another example, a mixture of metal particle and polymer binder can be cast to form a structure having a desired shape, such as a hollow fiber shape. After calcining/sintering to form a porous metal structure, a coating layer of a polymer can be added to surface of the porous metal structure to allow for formation of an asymmetric membrane structure.

Suitable metal particles can include, but are not limited to, metal particles comprising and/or composed of stainless steel, nickel, chrome, copper, silver, gold, platinum, palladium, and combinations thereof. The metal particles can have an average characteristic length of about 2.0 µm to about 5.0 µm. For particles having a roughly spherical shape, including shapes such as ellipsoids or ovoids, the characteristic length can correspond to a length of the particle along at least one axis for the particle. Examples can include a diameter for a sphere or the length along the major axis of an ellipse. For particles having an irregular shape and/or having a cylindrical type shape (with one axis being substantially larger than another axis), the characteristic length can correspond to the largest length associated with any orientation of the particle. It is noted that the characteristic length for the particles can influence the pore size in the resulting porous metal porous support.

Polymers can be a suitable binder for the metal particles. Examples of suitable binders can include, but are not limited to, partially fluorinated polymers as described above. The amount of metal particles to binder can be any convenient amount that allows for extrusion of the mixture of metal particles and binder. In various aspects, the volume ratio and/or weight ratio of metal to binder in the mixture can be from about 0.5 (more binder than metal) to about 5. The mixture of metal and binder can correspond to a precursor composition.

After extrusion or casting to form a hollow fiber, a flat layer or sheet, or another extruded/cast structure, the extruded/cast structure can be calcined and/or sintered under suitable conditions to form a porous metal (membrane) structure. The sintering for forming the porous metal structure can correspond to a partial sintering. During calcination, the polymer (or other binder) portion of the precursor composition can be removed. During and/or after removing the binder, sintering can be performed to allow the metal particles to flow together to form the porous metal structure. The porous metal membrane structure can be optionally sintered for additional time. The resulting porous metal structure can then substantially remain in an unchanged form during subsequent deposition/formation of a selective layer. The porous metal structure can correspond to the second or structural support layer of an eventual dual layer membrane structure. After calcining and/or sintering, the porous metal structure can have an average pore size of about 0.5 to about 5.0 µm. After calcining and/or sintering, the porous metal membrane structure can have the other properties identified above for a second or structural support layer.

Calcining and/or sintering of an extruded/cast structure can be performed at a temperature that is suitable for decomposition of the polymer or other binder. The temperature for calcining and/or sintering can also be suitable for sintering of the metal particles to form a continuous membrane structure (i.e., the porous metal membrane structure). In some aspects, calcining and sintering can be performed according to a single temperature program or profile for heating of the extruded/cast structure. In such aspects, sintering can be used to refer to both the calcination for polymer/binder decomposition and the sintering of the metal particles.

In aspects where separate calcination and sintering processes are performed, the calcination temperature can be about 400° C. to about 800° C., or about 450° C. to about 700° C. Calcining can be performed in an oxygen-containing atmosphere that can facilitate decomposition of the polymer or other binder. The calcining can be performed for a convenient period of time that is suitable for decomposition or other removal of the binder, such as about 10 minutes to about 10 hours, or about 1 hour to about 8 hours. During and/or after removal of the polymer or other binder, the metal particles can be sintered to form the porous metal structure. Sintering conditions can include a temperature of about 800° C. to about 1300° C., or about 900° C. to about 1200° C. The sintering atmosphere can be an oxygen-containing atmosphere or an inert atmosphere, such as a nitrogen or noble gas atmosphere. The sintering can be performed for about 1 hour to about 24 hours. It is noted that formation of the porous metal membrane structure does not require a sintering temperature that is above the melting point of the metal. Optionally, the sintering conditions can be substantially similar to the calcining conditions.

One option for increasing the temperature of an extruded/cast structure can be to increase the temperature of the extruded structure according to a temperature program or profile. A temperature program can include a series of program steps. As an example, a temperature program for sintering an extruded layer at 1100° C. can start with a first temperature ramp rate of about 5° C./min at temperatures between 50° C. and 200° C. The temperature ramp rate can then be reduced to about 1° C./min between 200° C. and 300° C. The temperature ramp rate can then be increased to about 5° C./min between 300° C. and 400° C. The temperature ramp rate can then be reduced to about 1° C./min between 400° C. and 600° C. The temperature ramp rate can then be increased to about 5° C. between 600° C. and 1100° C. When a temperature of about 1100° C. is achieved, the temperature can then be maintained for a desired period of time, such as about 60 minutes. Of course, other combinations of ramp rates, temperatures for changing the ramp rate, final temperature, and/or length of time at the final temperature can be used. Additionally or alternately, one or more additional temperature plateaus (i.e., ramp rate of about 0° C./min) can also be included prior to achieving the final temperature. Such plateaus can be maintained for a convenient or desired length of time. Additionally or alternately, the final temperature of the temperature program can be lower than a temperature achieved earlier in the temperature program.

After forming the porous metal structure, a polymer layer can be formed on the porous metal structure, such as by deposition. The deposited polymer layer can become a selective layer for a dual layer membrane structure. Without being bound by any particular theory, it is believed that because the porous metal structure can provide a structurally and chemically stable support layer, the conditions for forming the selective layer can be less severe. Additionally, the support from the support layer can potentially assist the selective layer in maintaining structural integrity during the formation of the selective layer. These features can allow for formation of selective layers using polymers that might not be suitable for direct formation of a dual layer hollow fiber structure as described above. For example, polyimide materials such as Matrimid® polymers can be suitable for forming a selective layer on a porous metal support layer. Because the porous metal structure is calcined in advance, the porous metal structure can provide support for the selective polymer layer during formation of the carbon membrane pore network. For example, one potential difficulty with forming an asymmetric hollow fiber structure can be that the selective layer can plasticize and collapse prior to final annealing/pyrolyzing of the hollow fiber structure. Cross-linking can help in avoiding this outcome, but requiring the use of polymers that form a suitable selective layer after cross-linking can restrict the types of selective layers that can be formed. Using a porous metal membrane support can enable a selective (polymer) layer to plasticize and collapse during annealing/pyrolyzing of the selective layer to form a carbon membrane while remaining suitable thin to serve as a selective layer. This can allow for use in the selective layer of polymers that are not cross-linked, so long as the non-cross-linked polymers can form a carbon membrane structure with a stable pore network.

Matrimid® polymers can be used to form a selective layer having a roughly 3-4 Angstrom size for the pore network. Other examples of suitable polymers for forming a selective layer can include, but are not limited to, polyimide polymers (such as Matrimid® 5218, available from Ciba Specialty Chemicals), polyamide-imide polymers (such as Torlon® polymers available from Solvay Specialty Polymers), polyetherimide polymers (such as Ultem® resins available from SABIC), and partially or fully fluorinated polyethylene and/or polypropylene polymers (or co-polymers), such as polyvinylidene fluoride or polytetrafluoroethylene. More generally, suitable polymers may include glassy polymers, polymers with high intrinsic microporosity, and/or polymers that when are known to form a porous carbon structure when the cross-linked polymer is exposed to pyrolysis conditions.

One option for depositing a polymer layer on a porous metal structure can be to use a dip coating process. The porous metal structure can be immersed in a polymer solution containing the desired polymer for the selective layer. The porous metal structure can then be withdrawn at a convenient rate to allow for formation of a coating layer of a desired thickness on the porous metal membrane structure. In some aspects, convenient pull rate for dip coating can correspond to about 1 cm/sec to about 10 cm/sec. As an example, a porous metal structure corresponding to a hollow fiber can have a polymer layer deposited on the exterior of the hollow fiber by dip coating. An end of the hollow fiber can correspond to a sealed end. A sealed end can be formed by any convenient method, such as by physically sealing the end with an epoxy or other sealing material. The hollow fiber can be dipped into a polymer solution starting with the sealed end so that a coating layer is formed on the exterior of the hollow fiber.

The coating layer formed on the porous metal structure can then be dried and/or pyrolyzed to form the selective layer. Drying can correspond to an optional initial process where solvent is removed from the coating layer at temperatures of about 100° C. or less and optionally at pressures below about 100 kPa-a. Pyrolysis can be performed by heating the membrane structure in an inert atmosphere, such as an atmosphere comprising nitrogen and/or a noble gas (e.g. argon). The atmosphere can have a reduced or minimized content of oxygen, such as less than 50 vppm, or less than 10 vppm. During pyrolysis, the membrane structure can be heated in the inert atmosphere according to a desired heating profile until a target temperature is achieved. The target temperature for pyrolysis can be between 400° C. to 650° C. For example, the pyrolysis temperature can be at least about 400° C., or at least about 450° C., or at least 500°

C., or at least 550° C., and/or about 650° C. or less, or about 600° C. or less. The target temperature can be maintained for a period of time, such as 0.5 hours to 5 hours. The heating profile for achieving the target temperature can be any convenient profile. Optionally, the heating profile can include multiple heating rates. For example, the initial temperature ramp can be at a higher rate, such as 10° C./min, with the temperature ramp being reduced to one or more lower values as the temperature in the pyrolysis oven approaches the target temperature. In general, the temperature ramp rate can range from 0.1° C./min to 25° C./min with as many temperature ramp rates as desired, depending on the nature of the desired profile. Optionally, the heating profile can maintain one or more temperatures other than the target pyrolysis temperature for a period of time.

As an example, a temperature program for pyrolysis at 500° C. can start with a first temperature ramp rate of about 10° C./min at temperatures between 50° C. and 250° C. The temperature ramp rate can then be reduced to about 4° C./min between 200° C. and 485° C. The temperature ramp rate can then be further reduced to about 0.2° C./min between 485° C. and 500° C. When a temperature of about 500° C. is achieved, the temperature can then be maintained for a desired period of time, such as about 120 minutes. Of course, other combinations of ramp rates, temperatures for changing the ramp rate, final temperature, and/or length of time at the final temperature can be used. Additionally or alternatively, one or more additional temperature plateaus (i.e., ramp rate of about 0° C./min) can also be included prior to achieving the final temperature. Such plateaus can be maintained for a convenient or desired length of time. Additionally or alternatively, the final temperature of the temperature program can be lower than a temperature achieved earlier in the temperature program.

Pyrolysis of the coating layer can result in formation of an asymmetric membrane structure. The asymmetric membrane structure can be substantially free of mesopore defects. One option for characterizing an asymmetric membrane structure with regard to mesopore defects can be to determine relative rates of He and $N_2$ permeability in a constant pressure gas permeation system. For example, single component gas phase permeation data can be collected at a membrane upstream pressure of about 100 psia (~700 kPa-a) and a temperature of about 35° C. Single component gas phase permeation rates can then be determined for two different components, such as He and $N_2$. The ratio of the He permeation rate to the $N_2$ permeation rate can then be compared with the Knudsen selectivity for He/$N_2$ permeation through large pores at low pressures of about 3.7. In various aspects, the ratio of permeation rates for He versus $N_2$ for an asymmetric membrane structure can be at least about 8.0, or at least about 10, or at least about 12, such as up to about 100 or more.

Another option for characterizing an asymmetric membrane structure can be based on single component liquid phase permeation. For example, an asymmetric membrane structure can be immersed and/or filled with a liquid of interest for permeation. The selective layer side of the asymmetric membrane structure can then be pressurized at a constant pressure using the liquid. During pressurization, it may be desirable to limit the pressurization rate to less than a threshold value, such as less than about 200 kPa/min, in order to reduce or minimize the possibility of membrane failure during pressurization. Steady state flux at a pressure can then be measured over time to determine a liquid phase permeation rate for the liquid.

As an example, a precursor structure (metal particles plus binder) for a stainless steel porous fiber substrate can be extruded as described above. The extrusion can include passing/extruding the structure through capillary quartz tubing to obtain a straight stainless steel substrate. The precursor structure can be calcined at ~600° C. for ~30 minutes to remove carbon from the polymer binder while minimizing oxidation. More generally, the full temperature profile for performing the calcination can be selected so that the overall shrinkage of the stainless steel structure (length and diameter) is about 65%. The resuling stainless steel substrate can then be dip coated as described above. Prior to dip coating, the substrate can be pre-soaked with a non-polar (neutral) solvent. The dip coating solution can correspond to, for example, a solution containing about 18 wt % PVDF in about 70 wt % of a solvent, such as tetrahydrofuran. The dip coating can be performed at an elevated temperature, such as 50° C. to 100° C. After dip coating, a water wash can be performed at a similar elevated temperature. The PVDF layer formed on the substrate can then be cross-linked, as described above. After removing the structure from the cross-linking environment, the structure can be washed by flushing the structure multiple time with warm deionized water to remove excess base. This can avoid exposing the stainless steel substrate to an acidic environment. Finally, the cross-linked polymer structure can be exposed to pyrolysis conditions as described above to form an asymmetric membrane structure, where the selective layer corresponds to the carbon membrane formed during pyrolysis and the substrate or support layer corresponds to the stainless steel layer or structure.

Hydrocarbon Reverse Osmosis

An asymmetric membrane as described herein can be used for performing membrane separations based on hydrocarbon reverse osmosis. Hydrocarbon reverse osmosis generally refers to a selective membrane separation where a separation is performed on hydrocarbon liquid containing at least two hydrocarbon or hydrocarbonaceous components. Hydrocarbonaceous components refer to compounds containing carbon and hydrogen that may also contain heteroatoms, such as oxygen or nitrogen. In some aspects, hydrocarbonaceous compounds are defined to include compounds having up to roughly equal numbers of carbons and heteroatoms (i.e., atoms different from carbon or hydrogen). Examples of hydrcarbonaceous compounds having roughly equal numbers of carbons and heteroatoms can include, but are not limited to, sugars and/or other carbohydrates. In some alternative aspects, hydrocarbonaceous compounds used as components in a reverse osmosis or forward osmosis separation can be limited to hydrocarbonaceous compounds having fewer heteroatoms than carbons.

The process is executed such that the hydrocarbon or hydrocarbonaceous components being separated are in the liquid phase in both the feed and permeate. In this discussion, a reverse osmosis process is defined as a process such that for at least one position along the length of the membrane, the hydrocarbon molecules (and/or hydrocarbonaceous molecules) being separated are in the liquid phase in both the feed and the permeate. In some aspects, there may be other components in the feed that depending on concentration, temperature, and pressure, can produce a two phase liquid/gas mixture in either the feed or permeate. Examples of gaseous molecular species that can be present that are not hydrocarbons or hydrocarbonaceous include hydrogen, nitrogen, carbon dioxide, carbon monoxide, hydrogen sulfide. Other light hydrocarbon components such a methane, ethane, ethylene, propane or butane can depending on pressure, temperature, and concentration produce a two phase liquid/gas mixture in either feed or permeate. Another non-hydrocarbon that can be present is water or water vapor.

Based on the interconnected nature of the amorphous pore network, the substantial pore size peak having the smallest median pore size for the pore network can determine the effective size of compounds that can pass through the selective layer. A first component having a molecular size less than the smallest median pore size of the pore network can selectively pass through the selective layer of the membrane structure, while a second component having a molecular size greater than the smallest median pore size can pass through the selective layer in a reduced or minimized amount.

In hydrocarbon reverse osmosis, a first hydrocarbon (or hydrocarbonaceous) component is separated from a second hydrocarbon (or hydrocarbonaceous) component based on a molecular size differential. Without being bound by any particular theory, it is believed that based on the nature of an interconnected amorphous pore network, permeating species have multiple diffusional routes through the network thus enabling faster/smaller diffusing molecules to pass slower/larger ones either through larger pores or through connected alternate pathways. This is in contrast to a crystalline pore structure, where the pore channels can become clogged by slower diffusing/larger molecules. This contrast is particularly important in liquid phase separations where pores are fully loaded with the permeating species.

In order to perform a reverse osmosis separation, the pressure on the feed side of the membrane structure can be sufficiently large to overcome the "osmotic pressure", or the driving force that can tend to cause a higher purity solution to transfer material to a lower purity solution across a membrane. At pressures below the osmotic pressure, the amount of permeate transferred across the membrane can be limited. The osmotic pressure for a hydrocarbon (or hydrocarbonaceous) component can be dependent on the nature of the component and the concentration of the component in the feed to the membrane. Examples of suitable feed pressures for overcoming the osmotic pressure can be at least about 30 bar (3.0 MPa), or at least about 35 bar (3.5 MPa), or at least about 40 bar (4.0 MPa), or at least about 50 bar (5.0 MPa), and/or up to about 200 bar (20 MPa) or less, or about 170 bar (17 MPa) or less, or about 150 bar (15 MPa) or less.

In selective hydrocarbon reverse osmosis, the liquid phase mole fraction of at least one hydrocarbon and/or hydrocarbonaceous component can be greater in the permeate than in the feed. In some aspects, the mole fraction of this component in the liquid phase can be at least 200% greater in the permeate when the molar concentration in the feed is in a range from 0.1% to 10%, 100% greater in the permeate when the molar concentration in the feed is in a range from 10% to 20%, 75% greater in the permeate when the molar concentration in the feed is in a range from 20% to 40%, 50% greater in the permeate when the molar concentration in the feed is in a range from 40% to 60%, 20% greater in the permeate when the molar concentration in the feed is in a range from 60% to 80%, and 10% greater in the permeate when the molar concentration in the feed is in a range from 80% to 90%. Preferably, the mole fraction of this component in the liquid phase can be at least 500% greater in the permeate when the molar concentration in the feed is in a range from 0.1% to 10%, and 250% greater in the permeate when the molar concentration in the feed is in a range from 10% to 20%.

Another metric for membrane performance can be the selectivity of a pair of hydrocarbon or hydrocarbonaceous components in the feed. The binary selectivity is defined as the ratio of their molar concentrations in the permeate flowing out of the membrane module divided by the concentration in the feed. For a pair of molecules A and B, the molecules can be chosen so that the selectivity is greater or equal to 1 with:

Selectivity=$[\chi_A(\text{Permeate})/\chi_B(\text{Permeate})]/[\chi_A(\text{Permeate})/\chi_B(\text{Permeate})]$ where $\chi_A$ (Permeate) is the mole fraction of A in the permeate, $\chi_B$ (Permeate) is the mole fraction of B in the permeate, $\chi_A$ (Feed) is the mole fraction of A in the feed, and $\chi_B$ (Feed) is the mole fraction of B in the feed. It is preferred that the membrane be operated in a reverse osmosis process such that there is at least one pair of hydrocarbon and/or hydrocarbonaceous components for which the selectivity is greater than 2, or 5, or 10, or 20, or 40, or 100. This can be achieved using a membrane a) that has a smallest median pore size in a range that can separate molecules A and B, b) that has a low defect density, and c) that can be operated with a transmembrane pressure sufficiently high to provide thermodynamic drive for selective permeation. Transmembrane pressures can be at least about 10 bar, or at least about 20 bar, or at least about 50 bar, or at least about 100 bar. Optionally but preferably, the flow rate of the feed across the membrane can be fast enough so that a selective separation will occur at a reasonable commercial time scale.

For hydrocarbon reverse osmosis, the feed can flow over the membrane at a pressure at least 2 bars greater than the pressure at which the permeate is drawn off. More preferably the feed is at a pressure at least 5 bars greater than the permeate pressure, or at least 10 bars greater than the permeate pressure, or at least 50 bars greater than the permeate pressure, or at least 100 bars greater than the permeate pressure, or at least 200 bars greater than the permeate pressure. It is preferable that the flux of the molecular species being selectively transported through the membrane increase as the transmembrane pressure (pressure difference between the feed and permeate) increases from 2 bar to 5 bar, or 2 bar to 10 bar, or 2 bar to 20 bar, or 2 bar to 100 bar.

As noted and defined above, in a reverse osmosis separation the hydrocarbon and/or hydrocarbonaceous species being separated are in the liquid phase on both the feed and permeate sides of the membrane for at least one point along the length of the membrane. In one mode of operation the hydrocarbon or hydrocarbonaceous species being separated are in the liquid phase of the feed being introduced into the membrane module and at least one of the species being separated is predominantly in the liquid phase of the permeate being drawn out of the membrane module. Pressure in the permeate can be sufficient so that the hydrocarbon species are in the liquid phase for at least one point along the permeate side of the membrane. Permeate pressure can be 0.25 bara or greater. In one mode of operation the permeate pressure can be in a range from 1 to 5 bara, which can reduce, minimize, or eliminate the need for a vacuum on the permeate side of the membrane.

In various aspects, the temperature for a hydrocarbon reverse osmosis separation can be any convenient temperature from about 0° C. to about 300° C. The temperature for a given separation can be dependent on the nature of permeate component and the nature of the retentate. Depending on the aspect, the separation temperature can be about 0° C. to about 100° C., or about 50° C. to about 150°

C., or about 100° C. to about 200° C., or about 150° C. to about 250° C., or about 200° C. to about 300° C. Alternatively, the separation temperature can be at least about 0° C., or at least about 25° C., or at least about 50° C., or at least about 75° C., or at least about 100° C., or at least about 125° C., or at least about 150° C., or at least about 175° C., or at least about 200° C., and/or about 300° C. or less, or about 275° C. or less, or about 250° C. or less, or about 225° C. or less, or about 200° C. or less, or about 175° C. or less, or about 150° C. or less, or about 125° C. or less, or about 100° C. or less.

As described above, the amorphous pore network of the membrane structure can allow for separation under reverse osmosis conditions. Another consideration for the membrane structure can be providing sufficient structural stability to maintain the integrity of the membrane structure under reverse osmosis conditions. At least a portion of the structural support for the membrane structure can be provided by the second porous layer. Optionally, additional support can be provided by using additional non-membrane materials to support or package the membrane structure.

Another option for providing additional structural integrity can be to use a hollow fiber membrane structure. The annular nature of a hollow fiber membrane structure can allow the membrane structure to be self-supporting. In one example of a configuration, a plurality of hollow fiber membrane structures can be located in a separation volume. A feed for separation can be introduced into the volume. The permeate from the membrane separation can enter the hollow bores of the hollow fiber membranes. The permeate within the bores of the hollow fibers can then be transported out of the separation volume.

Water Reverse Osmosis Separations and Other Separations Involving an Inorganic Component An asymmetric membrane as described herein can be used for performing membrane separations based on osmosis, such as water reverse osmosis or water forward osmosis. Water reverse osmosis and/or forward osmosis generally refers to a selective membrane separation where a separation is performed on an aqueous (liquid) mixture containing at least one component in addition to water. The additional component can correspond to an ionic component, an acidic component, and/or a hydrocarbonaceous component. Because the membrane of the present invention has enhanced chemical stability compared to polymeric membranes there are a variety of aqueous separations that can also potentially be performed.

In some separations, water can be separated from ionic components dissolved in the water based on the larger "net ionic diameter" of an ionic component. For example, water reverse osmosis can be used to produce potable water from saline waters, brackish waters, and/or chlorine containing waters. This can initially appear surprising, as the effective diameter of a water molecule can appear to be larger than either a sodium ion or a chloride ion. However, ionic species in aqueous solution cannot typically be transported across a membrane as a lone ion, such as in the form of a single $Na^+$ or $Cl^-$ ion. Instead, ionic species in aqueous solution can typically have a substantial number of additional water molecules coordinated with the ion in order to stabilize the ion charge. An ion along with the coordinated water molecules stabilizing an ion can be refered to as a hydrated ion. In order to pass a hydrated ion through a membrane, both the ion and the coordinating water molecules stabilizing the ion can be required to pass through together. The effective diameter of a hydrated ion can be substantially larger than the size of the ion itself. As a result, water can be separated from various types of ionic compounds by reverse osmosis based on the size difference between an individual water molecule and the size of a water-stabilized ion. For example, the size of various hydrated ions can be at least about 6.0 Angstroms, so that selective layers with a smallest substantial pore size of about 3.0 Angstroms to about 6.0 Angstroms can be suitable for reverse osmosis separations, such as at least about 3.5 Angstroms, or at least about 4.0 Angstroms, or at least about 4.5 Angstroms, or at least about 5.0 Angstroms and/or about 6.0 Angstroms or less, or about 5.5 Angstroms or less, or about 5.0 Angstroms or less, or about 4.5 Angstroms or less. In particular, a reverse osmosis separation of water from various types of hydrated ions can be performed using a selective layer having a smallest substantial pore size of about 3.0 Angstroms to about 6.0 Angstroms, or about 4.0 Angstroms to about 6.0 Angstroms, or about 3.5 Angstroms to about 5.5 Angstroms. Similar types of selective layers can allow for separation of water from hydrocarbon and/or hydrocarbonaceous compounds.

In addition to separation of water from sodium chloride, reverse osmosis and/or forward osmosis can more generally be used to separate water from a variety of ionic compounds/hydrated ions. Other examples can include, but are not limited to, separation of water from acids such as sulfuric acid, nitric acid, hydrochloric acid, organic acids, and/or other acids. Still other examples can correspond to separation of water from various other types of salts that dissociate in water. Separation of water from various types of acids/salts/other ionic compounds can be based on using a selective layer having a smallest substantial pore size that is large enough to allow transport of water (e.g., greater than about 3.0 Angstroms) and small enough to reduce, minimize, or exclude transport of the acids/salts/other ionic compounds and/or corresponding hydrated ions formed in aqueous solution by the acids/salts/other ionic compounds. Additionally or alternately, separation of water from various types of hydrocarbon/hydrocarbonaceous compounds can be based on using a a selective layer having a smallest substantial pore size that is large enough to allow transport of water (e.g., greater than about 3.0 Angstroms) and small enough to reduce, minimize, or exclude transport of the hydrocarbon and/or hydrocarbonaceous compounds.

In order to perform a reverse osmosis separation, the pressure on the feed side of the membrane structure can be sufficiently large to overcome the "osmotic pressure", or the driving force that can tend to cause a higher purity solution to transfer material to a lower purity solution across a membrane. At pressures below the osmotic pressure, the amount of permeate transferred across the membrane can be limited. The osmotic pressure for water can be dependent on the nature and concentration of the ionic compounds in an aqueous solution, with lower concentrations of ionic compounds corresponding to lower osmotic pressures. As an example, sea water can typically have a total salt concentration (NaCl plus other salts) of about 35 g/L, or about 3.5 wt %. The osmotic pressure for sea water can typically be greater than about 20 barg (~2.0 MPag), for example about 23 barg (~2.3 MPag) to about 26 barg (~2.6 MPag). To perform a water reverse osmosis separation on sea water, a pressure greater than the osmotic pressure can be used, such as a pressure of at least about 2.0 MPag, or at least about 2.6 MPag. The rate of separation during water reverse osmosis can be increased by increasing the feed pressure to the separation process. A convenient feed pressure can be a pressure that is roughly twice the osmotic pressure. Thus, feed pressures of at least about 4.0 MPag, or at least about 4.5 MPag, or at least about 5.0 MPag can be suitable.

Additionally or alternately, water reverse osmosis can be used to separate water from hydrocarbon/hydrocarbonaceous compounds. In some separations, water can be separated based on the larger molecular diameter of the hydrocarbon/hydrocarbonaceous components dissolved in water. In some separations, the hydrocarbons/hydrocarbonaceous components can correspond to the majority of the solution, with a small or trace amount of water that is separated based on molecular diameter. The process can be executed such that the water/hydrocarbonaceous components being separated are in the liquid phase in both the feed and permeate.

Examples of suitable feed pressures for overcoming the osmotic pressure for a water reverse osmosis separation can be dependent on the relative concentrations of water versus other components that are present in a feed. In some aspects, a feed including a majority of hydrocarbon and/or hydrocarbonaceous components may also include water. The amount of water may correspond to only trace amounts, such as less than about 1 wt %, or less than about 0.1 wt %, or a larger amount of water may be present, such as about 0.1 wt % to about 30 wt %, or about 0.1 wt % to about 20 wt %, or about about 1.0 wt % to about 10 wt %. In such aspects, a water reverse osmosis separation can correspond to separating a relatively small amount of water from a larger concentration of one or more excluded components. This can lead to substantial osmotic pressure. In order to have a feed pressure that is greater than the osmotic pressure to allow for separation to occur, the feed pressure can also be elevated. Examples of suitable feed pressures for overcoming the osmotic pressure for a water reverse osmosis separation for a low water content feed can be at least about 100 barg (~10 MPag), or at least about 150 barg (~15 MPag), or at least about 200 barg (~20 MPag), or at least about 250 barg (~25 MPag), and/or about 400 barg (~40 MPag) or less, or about 350 barg (~35 MPag) or less, or about 300 barg (~30 MPag) or less, or about 250 barg (~25 MPag) or less. In particular, the feed pressure for a water reverse osmosis separation for a low water content feed can be about 10 MPag to about 40 MPag, or about 10 MPag to about 25 MPag, or about 20 MPag to about 40 MPag.

In some aspects, a feed including a majority of water may also include ionic components and/or hydrocarbon/hydrocarbonaceous components may also include water. The concentration of components other than water may correspond to only trace amounts, such as less than about 1 wt %, or less than about 0.1 wt %, or a larger amount of components other than water may be present, such as about 0.1 wt % to about 30 wt %, or about 0.1 wt % to about 20 wt %, or about about 1.0 wt % to about 10 wt %. In such aspects, a water reverse osmosis separation can correspond to separating a relatively dilute solution of water to form a permeate having a still higher water concentration. Examples of suitable feed pressures for overcoming the osmotic pressure for a water reverse osmosis separation for a high water content feed can be at least about 10 barg (1.0 MPag), or at least about 15 barg (~1.5 MPag), or at least about 20 barg (~2.0 MPag), or at least about 25 barg (~2.5 MPag), or at least about 30 barg (3.0 MPag), and/or up to about 100 barg MPag) or less, or about 70 barg (~7.0 MPag) or less, or about 50 barg (~5.0 MPag) or less. In particular, the feed pressure for a water reverse osmosis separation can be about 10 barg (~1.0 MPag) to about 100 barg (~10 MPag), or about 15 barg (~1.5 MPag) to about 70 barg (~7.0 MPag), or about 10 barg (~1.0 MPag) to about 50 barg (~5.0 MPag).

More generally, examples of suitable feed pressures for overcoming the osmotic pressure for a water reverse osmosis separation for a feed can be at least about 10 barg (1.0 MPag), or at least about 15 barg (~1.5 MPag), or at least about 20 barg (~2.0 MPag), or at least about 25 barg (~2.5 MPag), or at least about 30 barg (3.0 MPag), or at least about 35 barg (3.5 MPag), or at least about 40 barg (4.0 MPag), or at least about 50 barg (5.0 MPag), and/or up to about 200 barg (20 MPag) or less, or about 170 barg (17 MPag) or less, or about 150 barg (15 MPag) or less. In particular, the feed pressure more generally for a water reverse osmosis separation can be about 15 barg (~1.5 MPag) to about 200 barg (~20 MPag), or about 40 barg (~4.0 MPag) to about 200 barg (~20 MPag), or about 50 barg (~5.0 MPag) to about 150 barg (~15 MPag).

In water reverse osmosis, the liquid phase mole fraction of water can be greater in the permeate than in the feed. In some aspects, the mole fraction of water in the liquid phase can be at least 200% greater in the permeate when the molar concentration in the feed is in a range from 0.1% to 10%, 100% greater in the permeate when the molar concentration in the feed is in a range from 10% to 20%, 75% greater in the permeate when the molar concentration in the feed is in a range from 20% to 40%, 50% greater in the permeate when the molar concentration in the feed is in a range from 40% to 60%, 20% greater in the permeate when the molar concentration in the feed is in a range from 60% to 80%, and 10% greater in the permeate when the molar concentration in the feed is in a range from 80% to 90%. Preferably, the mole fraction of water in the liquid phase can be at least 500% greater in the permeate when the molar concentration in the feed is in a range from 0.1% to 10%, and 250% greater in the permeate when the molar concentration in the feed is in a range from 10% to 20%.

Another metric for membrane performance can be the selectivity of a membrane for water relative to other compound(s) in the feed. In various aspects, the membrane can be operated in a reverse osmosis process such that there is at least one hydrated ion/hydrocarbonaceous compounds for which the selectivity is at least 2, or at least 5, or at least 10, or at least 20, or at least 40, or at least 100. This can be achieved using a membrane a) that has a pore size in a range that can separate water from a hydrated ion/hydrocarbonaceous compound, b) that has a low defect density, and c) that can be operated with a transmembrane pressure sufficiently high to provide thermodynamic drive for selective permeation. Transmembrane pressures can be at least about 10 barg (~1.0 MPag), or at least about 20 barg (~2.0 MPag), or at least about 50 barg (~5.0 MPag), or at least about 100 barg (~10 MPag). Optionally but preferably, the flow rate of the feed across the membrane can be fast enough so that a selective separation will occur at a reasonable commercial time scale.

For water reverse osmosis, the feed can flow over the membrane at a pressure at least about 2 barg (~0.2 MPag) greater than the pressure at which the permeate is drawn off. More preferably the feed can be at a pressure at least about 5 barg (~0.5 MPag) greater than the permeate pressure, or at least about 10 barg (~1.0 MPag) greater than the permeate pressure, or at least about 50 barg (~5.0 MPag) greater than the permeate pressure, or at least about 100 barg (~10 MPag) greater than the permeate pressure, or at least 200 barg (~20 MPag) greater than the permeate pressure. It is preferable that the flux of water transported through the membrane increase as the transmembrane pressure (pressure difference between the feed and permeate) increases from ~0.2 MPag to ~0.5 MPag, or ~0.2 MPag to ~1.0 MPag, or ~0.2 MPag to ~2.0 MPag, or ~0.2 MPag to ~10 MPag.

As noted and defined above, in a reverse osmosis separation the water being separated can be in the liquid phase on both the feed and permeate sides of the membrane for at least one point along the length of the membrane. Permeate pressure can be 0.25 bara (~25 kPa-a) or greater. In one mode of operation the permeate pressure can be in a range from 1.0 to 5.0 bara (~0.1 MPa-a to ~0.5 MPa-a), which can reduce, minimize, or eliminate the need for a vacuum on the permeate side of the membrane. In various aspects, the temperature for a water reverse osmosis separation can be any convenient temperature from about 4° C. to about 90° C.

Those of skill in the art will recognize the the conditions and considerations described above for water reverse osmosis can also apply in many instances to separations based on forward osmosis.

Examples of separations that can be facilitated by water reverse osmosis (and/or forward osmosis) can include, but are not limited to: i) Water purification: This includes but is not limited to producing potable water from saline waters, brackish waters, or chlorine containing waters. ii) Water removal from aqueous acids to concentrate the acid. An example of this is concentration of sulfuric acid. iii) Water removal from hydrocarbon conversion processes that produce water as a byproduct, such as to improve the purity of the resulting hydrocarbon conversion product. iv) Alcohol/water separations, such as to allow for high alcohol purity than can be achieved via distillation. v) Water removal from product streams coming from fermentation or bioconversion processes, such as to improve the purity of the fermentation and/or bioconversion product.

Additionally or alternately, hydrocarbon and/or hydrocarbonaceous compounds can be separated from inorganic compounds different from water. Separation of hydrocarbon/hydrocarbonaceous compounds from inorganic compounds (including hydrated inorganic ions) can take place in the presence of water, or the separation environment can include low or trace amounts of water, or the separation environment can be anhydrous. Inorganic compounds as described herein can include, but are not limited to, acids, salts, other ionic compounds, metals complexed with one or more ligands (including organic and/or inorganic ligands), and/or other compounds that have an effective size of 100 Angstroms or less for purposes of separation using a porous membrane or other porous separation structure. An example of a metal complexed with one or more ligands can be a homogeneous catalyst.

The temperature for separating hydrocarbons/hydrocarbonaceous compounds from inorganic compounds can correspond to conditions as described above for hydrocarbon reverse osmosis (and/or forward osmosis). Examples of suitable feed pressures for a hydrocarbonaceous compound/inorganic compound reverse osmosis separation can be at least about 10 barg (1.0 MPag), or at least about 15 barg (~1.5 MPag), or at least about 20 barg (~2.0 MPag), or at least about 25 barg (~2.5 MPag), or at least about 30 barg (3.0 MPag), or at least about 35 barg (3.5 MPag), or at least about 40 barg (4.0 MPag), or at least about 50 barg (5.0 MPag), and/or up to about 200 barg (20 MPag) or less, or about 170 barg (17 MPag) or less, or about 150 barg (15 MPag) or less. In particular, the feed pressure can be about 15 barg (~1.5 MPag) to about 200 barg (~20 MPag), or about 40 barg (~4.0 MPag) to about 200 barg (~20 MPag), or about 50 barg (~5.0 MPag) to about 150 barg (~15 MPag). The separation can be performed to result in a permeate that is enriched in either the hydrocarbonaceous compound or the inorganic compound, depending on the relative molecular sizes of the compounds.

Applications for Carbon Membrane Separations

A variety of hydrocarbon separations can potentially be performed as hydrocarbon reverse osmosis separations as described herein. Examples of potential separations include, but are not limited to:

1) Separation of para-xylene from o-xylene and m-xylene. As described below, para-xylene has a molecular diameter of about 5.8 Angstroms, while o-xylene and m-xylene have diameters of about 6.8 Angstroms. Membranes having a selective layer with a smallest substantial pore size between these molecular diameter values, such as a smallest substantial pore size of about 6.0 Angstroms to about 6.5 Angstroms, or about 6.0 Angstroms to about 7.0 Angstroms, or about 6.0 Angstroms to about 6.8 Angstroms, can be used for this type of separation.

2) Separation of para-xylene from para-diethylbenzene. In simulated moving bed separators for separation of para-xylene from other $C_8$ compounds, para-diethylbenzene is used to displace para-xylene in the bed during desorption. While this separation can be performed by distillation, a reverse osmosis separation can allow for recovery of additional p-xylene from the para-diethylbenzene desorbent. Para-xylene has a molecular diameter of about 5.8 Angstroms, while para-diethylbenzene has a molecular diameter of about 6.7 Angstroms. Membranes having a selective layer with a smallest substantial pore size between these molecular diameter values, such as a smallest substantial pore size of about 6.0 Angstroms to about 7.0 Angstroms (or about 6.0 Angstroms to about 6.8 Angstroms) can be used for this type of separation.

3) Branched paraffins versus linear paraffins and single-branched paraffins from multi-branched paraffins. For example, 2,2,4-trimethyl pentane (a relatively high octane value compounds) can be separated from isobutane, or other hydrocarbon streams. 2,2,4-trimethyl pentane can correspond to a desired product from an alkylation reaction for producing alkylated gasoline. In order to drive the reaction, an alkylation reaction can often be performed using an excess of isobutane. Conventional methods for separating 2,2,4-trimethyl pentane and/or other desired alkylated gasoline products from the alkylation reactants can involve energy intensive distillation columns. Instead, a membrane separation as described herein can allow for separation of alkylated gasoline products from the alkylation reactants based on molecular diameter. As another example, isobutane can be separated from paraffin or olefin containing streams. The membrane for separation of branched from linear paraffins, or single-branch from multi-branched paraffins, can be selected based on the relative sizes of the compounds. As examples of potential separations, 2,2,4-trimethyl pentane has a molecular diameter of about 6.3 Angstroms. Isobutane has a molecular diameter of about 4.9 Angstroms. Several small n-paraffins, such as n-heptane and n-butane, can have a molecular diameter of about 4.3 Angstroms. For separations of 2,2,4-trimethyl pentatne from isobutane, a selective layer with a smallest substantial pore size roughly between these molecular diameter values, such as a smallest substantial pore size of about 5.1 Angstroms to about 6.6 Angstroms (or about 5.1 Angstroms to about 6.4 Angstroms) can be suitable. For separations of branched paraffins such as isobutane from small n-paraffins such as n-butane, a selective layer with a smallest substantial pore size of about 4.5 Angstroms to about 5.2 Angstroms (or about 4.5 Angstroms to about 5.0 Angstroms) can be suitable.

4) Separation of n-heptane (or other $C_4$-$C_{10}$ n-paraffins) from toluene. The octane value of small n-paraffins ($C_4$-$C_{10}$) can be relatively low in comparison to other similar sized hydrocarbons, such as toluene. Single ring aromatic structures such as toluene can often have a molecular diameter of about 5.8 Angstroms or greater. Thus, a selective layer with a smallest substantial pore size of about 4.5 Angstroms to about 6.1 Angstroms (or about 4.5 Angstroms to about 5.9 Angstroms) can be suitable for separating small n-paraffins from various single ring aromatics.

5) Separation of $C_4$-$C_8$ paraffins or olefins from $C_{10}$-$C_{20}$ paraffins or olefins. As the chain length of aliphatic hydrocarbons increases, the molecular size starts to increase due to the larger hydrocarbons primarily being in conformations other than a relatively straight chain.

6) Ethanol from various gasoline components. Although ethanol contains a heteroatom (oxygen), it is a hydrocarbonaceous compound that can be separated according to the reverse osmosis methods described herein. When used as a fuel, ethanol can correspond to a relatively high octane component. Separating ethanol from other gasoline components can allow for selective separation of a high octane portion of gasoline. This can allow, for example, creation of a reservoir of higher octane fuel that can be delivered on demand to a high compression ratio engine. Ethanol has a molecular diameter of about 4.5 Angstroms. Ethanol can be separated from larger, lower octane value components (such as single ring aromatics) using a selective layer with a smallest substantial pore size of about 4.7 Angstroms to about 6.1 Angstroms (or about 4.7 Angstroms to about 5.9 Angstroms). During this type of separation, some other small molecular diameter components of gasoline may also be separated out along with the ethanol.

7) Separation of branched olefins from hydrocarbon mixtures. In this type of separation the branched olefins are the retentate and linear parafins and/or linear olefins flow to the permeate.

8) Separation of olefin/paraffin mixtures. Linear olefin/paraffin mixtures such as ethane/ethylene, or propane/propylene, or n-butane/n-butylene can be separated by hydrocarbon reverse osmosis. The selectivity in the separation can come from the differences in the kinetic diameters of the molecules, which is approximately 0.5 Angstroms. At sufficient pressure and low enough temperature these mixtures can be. With membranes having pore sizes between 3.2 and 4.2 angstroms linear olefins can be selectively permeated through the membrane in preference to a linear paraffin.

9) Separation of ketones from hydrocarbon mixtures. Ketones are industrially produced and have uses as solvents, polymer precursors, and pharmaceuticals. Some of the industrially used and/or important ketones are acetone, methylethyl ketone, and cyclohexanone. Industrially the most important common production technique involves oxidation of hydrocarbons, often with air. For example, cyclohexanone can be produced by aerobic oxidation of cyclohexane. After forming cyclohexanone, the cyclohexanone product (larger kinetic diameter) can be separated from cyclohexane (smaller kinetic diameter) using a suitable membrane. As another example, acetone can be prepared by air-oxidation of cumene that is formed from alkylation of benzene with propylene. In some aspects, membrane formulations and processes as described herein can purify a cumene product by permeating propylene and benzene which are smaller than cumene. Membranes suitable for for xylene separation can also be suitable for separation of cumene from propylene and/or benzene. In some aspects, when cumene is oxidized to form acetone, the acetone can be separated from phenol (the other major product of cumene oxidation) using membranes and processes as described herein.

10) Separation of hydrocarbons alcohols, organic acids, and esters, from homogeneous catalysts. Hydroformylation is an example of a process that uses a homogeneous catalyst. Hydroformylation reactions involve the preparation of oxygenated organic compounds by the reaction of carbon monoxide and hydrogen (synthesis gas) with carbon compounds containing olefinic unsaturation. Water and organic soluble complexes of rhodium are among the most effective catalysts for hydroformylation. Homogeneous catalysts can be highly selective but conventionally have limited used in industrial processes because of problems associated with separation of homogeneous catalysts from product mixtures. For example, homogeneous rhodium catalysts can be used to catalyze hydroformylation reactions to produce aldehydes from alkenes. Ligated rhodium catalysts (for example rhodium ligated with triphenylphosphine) can selectively produce linear terminal aldehydes that in turn can be used to produce biodegradable detergents with approximately 12 carbons. When hydroformylation is performed on propene to produce butanal, the boiling points of propene and butanal are low enough that distillation can be used to separate homogeneous rhodium catalysts from the hydroformylation product mixture while reducing or minimizing the amount of catalyst degradation. However, for larger alkenes, distillation, phase equilibria, and crystallization processes that have been studied to separate the homogeneous rhodium catalyst from the product mixture either deactivate an unacceptable portion of the rhodium catalysts or lose too much of the rhodium in the product. In some aspects, membranes and processes as described herein can at least partially overcome this difficulty. When used in either a reverse osmosis or forward osmosis modality, membranes as described herein can separate a rhodium catalysts from the hydroformylation product. Membranes with pore sizes equal to that used for xylenes separation or as much as 2 Angstroms smaller can yield an appropriate size exclusion separation. More generally, such homogeneous catalysts can have effective molecular diameters of at least about 10 Angstroms, or possibly at least about 20 Angstroms or more. As a result, a selective layer with a smallest substantial pore size that is larger than the hydroformylation products (for example, greater than about 5.0 Angstroms) but smaller than about 10 Angstroms can be suitable for separating homogeneous catalysts from the reaction products. Afer separation, the homogeneous catalyst (such as the catalyst corresponding to the rhodium complexes) can be recycled back to the hydroformylation reactor. This can allow for catalyst losses of less than 0.01% per pass.

11) Refinery Alkylation: In refinery processing, isobutane can be alkylated with low-molecular-weight alkenes (primarily a mixture of propene and butene) in the presence of an acid catalyst such as sulfuric acid or hydrofluoric acid. Additionally or alternately, the acid catalyst can be in the form of a solid acid catalyst. A high ratio of isobutane to alkene at the point of reaction can reduce or minimize side reactions that can result in a lower octane product. A separation process can be used to facilitate providing a high ratio of isobutane to alkene at the point of reaction by allowing recycle of isobutane back to feed. In various aspects, a membrane as described herein can be used as part of a separation process to concentrate isobutane from refinery streams as a feed for the process and/or separate isobutane from the alkylation products (such as 2,2,4-trimethyl pentane) and/or or separate propylene and butane from olefin containing streams to provide feed for the alkylation unit. Additionally or alternately, membrane(s) as described herein can be used for separation and recovery of the acid catalyst. For example, for a process involving sulfuric acid as the catalyst, a first membrane separation can be performed to separate the hydrated sulfate ions and/or sulfuric acid from the larger hydrocarbons formed by the alkylation reaction. A second membrane can then be used can be used with a selective layer having a smallest substantial pore size that can allow water and the smaller hydrocarbons to pass through into a permeate while retaining the sulfate ions/ sulfuric acid in the retentate. This can allow for recovery of the acid catalyst into a recovered acid product having sufficient strength to act as a catalyst for alkylation.

12) IPA manufacture: The two main routes for isopropyl alcohol (IPA) production involve hydration of propylene. One of the routes is an indirect propylene hydration using sulfuric acid, while another route corresponds to direct hydration of propylene. Indirect propylene hydration using sulfuric acid can be performed using low-quality (i.e., low purity) propylene feeed. Direct hydration of propylene can benefit from having a higher purity propylene feed. After production of propylene, both processes can require some type of product separation process for separating isopropyl alcohol from water and other by-product(s). Separating isopropyl alcohol from other reaction products using distillation can be difficult because isopropyl alcohol and water form an azeotrope. In various aspects, membrane(s) as described herein can be used in separation processes for separation of isopropyl alcohol from water via a water reverse osmosis separation. In aspects involving the indirect process, separations can optionally also be used to reconstitute the sulfuric acid and control its acid strength in the production process.

13) Methanol Production: Crude methanol is produced in a catalytic reaction process from syngas (a mixture of CO, $CO_2$ and hydrogen). The membrane and processes described herein can provide a means of removing water from the crude methanol product.

14) MethylMethacrylate production: One of the commercial routes for MethylMethacrrylate (MMA) production involves direct oxidative esterification of methacrolein. The simplified chemical reaction for this route is:

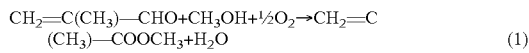

$$CH_2=C(CH_3)-CHO+CH_3OH+\tfrac{1}{2}O_2 \rightarrow CH_2=C(CH_3)-COOCH_3+H_2O \qquad (1)$$

In Equation (1), water is produced as a byproduct. The membranes/separation processes described herein can be used to remove water from the product stream to purify the MethylMethacrylate product. This can be beneficial, as a membrane separation process can reduce or minimize the need for separating the reaction products from water and/ methanol via distillation. Distillation processes can have difficulties in separating methanol and/or water from the methylmethacrylate products due to, for example, various azeotropes that may form. Another commercial route can involve a direct oxidation method corresponding to a two-step oxidation of isobutylene or tert-butyl alcohol with air to produce methacrylic acid, followed by esterification with methanol to produce MMA. The simplified chemistry of this route is:

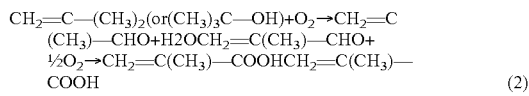

$$CH_2=C-(CH_3)_2(\text{or}(CH_3)_3C-OH)+O_2 \rightarrow CH_2=C(CH_3)-CHO+H2OCH_2=C(CH_3)-CHO+\tfrac{1}{2}O_2 \rightarrow CH_2=C(CH_3)-COOHCH_2=C(CH_3)-COOH \qquad (2)$$

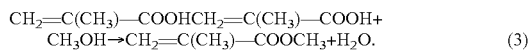

$$CH_2=C(CH_3)-COOHCH_2=C(CH_3)-COOH+CH_3OH \rightarrow CH_2=C(CH_3)-COOCH_3+H_2O. \qquad (3)$$

Again, water is produced as a byproduct in Equation (3). The membranes and/or processes described herein can be used to remove water from the product stream to purify the MethylMethacrylate product while avoiding the difficulties of attempting to use distillation to separate compounds that form azeotropes.

15) Sulfuric acid concentration: Sulfuric acid can be regenerated from about 70 wt % $H_2SO_4$ to about 85 wt % or about 96 wt % sulfuric acid by using membranes and/or processes as described herein to remove acid soluble oils (ASO) from the acid. The acid soluble oils are believed to correspond to high molecular weight products formed due to side reactions during alkylation. The acid soluble oils can correspond to larger molecular diameter compounds relative to sulfuric acid and/or hydrated ions formed by sulfuric acid. As described herein, membranes with smallest substantial pore sizes of at least about 5.0 Angstroms and/or about 10 Angstroms or less can be suitable for separating sulfuric acid from acid soluble oils.

Hydrocarbon Forward Osmosis

An asymmetric membrane as described herein can be used for performing membrane separations based on hydrocarbon forward osmosis. Hydrocarbon forward osmosis generally refers to a selective membrane separation where a separation is performed on hydrocarbon liquid containing at least two hydrocarbon and/or hydrocarbonaceous components and a draw stream of a molecular species or a mixture of molecular species is used that sweeps the permeate side of the membrane. This draw species or mixture of molecular species will be referred to herein as a draw solvent. The draw solvent is flowed on the permeate side of the membrane either co-currently or counter-currently to the feed. Generally it is preferred to flow the draw solvent counter-currently to the feed.

In various aspects, a forward osmosis process can be executed such that the hydrocarbon and/or hydrocarbonaceous components being separated are in the liquid phase in both the feed and permeate for at least one point along the length of the membrane. In one mode of operation the hydrocarbon or hydrocarbonaceous species being separated are in the liquid phase of the feed being introduced into the membrane module and at least one of the species being separated is predominantly in the liquid phase of the permeate being drawn out of the membrane module. The draw solvent can be in either the liquid or gaseous phase. As defined herein, a forward osmosis process is run such that for at least one position along the length of the membrane, the molecules being separated are in the liquid phase in both the feed and permeate.

In selective hydrocarbon forward osmosis, the liquid phase mole fraction determined on a draw solvent free basis of at least one component is greater in the permeate than in the feed. On a draw solvent free basis, in some aspects the mole fraction of this component in the liquid phase can be at least 200% greater in the permeate when the molar concentration in the feed is in a range from 0.1% to 10%, 100% greater in the permeate when the molar concentration in the feed is in a range from 10% to 20%, 75% greater in the permeate when the molar concentration in the feed is in a range from 20% to 40%, 50% greater in the permeate when the molar concentration in the feed is in a range from 40% to 60%, 20% greater in the permeate when the molar concentration in the feed is in a range from 60% to 80%, and 10% greater in the permeate when the molar concentration in the feed is in a range from 80% to 90%. Preferably, the mole fraction of this component in the liquid phase can be at least 500% greater in the permeate when the molar concentration in the feed is in a range from 0.1% to 10%, and 250% greater in the permeate when the molar concentration in the feed is in a range from 10% to 20%.

Another metric for membrane performance can be the selectivity of a membrane for a pair of hydrocarbon or hydrocarbonaceous components in the feed. In various aspects, the membrane can be operated in a forward osmosis process such that there is at least one pair of hydrocarbon or hydrocarbonaceous components for which the selectivity is at least 2, or at least 5, or at least 10, or at least 20, or at least 40, or at least 100. This can be achieved using a membrane a) that has a pore size in a range that can separate molecules A and B, b) that has a low defect density, and c) that can be operated with a transmembrane pressure sufficiently high to provide thermodynamic drive for selective permeation. Transmembrane pressures can be at least about 10 bar, or at least about 20 bar, or at least about 50 bar, or at least about 100 bar. Optionally but preferably, the flow rate of the feed across the membrane can be fast enough so that a selective separation will occur at a reasonable commercial time scale.

For hydrocarbon forward osmosis, the feed can flow over the membrane at a pressure at least 2 bars greater than the pressure at which the permeate is drawn off. Preferably the feed can be at a pressure at least 5 bars greater than the permeate pressure, or at least 10 bars greater than the permeate pressure, or at least 50 bars greater than the permeate pressure, or at least 100 bars greater than the permeate pressure, or at least 200 bars greater than the permeate pressure. It is preferable that the flux of the molecular species being selectively transported through the membrane can increase as the transmembrane pressure (pressure difference between the feed and permeate) increases from 2 bar to 5 bar or 2 bar to 10 bar, or 2 bar to 20 bar, or 2 bar to 100 bar.

Pressure in the permeate can be sufficient so that the hydrocarbon species are in the liquid phase for at least one point along the permeate side of the membrane. Permeate pressure can be 0.25 bara or greater. In some aspects, the permeate pressure can be in a range from 1 to 5 bara. This can reduce, minimize, or eliminate the need for a vacuum on the permeate side of the membrane.

In various aspects, the temperature for a hydrocarbon forward osmosis separation can be any convenient temperature from about 0° C. to about 300° C. The temperature for a given separation can be dependent on the nature of permeate component and the nature of the retentate. Depending on the aspect, the separation temperature can be about 0° C. to about 100° C., or about 50° C. to about 150° C., or about 100° C. to about 200° C., or about 150° C. to about 250° C., or about 200° C. to about 300° C. Alternatively, the separation temperature can be at least about 0° C., or at least about 25° C., or at least about 50° C., or at least about 75° C., or at least about 100° C., or at least about 125° C., or at least about 150° C., or at least about 175° C., or at least about 200° C., and/or about 300° C. or less, or about 275° C. or less, or about 250° C. or less, or about 225° C. or less, or about 200° C. or less, or about 175° C. or less, or about 150° C. or less, or about 125° C. or less, or about 100° C. or less.

Hydrocarbon Pressurized Pervaporation and Pressurized Vapor Perstraction

An asymmetric membrane as described herein can be used for performing membrane separations based on hydrocarbon pressurized pervaporation or pressurized vapor perstraction. Hydrocarbon pressurized pervaporation or hydrocarbon pressurized vapor perstraction generally refers to a selective membrane separation where a separation is performed on pressurized hydrocarbon liquid feed containing at least two hydrocarbon and/or hydrocarbonaceous components. Feed pressure can be greater than 1.25 bara, or greater than 5 bara, or greater than 10 bara, or greater than 20 bara, or greater than 100 bara. It is preferable that the flux of the molecular species being selectively transported through the membrane increase as the feed pressure increases from 5 bara to 10 bara, or 10 bara to 20 bara, or 20 bara to 100 bara. In both hydrocarbon pressurized pervaporation or hydrocarbon pressurized vapor perstraction, the hydrocarbon or hydrocarbonaceous species being separated are predominantly in the vapor phase for a least one point along the permeate side of the membrane. Permeate pressures can be in a range from 0.1 to 10 bara depending on the temperature at which the process is run. The temperature for a given separation can be dependent on the nature of permeate and the nature of the retentate. Depending on the aspect, the separation temperature can be about 0° C. to about 100° C., or about 50° C. to about 150° C., or about 100° C. to about 200° C., or about 150° C. to about 250° C., or about 200° C. to about 300° C. It is necessary to operate the process at a temperature sufficiently high to produce a vapor phase on the permeate side.

Hydrocarbon pressurized vapor pervaporation can be performed without a draw solvent and hydrocarbon pressurized vapor perstraction can be performed with the aid of a draw solution that can be introduced in either the gas or liquid phase. Generally the draw solvent is introduced on the permeate side of the membrane.

In selective hydrocarbon pressurized vapor perstraction or selective hydrocarbon pressurized pervaporation the mole fraction determined on a draw solvent free basis of at least one component is greater in the permeate than in the feed. On a draw solvent free basis, in some aspects the mole fraction of this component can be at least 200% greater in the permeate when the molar concentration in the feed is in a range from 0.1% to 10%, 100% greater in the permeate when the molar concentration in the feed is in a range from 10% to 20%, 75% greater in the permeate when the molar concentration in the feed is in a range from 20% to 40%, 50% greater in the permeate when the molar concentration in the feed is in a range from 40% to 60%, 20% greater in the permeate when the molar concentration in the feed is in a range from 60% to 80%, and 10% greater in the permeate when the molar concentration in the feed is in a range from 80% to 90%. In a preferred aspect the mole fraction of this component can be at least 500% greater in the permeate when the molar concentration in the feed is in a range from 0.1% to 10% and 250% greater in the permeate when the molar concentration in the feed is in a range from 10% to 20%.

Another metric for membrane performance can be the selectivity of a pair of hydrocarbon and/or hydrocarbonaceous components in the feed. It is preferred that the membrane be operated in a hydrocarbon pressurized pervaporation or pressurized vapor perstraction process such that there is at least one pair of hydrocarbon or hydrocarbonaceous for which the selectivity is greater than 2, or 5, or 10, or 20, or 40, or 100. This can be achieved using a membrane a) that has a pore size in a range that can separate molecules A and B, b) that has a low defect density, and c) that can be operated with a transmembrane pressure sufficiently high to provide thermodynamic drive for selective permeation. Transmembrane pressures can be at least about 10 bar, or at least about 20 bar, or at least about 50 bar, or at least about 100 bar. Optionally but preferably, the flow rate of the feed across the membrane can be fast enough so that a selective separation will occur at a reasonable commercial time scale.

Other Operational Modalities

Those skilled in the art can design processes that provide combinations of hydrocarbon reverse osmosis, hydrocarbon forward osmosis, hydrocarbon pressurized pervaporation and/or hydrocarbon pressurized vapor perstraction in any convenient manner.

Configuration Example: Xylene Separations

FIGS. 1 to 4 schematically show an example of how a xylene separation/purification loop can be modified using membrane structures as described herein. FIG. 1 shows an example of a typical para-xylene recovery loop. In FIG. 1, an input stream 110 comprising a mixture of $C_{8+}$ aromatics is passed into a distillation column 120 for separation of higher boiling point compounds 125 (i.e., $C_{9+}$) from $C_8$ compounds 123. A $C_{8+}$ isomerate stream 145 can be added to input stream 110 prior to introduction into distillation column 120. It is noted that the stream of $C_8$ compounds 123 typically includes ethylbenzene. Stream of $C_8$ compounds 123 is then passed into a para-xylene recovery unit 130 for separation into a higher purity para-xylene stream 133 and a raffinate or filtrate 135 that is depleted in para-xylene. Para-xylene recovery unit 130 can be, for example, a simulated moving bed separator. The raffinate 135 can be introduced into isomerization unit 140 for conversion of ortho- and meta-xylene into the desired para-xylene product. Isomerization unit can also receive a hydrogen input stream 141 and generate additional side products of benzene/toluene stream 147 and light gas 149. During this process, if ethylbenzene is present in the raffinate 135, additional $C_{9+}$ compounds can be made. As a result, the $C_{8+}$ isomerate stream 145 generated by isomerization unit 140 can be distilled in distillation column 120 prior to introduction into para-xylene recovery unit 130.

Figure 2:
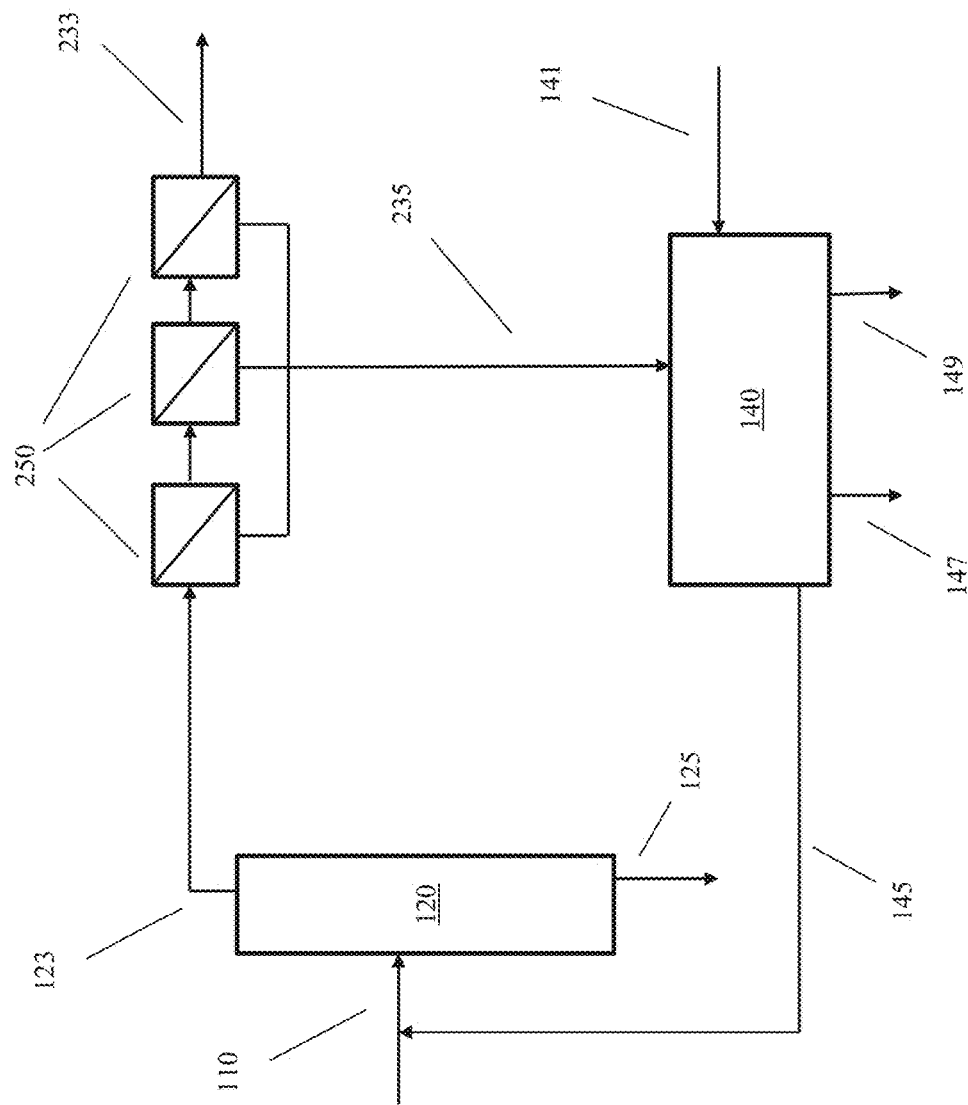
FIG. 2 schematically shows a process configuration including a hydrocarbon reverse osmosis membrane for separation a stream of higher purity para-xylene from a mixed aromatic input stream.

Use of hydrocarbon reverse osmosis membranes can allow for several types of improvements in a configuration for para-xylene separation. FIG. 2 shows an example of one type of improvement. In FIG. 2, the para-xylene recovery unit 130 from FIG. 1 has been replaced with a series of hydrocarbon reverse osmosis membranes 250. In FIG. 2, the raffinate 235 corresponds to a combined raffinate from the reverse osmosis membranes 250, while the higher purity para-xylene stream 233 corresponds to the permeate from the final reverse osmosis membrane 250. Optionally, a single reverse osmosis membrane 250 can be sufficient for achieving a desired purity for higher purity para-xylene stream 233. The high permeation rates and para-xylene selectivity that can be achieved using hydrocarbon reverse osmosis membranes can allow a membrane separation to provide commercial purification rates and/or can reduce or minimize the number of separation stages or units that needed for purification.

Figure 3:
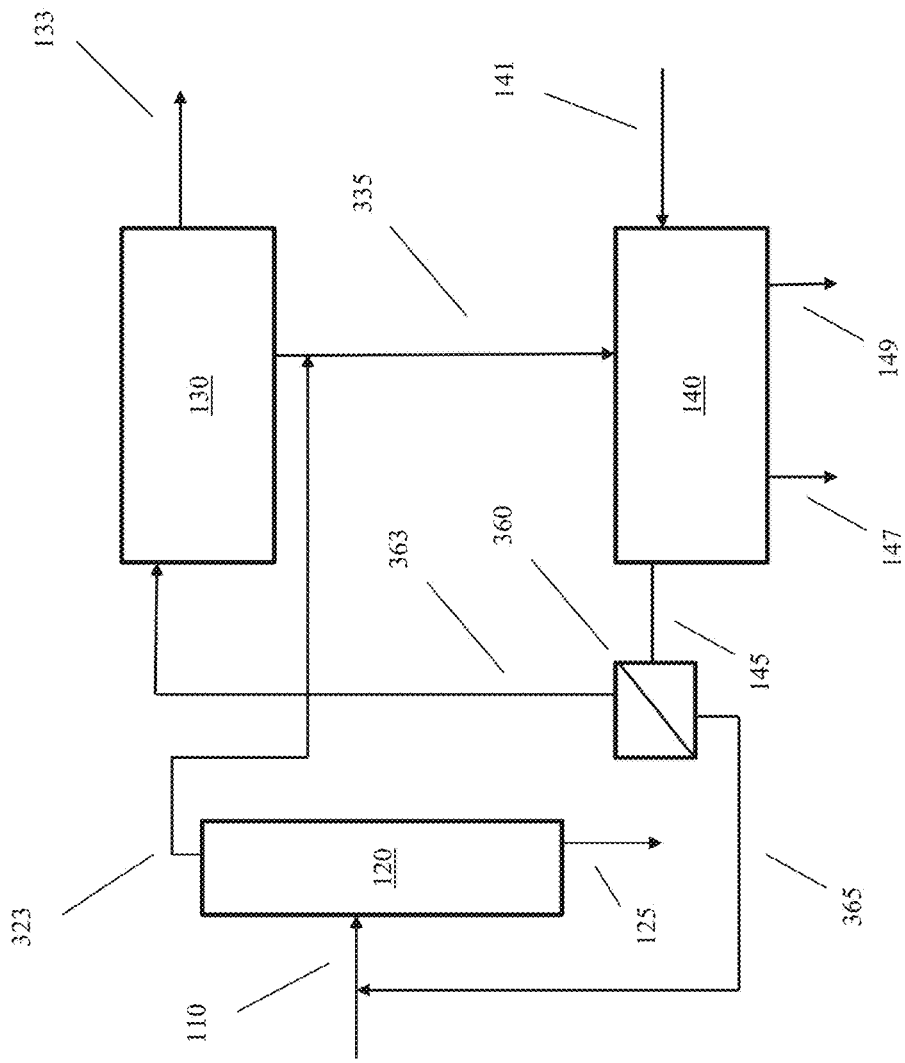
FIG. 3 schematically shows a process configuration including a hydrocarbon reverse osmosis membrane for separation a stream of higher purity para-xylene from a mixed aromatic input stream.

FIG. 3 shows another variation where a hydrocarbon reverse osmosis membrane 360 is used to separate the $C_{8+}$ isomerate stream 145 from isomerization unit 140. This can allow for production of a para-xylene enriched stream 363 and a para-xylene lean $C_{8+}$ stream 365 that can be returned to the distillation column. In the configuration shown in FIG. 3, the addition of para-xylene lean $C_{8+}$ stream 365 into the input stream 110 results in a combined stream that is lower in para-xylene content. As a result, the $C_8$ stream 323 from distillation column 120 can be introduced into isomerization unit 140 along with raffinate 335. The para-xylene enriched stream 363 from hydrocarbon reverse osmosis membrane 360 is the stream passed into para-xylene recovery unit 130 for formation of a para-xylene enriched product 133.

Figure 4:
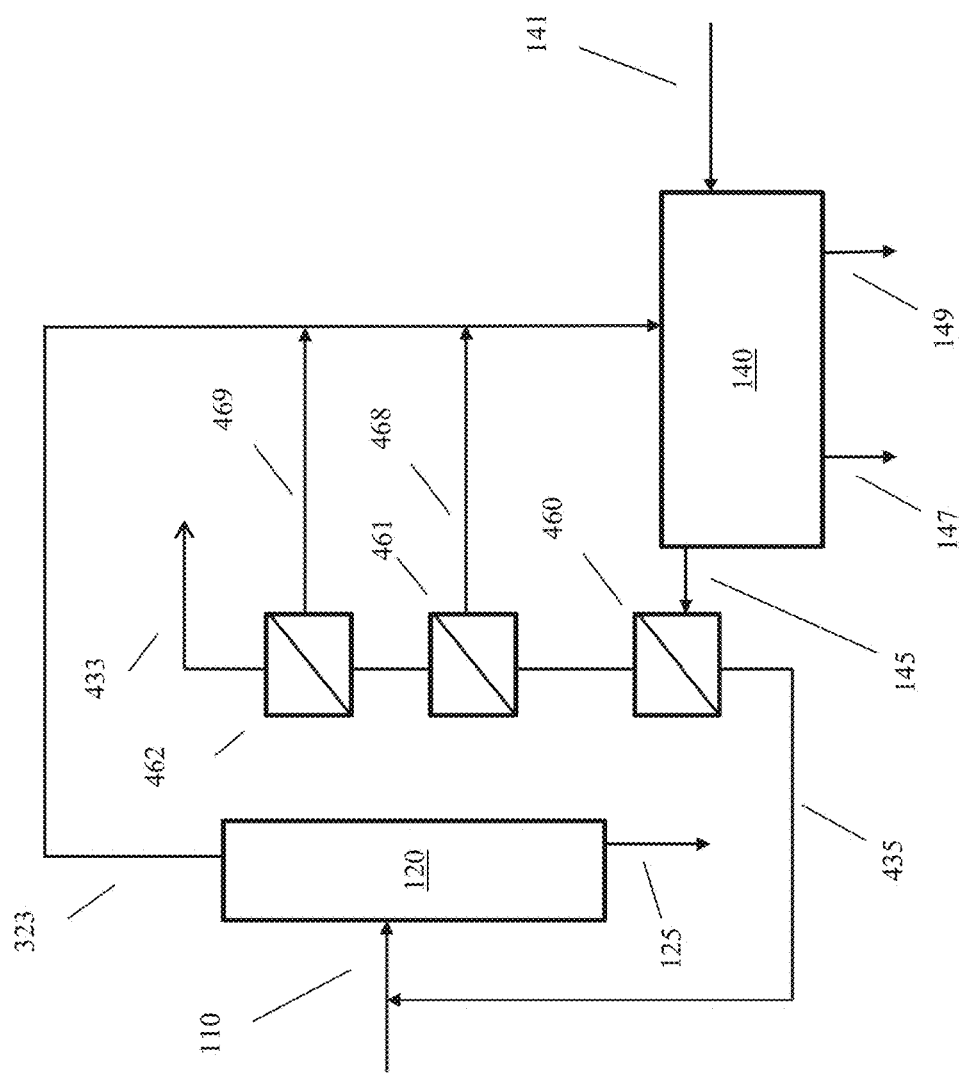
FIG. 4 schematically shows a process configuration including a hydrocarbon reverse osmosis membrane for separation a stream of higher purity para-xylene from a mixed aromatic input stream.

FIG. 4 shows still another variation where the features of FIGS. 2 and 3 are combined. In FIG. 4, the $C_{8+}$ isomerate stream 145 is passed through a series of hydrocarbon reverse osmosis membranes, such as hydrocarbon reverse osmosis membranes 460, 461, and 462. The use of a plurality of hydrocarbon reverse osmosis membranes can allow for production of a higher purity para-xylene stream 433 while potentially eliminating the need for a separate para-xylene recovery unit. In FIG. 4, the retentate streams 468 and 469 from reverse osmosis membranes 461 and 462 are returned to the isomerization unit 140 along with the $C_8$ stream 323 from distillation column 120. The retentate 435 from reverse osmosis membrane 460 is returned to the distillation column 120.

Example—Characterization of PVDF Hollow Fiber Membrane Structures

Hollow fiber asymmetric membrane structures were formed by using a co-annular spinneret with two types of PVDF solutions as described above. Polymer solutions comprising solvent, non-solvent, and polymer were prepared. For the core polymer solution, dimethylacetamide (DMAc) was used as a solvent and mixture of lithium chloride (LiCl) and water were used as non-solvents. For the sheath polymer solution, a mixture of dimethylacetamide and tetrahydrofuran were used as solvents and ethanol was used as a non-solvent. For both core and sheath polymer solutions, poly(vinylidene) fluoride was used as a polymer source. Asymmetric double layer hollow fibers were created via nonsolvent phase inversion technique. The aforementioned polymer solutions were extruded through a spinneret into a non-solvent quench bath and further taken-up on a spinning drum at desired speed.

After formation of hollow fiber structures, some hollow fiber structures were pyrolyzed without prior cross-linking. Other hollow fiber structures were exposed to cross-linking and then pyrolyzed.

Figure 5:
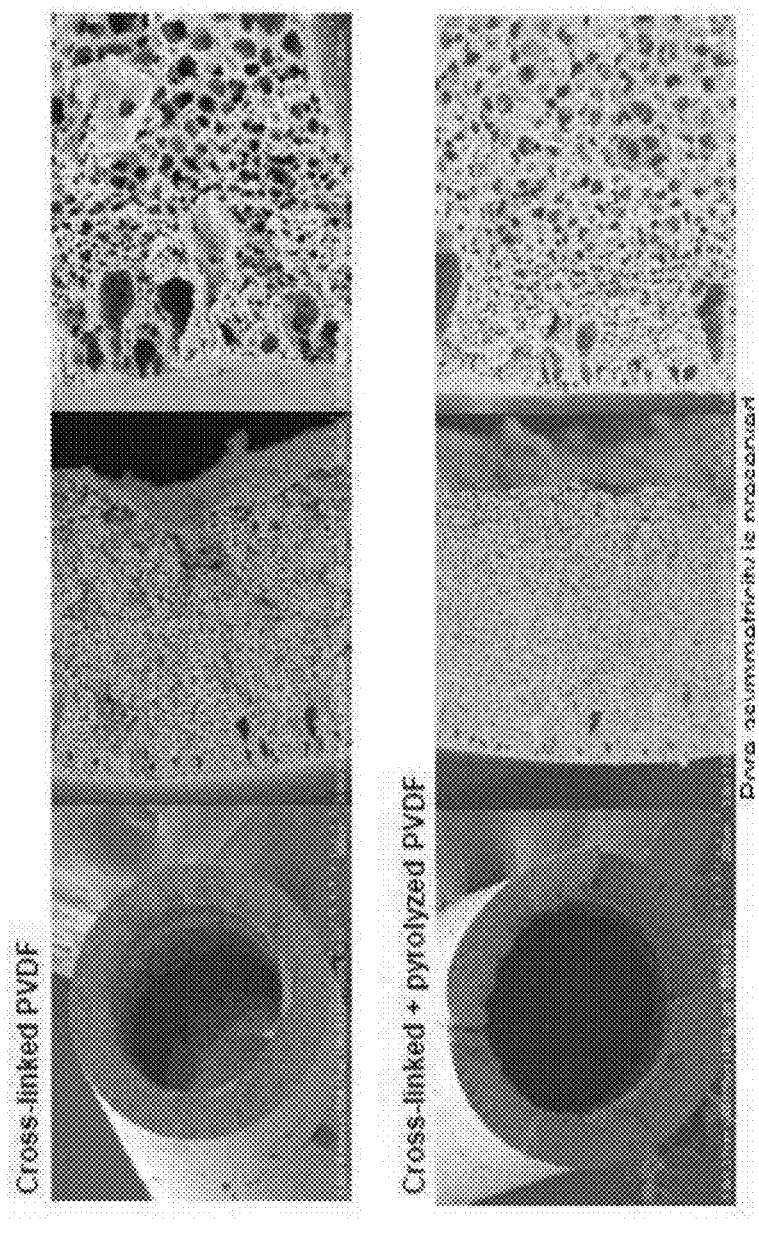
FIG. 5 shows examples of asymmetric membrane structures.

FIG. 5 shows SEM micrographs of hollow fiber structures that were either cross-linked (top series) or cross-linked and then pyrolyzed at 550° C. in an argon atmosphere (bottom series). As shown in FIG. 5, the porous nature of the core portion of the hollow fiber structure is retained in the final hollow fiber membrane structure after pyrolysis. This allows the asymmetric structure (dense sheath, porous core) original present in the hollow fiber structure to be preserved after pyrolysis is used to form the hollow fiber membrane structure.

Figure 6:
FIG. 6 shows examples of a membrane structure formed from non-cross-linked polyvinylidene fluoride before and after pyrolysis.
Figure 6:
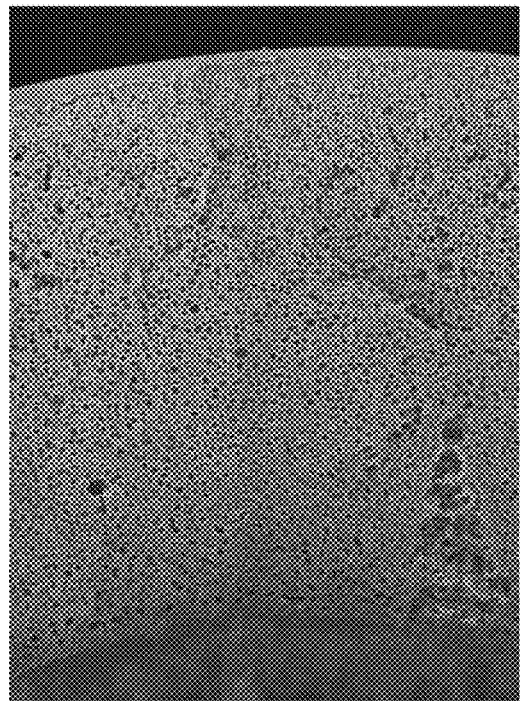

The preserved asymmetric membrane structure shown in FIG. 5 is in contrast to the structure shown in the SEM micrographs in FIG. 6, which shows a hollow fiber structure before and after pyrolysis when cross-linking is not used. In the left micrograph, the hollow fiber structure is shown prior to pyrolysis. The difference in porosity between the outer sheath layer and the porous core is visible in the micrograph. The right micrograph shows the structure after pyrolysis. Because cross-linking was not performed, the pore structure in the core has collapsed, resulting in a symmetric dense structure throughout.

Figure 16:
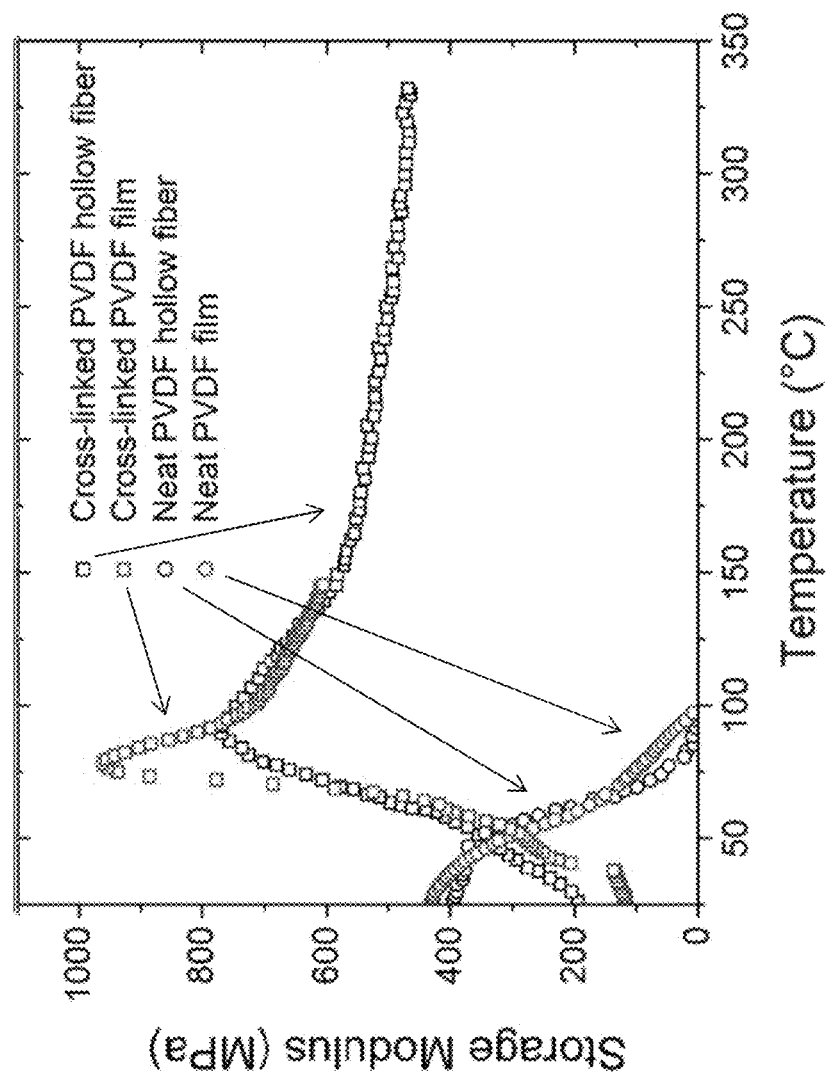
FIG. 16 shows storage modulus values for polyvinylidene fluoride membrane structures with and without cross-linking.

FIG. 16 provides additional details regarding the impact of cross-linking the PVDF structure prior to pyrolysis. FIG. 16 shows the structural modulus of flat and hollow fiber structures during a pyrolysis process for both cross-linked and non-cross-linked structures. As shown in FIG. 16, the PVDF structures that were not cross-linked prior to pyrolysis actually have a higher initial structural modulus value. However, heating the non-cross-linked structures quickly reduces the structural modulus, until the structural modulus reaches zero at a temperature of about 100° C. At a structural modulus of zero, the PVDF structure acquires fluid-like properties. This loss of structural modulus is believed to correspond with the loss of porosity for the core when cross-linking is not performed prior to pyrolysis. By contrast, the cross-linked structures achieve a maximum structural modulus at temperatures near 100° C. Further heating of the cross-linked structures results in structural modulus values that asymptotically approach about 500 MPa.

Figure 7:
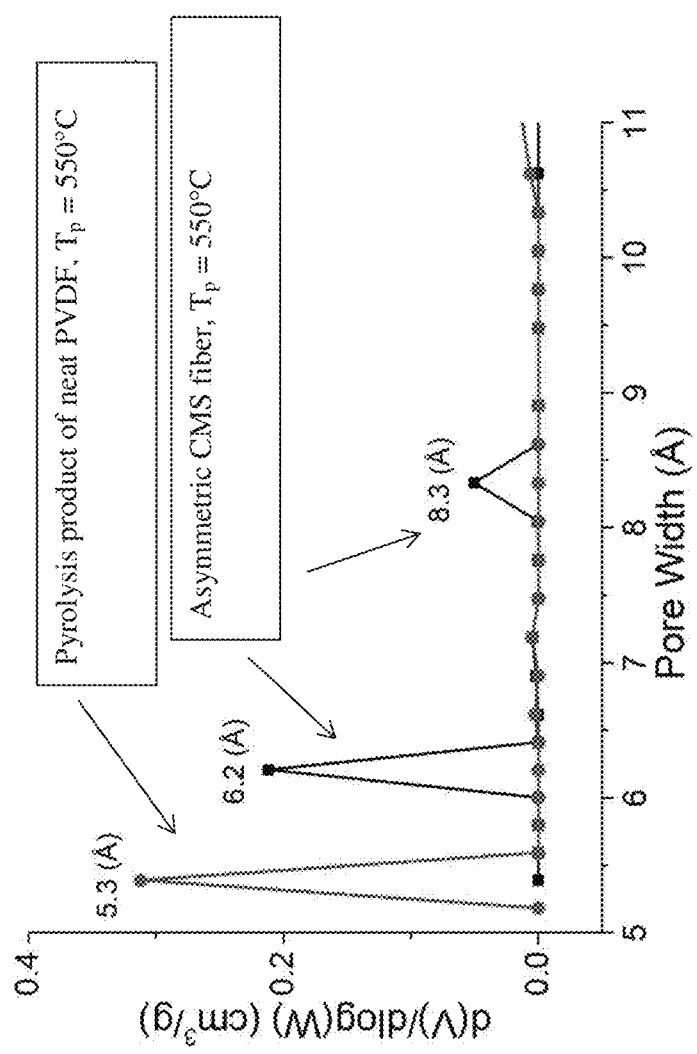
FIG. 7 schematically shows examples of pore size distributions for porous carbon membrane structures formed by pyrolysis of polyvinylidene fluoride membrane structures with and without prior cross-linking.

The use of cross-linking prior to pyrolysis also impacts the nature of the amorphous pore structure formed in the sheath layer. FIG. 7 shows the pore size distribution (alternatively referred to here as pore width) for the sheath layer after pyrolysis for hollow fiber membrane structures formed with and without cross-linking. The pore size distribution in FIG. 7 was derived from nitrogen physisorption (BET). As shown in FIG. 7, when pyrolysis was performed on the PVDF hollow fiber structure without prior cross-linking, the resulting sheath layer had a unimodal pore size distribution with a median size of about 5.2 Angstroms. When pyrolysis was performed after cross-linking, the resulting sheath layer had a bimodal pore distribution, with median pore sizes of 6.3 Angstroms and 8.2 Angstroms. Thus, cross-linking of the hollow fiber structure provides multiple benefits. In addition to maintaining the asymmetric nature of the structure after pyrolysis as shown in FIG. 5, performing cross-linking prior to pyrolysis also increases the median pore size for the smallest pore size peak in the pore size distribution.

Figure 8:
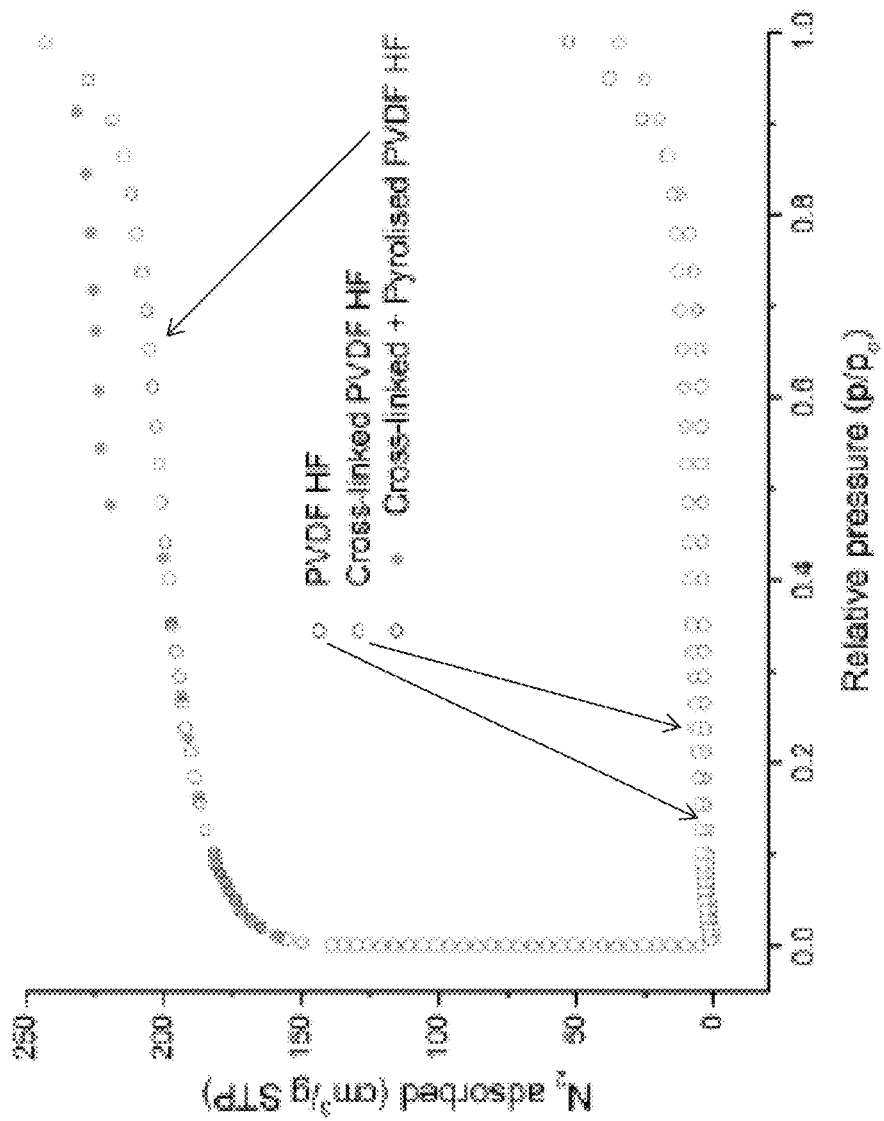
FIG. 8 shows examples of $N_2$ physisorption on polyvinylidene fluoride and porous carbon membrane structures.

FIG. 8 shows nitrogen physisorption data for the sheath layer of a hollow fiber structure as formed, the structure after cross-linking, and the structure after cross-linking and pyrolysis. As shown in FIG. 8, the sheath layer has a minimal surface area when initially formed. Cross-linking may slightly increase the surface area, but otherwise the surface area of the cross-linked surface appears to be similar to the surface area of the surface when initially formed. Based on the surface area values of less than 50 cm$^2$/g, both the sheath as formed and the sheath after cross-linking have a minimal amount of pore structure. By contrast, after cross-linking and pyrolysis the sheath layer has a surface area of greater than 700 cm$^2$/g. This indicates the pyrolysis causes formation of a substantial pore structure.

Figure 9:
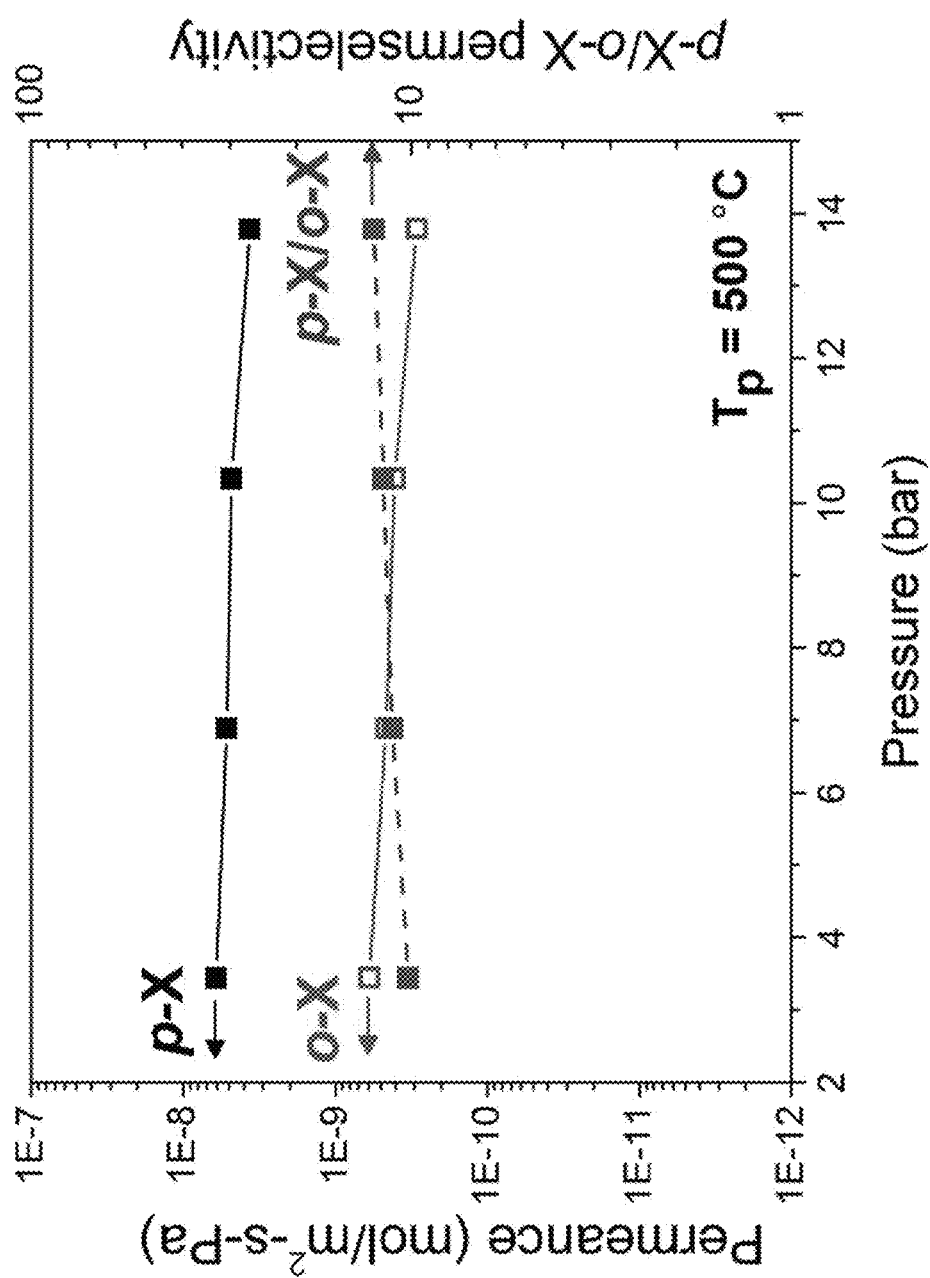
FIG. 9 shows single component permeance values for various single ring aromatic compounds with respect to an asymmetric porous carbon membrane structure.
Figure 10:
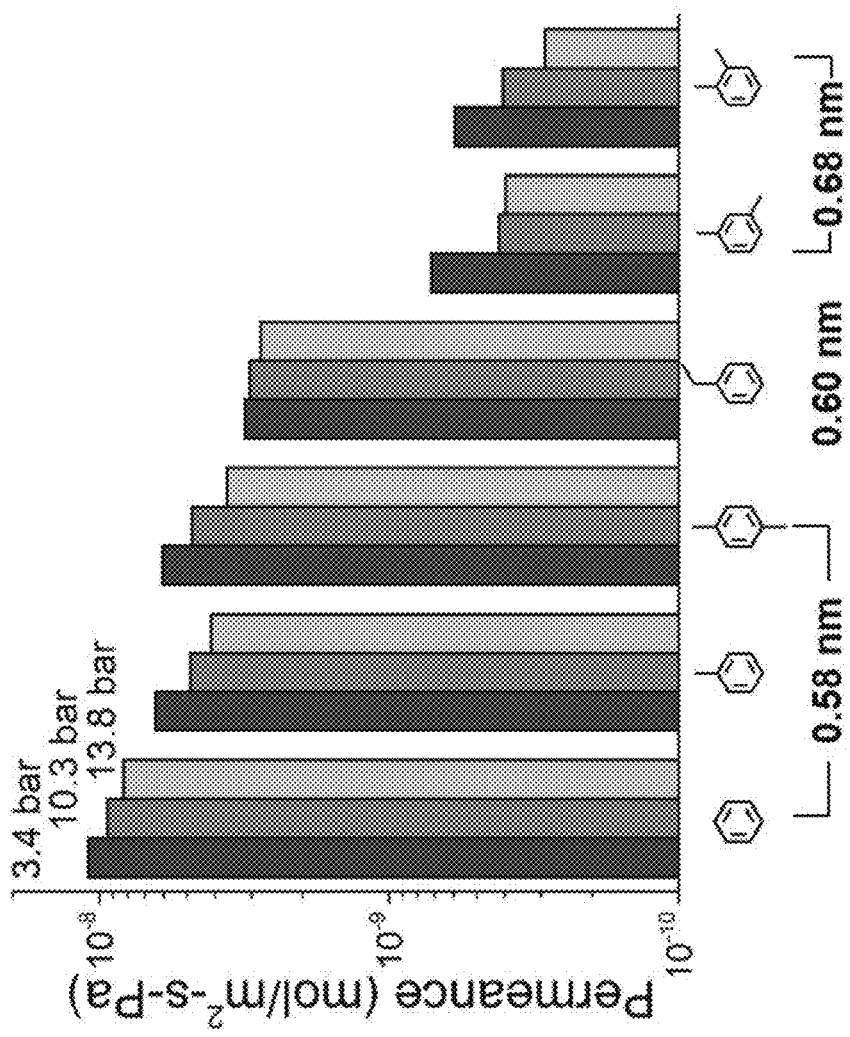
FIG. 10 shows single component permeance values for various single ring aromatic compounds with respect to an asymmetric porous carbon membrane structure.

The substantial pore network formed after cross-linking and pyrolysis of the PVDF hollow fiber structure can be used for hydrocarbon reverse osmosis separation of molecules. Suitable molecules for separation can have appropriate sizes relative to the 6.2 Angstrom smallest median pore size of the pore network. FIG. 9 shows an example of single compound permeation flux for para-xylene (5.8 Angstroms) and ortho-xylene (6.8 Angstroms) as a function of pressure. FIG. 9 also shows the expected relative selectivity based on the single compound permeation values. As shown in FIG. 9, the expected or ideal selectivity increases as the feed pressure to the membrane increases. FIG. 10 shows permeance values for the additional compounds benzene, toluene, and ethylbenzene. As shown in FIG. 10, para-xylene has a comparable permeance value to toluene and ethylbenzene. This is in contrast to the higher permeance for benzene and the lower permeance for ortho-xylene.

Figure 11:
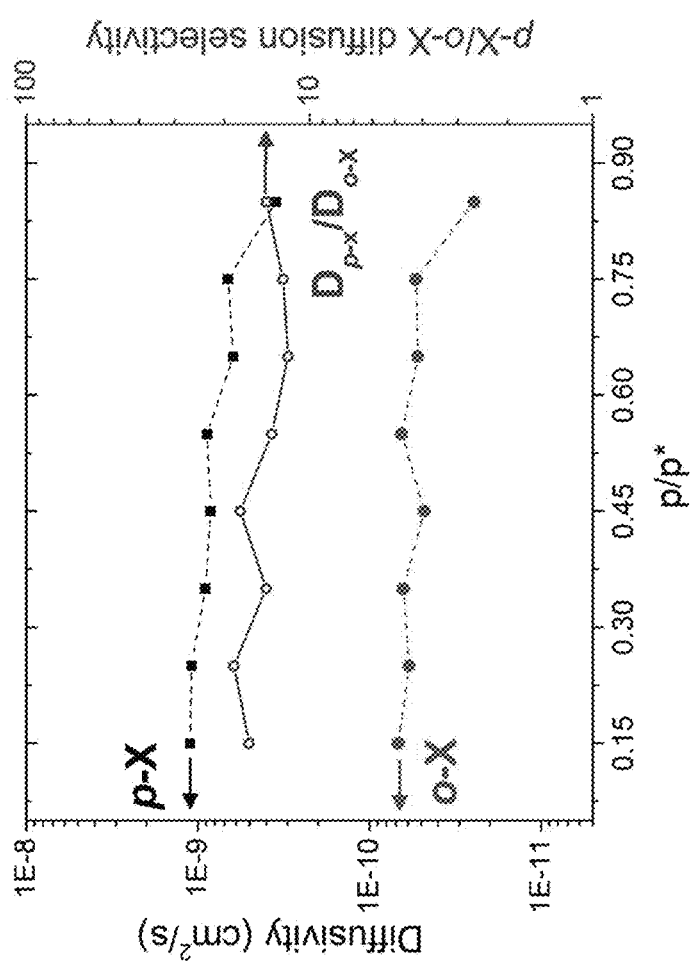
FIG. 11 shows diffusivity values for para-xylene and ortho-xylene with respect to an asymmetric porous carbon membrane structure.
Figure 12:
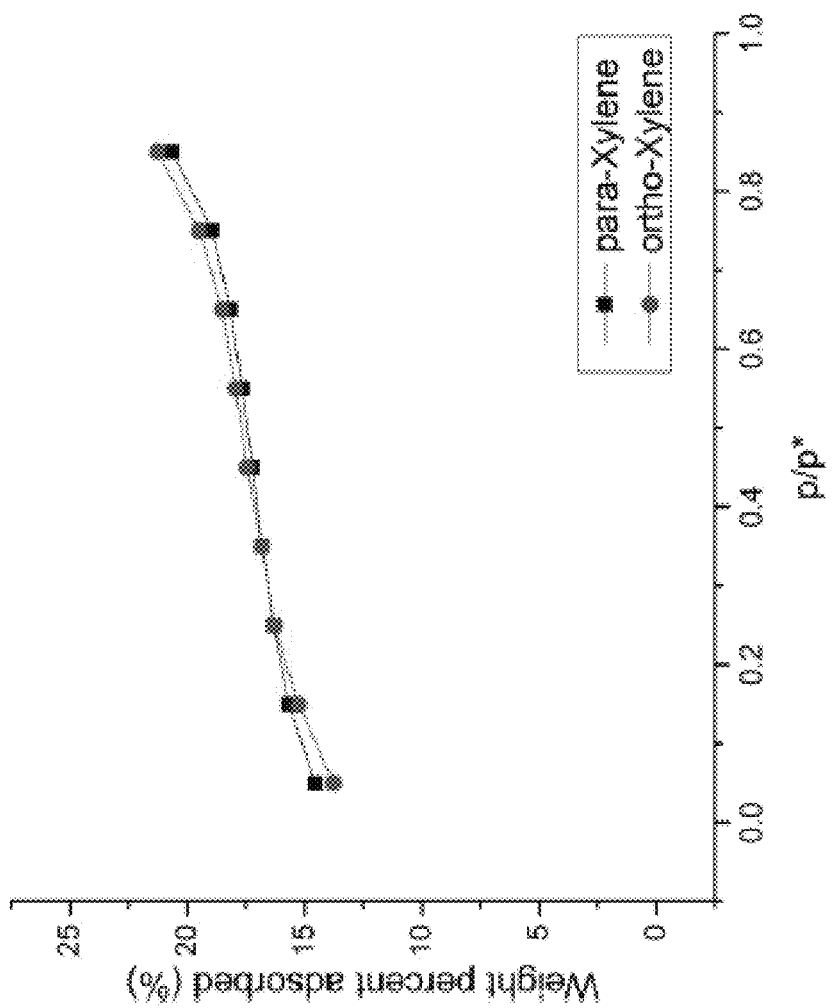
FIG. 12 shows adsorption as a function of pressure for para-xylene and ortho-xylene with respect to an asymmetric porous carbon membrane structure.

FIG. 11 shows the diffusivity of para-xylene and ortho-xylene based on the partial pressure of the component in the feed to the membrane. The diffusivity values in FIG. 11 were calculated based on real time uptake in a membrane sample. The membrane material was placed in a quartz pan attached to a microbalance. The weight of the sample was measured once per minute as the sample was exposed to different relative pressures of xylene in a flowing nitrogen stream. FIG. 11 also shows the ratio of the diffusivity values. As shown in FIG. 11, the diffusivity for para-xylene is about an order of magnitude greater than the diffusivity of ortho-xylene under similar conditions. FIG. 12 shows that the weight percent adsorbed for para-xylene and ortho-xylene as a function of pressure is similar. Instead of being based on solvation, the difference in diffusivity between para-xylene and ortho-xylene is based on the ability of the respective compounds to traverse the sheath layer via the pore network.

Figure 13:
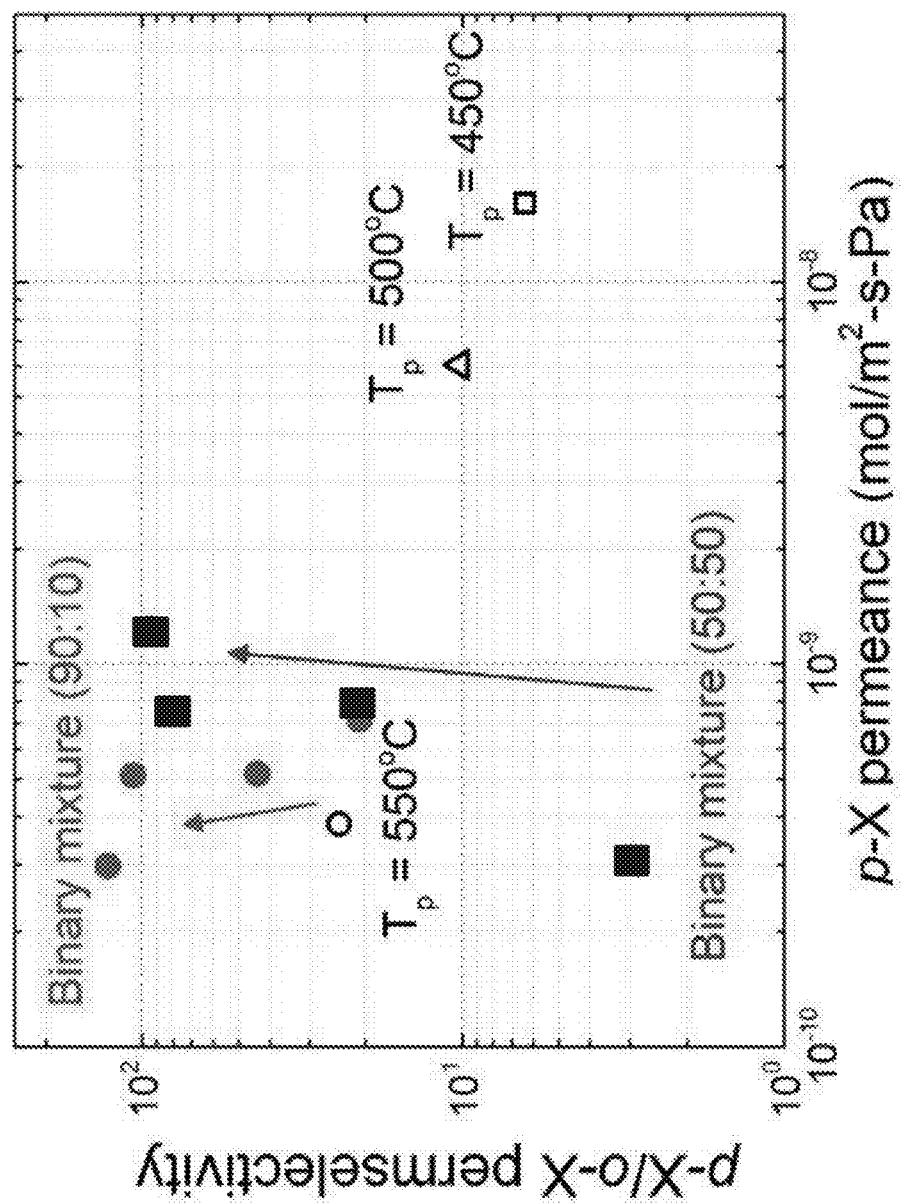
FIG. 13 shows results from hydrocarbon reverse osmosis separation of 50:50 and 90:10 mixtures of para-xylene and ortho-xylene.

FIGS. 9 and 10 shows single component fluxes and ideal selectivities for membrane structures formed after pyrolysis at 550° C. FIG. 13 shows how the ideal selectivities of the membrane structure change based on changes in the pyrolysis temperature. In FIG. 13, the open symbols correspond to ideal selectivities as a function of p-xylene permeance at 450° C., 500° C., and 550° C. The solid symbols correspond to measured values either for a 50/50 composition or a 90/10 composition of p-xylene and o-xylene. As shown in FIG. 13, increasing the pyrolysis target temperature causes an increase in the selectivity for separation of para-xylene and ortho-xylene. Without being bound by a particular theory, this is believed to be due to a narrowing of the peaks in the pore size distribution. This can lead to an overall reduced rate of flow across the sheath layer, but can allow for increased selectivity for permeation of para-xylene across the sheath layer. It is also noted that the measured multi-component selectivities in FIG. 13 are higher than the predicted selectivities based single component values. This is a surprising result, as for some types of membranes, multi-component selectivites can tend to be lower than predicted selectivities based on single component measurements.

Figure 14:
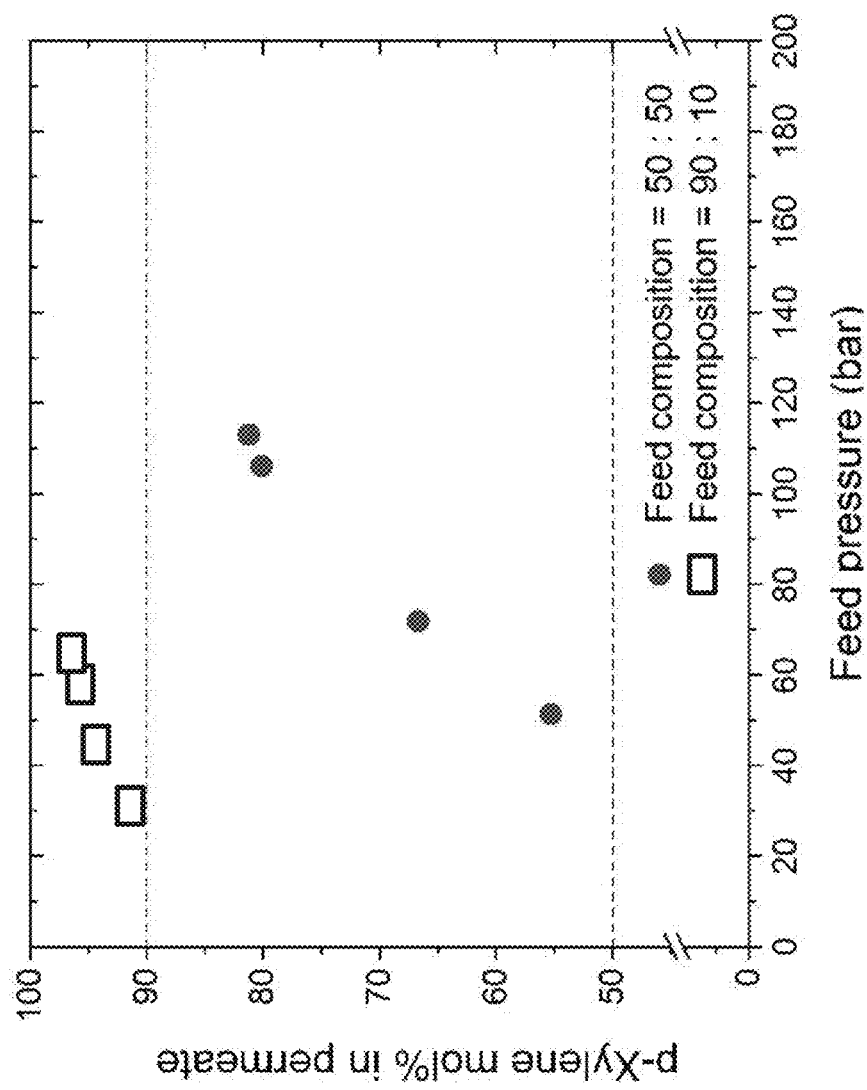
FIG. 14 shows results from hydrocarbon reverse osmosis separation of 50:50 and 90:10 mixtures of para-xylene and ortho-xylene.

FIG. 14 shows the resulting para-xylene content in the permeate for the measured data points shown in FIG. 13. As shown in FIG. 14, the membrane was effective for forming a permeate with increased para-xylene concentration. As the feed pressure was increased, the para-xylene concentration in the permeate also increased. For the 90/10 ratio feed, at higher pressures a para-xylene permeate was formed that approached 99 wt % in purity.

Figure 15:
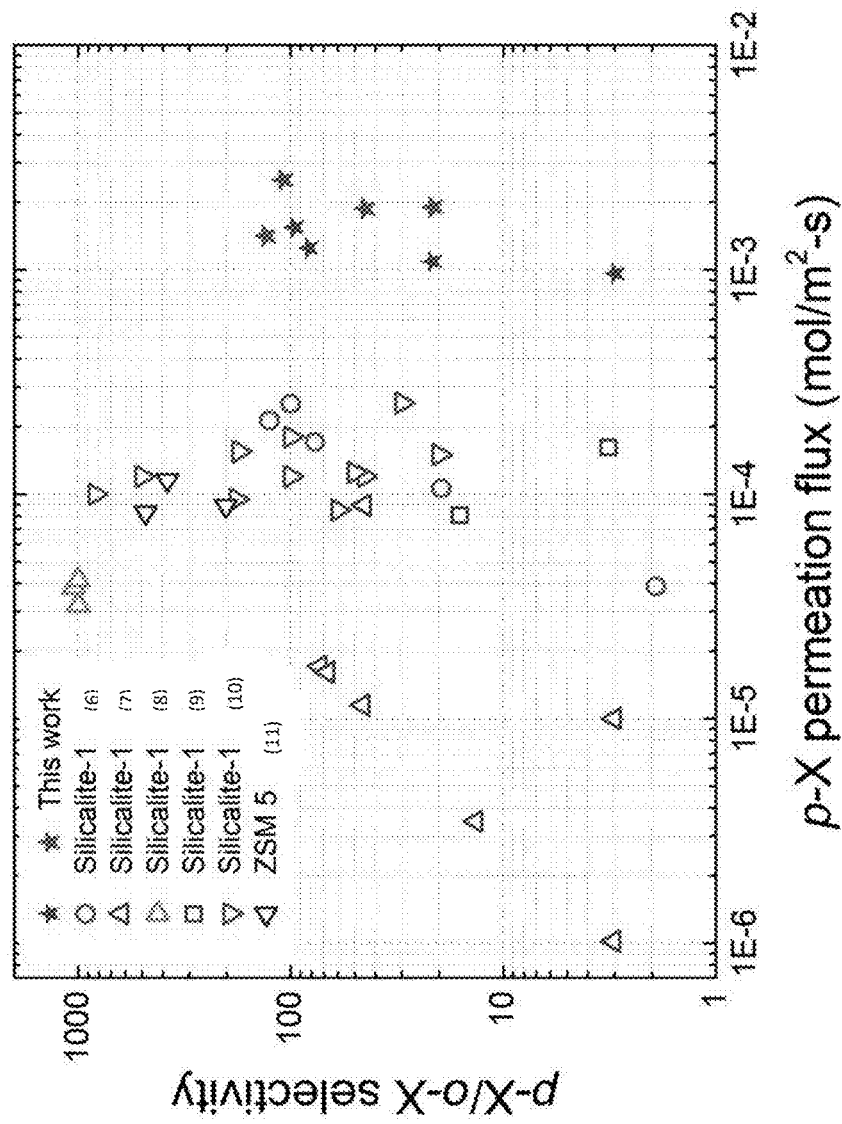
FIG. 15 shows results from hydrocarbon reverse osmosis separation of 50:50 and 90:10 mixtures of para-xylene and ortho-xylene.

FIG. 15 provides a comparison of selectivity for para-xylene in the permeate relative to the total flux across a membrane structure for the data points shown in FIG. 13. In FIG. 15, selectivities relative to permeate flux for a variety of conventional crystalline molecular sieves of MFI framework type are also shown. As noted above, crystalline pore structures may not be suitable for use in the liquid phase conditions corresponding to hydrocarbon reverse osmosis. Instead, crystalline membranes require gas phase separation conditions. This results in a lower permeation rate across the membrane, as shown in FIG. 15. Because hydrocarbon reverse osmosis is performed under liquid phase conditions, the permeation rate is roughly an order of magnitude higher than permeation under gas phase conditions for the conventional MFI framework type molecular sieves shown in FIG. 15.

Example—Membrane Structure Including Porous Metal Structure

Figure 17:
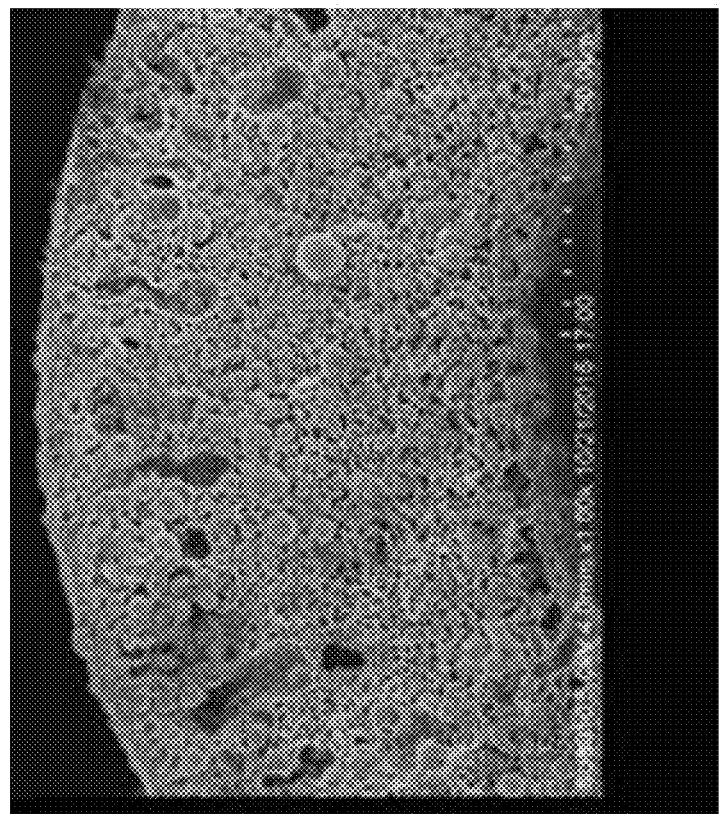
FIG. 17 shows an example of an extruded structure formed from extrusion of a mixture of metal particles and a polymer binder.
Figure 18:
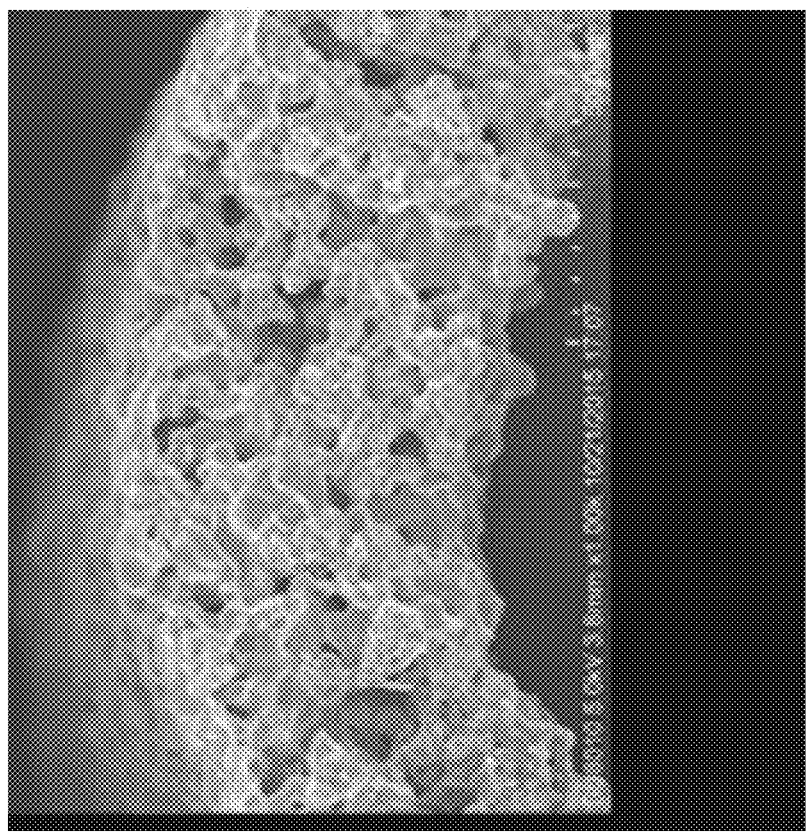
FIG. 18 shows a porous metal structure formed by sintering of the extruded structure of FIG. 17.
Figure 19:
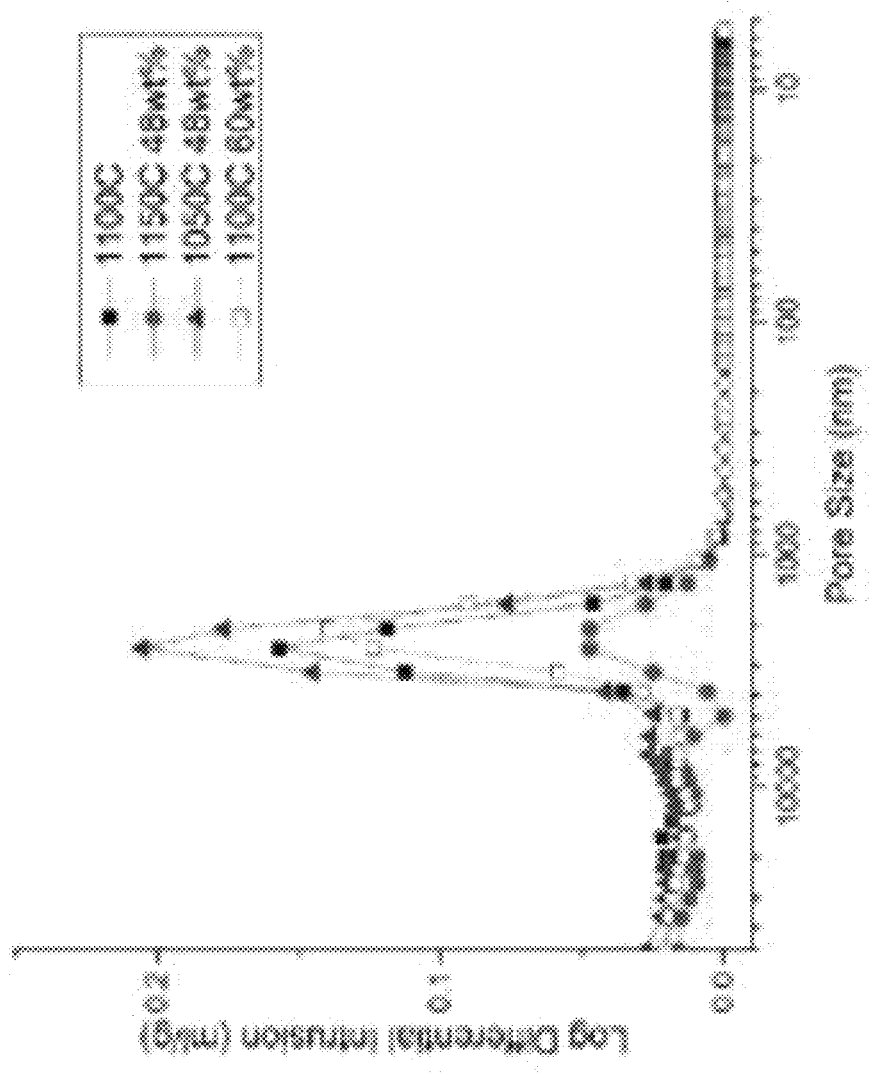
FIG. 19 shows pore size distributions for porous metal structures.

FIG. 17 shows an example of a single layer hollow fiber structure formed from an extrusion mixture of stainless steel particles and PVDF. The stainless steel particles were roughly spherical particles composed of SS316L stainless steel. The particles had an average diameter (characteristic length) of about 3.0 μm. The mixture of stainless steel particles and PVDF was extruded to form an extruded hollow fiber structure having an outer diameter of about 320 μm and an inner diameter of about 215 μm. This roughly corresponds to a thickness of about 53 μm. The extruded hollow fiber structure was then sintered according to a temperature program. After increasing the temperature of the extruded hollow fiber structure to 1100° C. over the course of about 7-8 hours, the extruded hollow fiber structure was sintered at a temperature of about 1100° C. for about 1 hour to form a porous metal membrane structure, as shown in FIG. 18. The length of the sintering process was selected to allow for partial sintering of the metal particles to form the porous metal membrane structure. FIG. 19 shows the pore size distribution for porous metal structures formed according to the above procedure using various sintering temperatures and various mixtures (by weight) of stainless steel metal particles and polymer binder. The weight percentages shown in FIG. 19 correspond to the weight percent of the stainless steel metal particles relative to the total weight of metal particles plus polymer binder. As shown in FIG. 19, the average pore size for the pores in the pore network of the porous metal structure does not appear to change substantially based on sintering temperature and/or based on the relative amounts of metal and binder. However, increasing the sintering temperature when forming the porous metal structure does appear to reduce the overall volume of available pores, based on the reduced peak intensity with increasing temperature. This reduction in available pore volume is believed to correspond to a reduction in the number of available pore channels for permeation.

Figure 20:
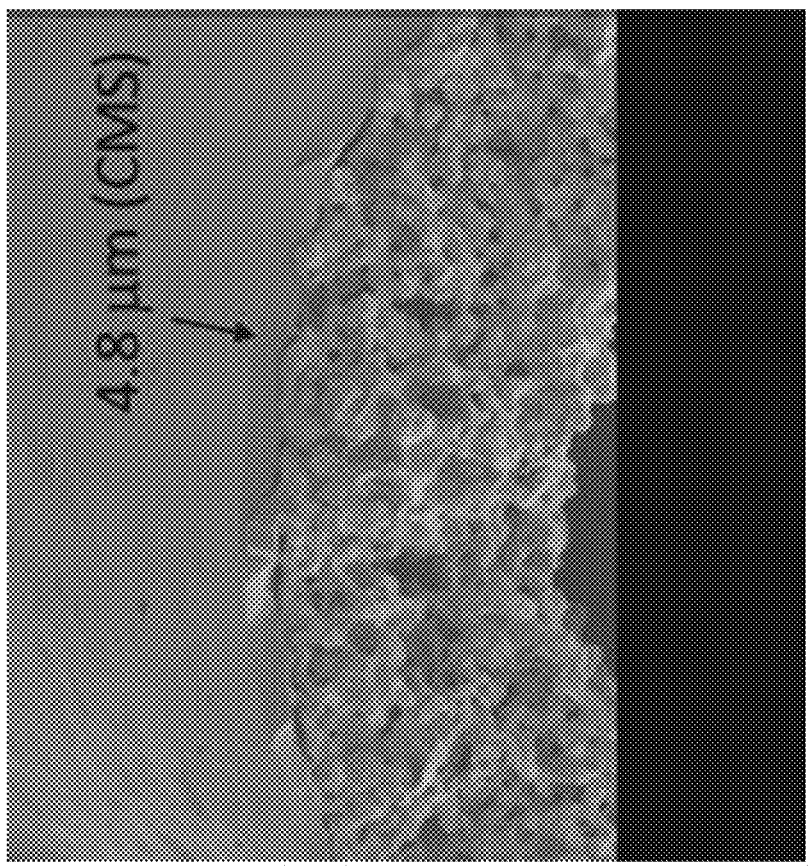
FIG. 20 shows an example of an asymmetric membrane structure.

The porous metal membrane structure was then coated with Matrimid® 5218 to form a coating layer using a dip coating procedure. The porous metal membrane structure was dip coated using a 15 wt % polymer solution balanced with dichloromethane (i.e., 15 wt % polymer in dichloromethane solvent). The resulting coating layer was pyrolyzed at a temperature of about 550° C. for about 120 minutes (after a suitable temperature program to ramp to 550° C.) to form an asymmetric membrane structure as shown in FIG. 20. The pyrolysis method was otherwise similar to pyrolysis of an asymmetric membrane as described herein. After pyrolysis, the selective layer of the asymmetric membrane structure had a smallest median pore size peak of between 3 and 4 Angstroms. A single fiber of the asymmetric membrane structure with an active length of about 7 cm was loaded into a module for characterization of the asymmetric membrane structure. The He/N$_2$ selectivity of the fiber was about 13.8, which is believed to indicate that the asymmetric membrane structure was substantially free of mesopore (or larger) defects.

Figure 21:
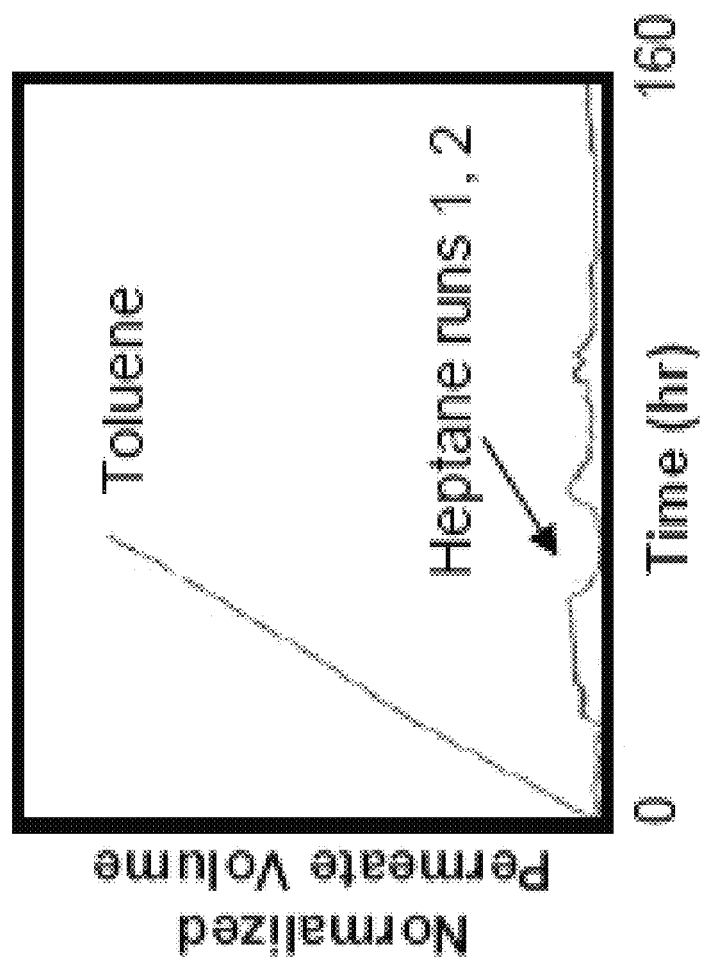
FIG. 21 shows examples of single component permeance through an asymmetric membrane structure for toluene and n-heptane.

The fiber corresponding to the asymmetric membrane structure was also characterized based on single component liquid phase permeation of toluene and n-heptane at 22° C. and a similar pressure for both components. The single component permeation of toluene and n-heptane through the membrane at the reverse osmosis conditions as a function of time is shown in FIG. 21. FIG. 21 shows that toluene was able to pass through the asymmetric membrane structure, while the amount of n-heptane permeance was more limited. For the steady state single component permeance amounts shown in FIG. 21, the single component toluene liquid phase permeance was about 5.09×10$^{15}$ mol/m$^2$-s-Pa, while the single component n-heptane liquid phase permeancce was about 6.04×10$^{17}$ mol/m$^2$-s-Pa. This corresponds to a selectivity for toluene relative to n-heptane of about 84. This can appear to be a surprising result, as the conventional molecular diameter of toluene is about 5.8 Angstroms while the conventional molecular diameter of n-heptane is about 4.3 Angstroms. However, due to the primarily planar nature of the toluene ring, it may be possible that in some orientations the apparent molecular diameter of toluene can be smaller than n-heptane. Additionally or alternately, the porous carbon membrane may have some similarity in surface properties to an asphaltenic material. It is possible that the relatively low solubility of n-heptane in asphaltenic materials is related to n-heptane having a reduced permeance. Based on the He/N$_2$ selectivity of 13.8 (derived from single component permeance) noted above, it is believed that the porous carbon membrane is relatively free of defects, and therefore it is not believed that the toluene is being primarily transported in mesoporous channels. Based on FIG. 21, for a separation of toluene from n-heptane by reverse osmosis, it is believed that the rate of transport of toluene into the permeate can be enhanced by increasing the pressure for the separation conditions.

ADDITIONAL EXAMPLES

In various aspects, the benefits of the asymmetric membranes described herein can be related to the ability to form a thin selective membrane layer (such as a selective layer with a thickness of 0.08 μm to 5.0 μm) while still providing a structurally stable membrane structure. It is noted that thicker versions of selective membrane layers can be formed, such as a selective membrane layer with a thickness of 40 μm or more. Such thicker versions of a selective membrane layer can have sufficient structural integrity to allow for use of the selective membrane layer without a separate support layer. The permeation rate of components passing through such a thicker membrane layer under reverse or forward osmosis conditions can be insufficient to allow for commercial scale separations. However, such thicker membrane layers can be used to demonstrate the types of separations that are feasible using the asymmetric membrane structures described herein.

An example of formation of a single porous carbon layer can be based on calcining of a single layer PVDF membrane structure. Asymmetrically porous PVDF hollow fiber was spun from a polymer solution corresponding to a mixture of low-boiling point solvent (Tetrahydrofuran, THF) and high-boiling point solvent (Dimethylacetamide, DMAc). The weight ratio between THF and DMAs was kept to 8:2 and ethanol was used as a non-solvent. The solution included 25 wt % PVDF, 14.6 wt % DMAc, 58.4 wt % THF, and 2 wt % ethanol. The polymer solution was mixed on a rotating mixer for 3-5 days at 55° C. The polymer solution was then transferred into high-pressure syringe pump and a hollow fiber was spun using dry jet wet-quench spinning conditions. Table 1 shows an example of suitable conditions for performing hollow fiber spinning. As-spun fibers were solvent exchanged in a sequence of deionized water-methanol-hexane and then further dried in a vacuum oven. The resulting fibers were then suitable for cross-linking and calcination under conditions similar to those used for forming an asymmetric membrane structure.

TABLE 1

PVDF Hollow Fiber Spinning Parameters

| | | |
|---|---|---|
| Bore fluid composition (w/w) | THF/DMAc/water | 16/4/80 |
| Core flow-rate (ml/h) | | 400 |
| Bore fluid flow rate (ml/h) | | 360-480 |
| Air gap (cm) | | 30 |
| Drum take-up rate (m/min) | | 30 |
| Spinning temperature (° C.) | | 55 |
| Quench bath temperature (° C.) | | 50 |

Additional Example a—Ethanol/Toluene and Toluene/Mesitylene Separations Using Single Porous Carbon Layer In the following example, a single membrane layer formed from a Matrimid® polymer was used to separate ethanol from toluene under reverse/forward osmosis conditions. The conditions below can be considered as reverse osmosis conditions based on the elevated pressure used to cause permeation across the membrane. However, the conditions below can also be similar to forward osmosis conditions based on the use of a sweep stream to remove permeated products from the permeate side of the membrane. It is noted that the pressure driving force for a separation can correspond to osmotic pressure, hydraulic pressure, or both.

Hollow fibers of Matrimid® were extruded as a single layer fiber. The extruded fibers were calcined according to a procedure similar to the procedures described above for calcining an asymmetric membrane structure to form a porous carbon layer. The resulting porous carbon hollow fibers were roughly 104 mm long, had a roughly 230 μm outer diameter, an inner diameter of roughly 150 μm, and a wall thickness of roughly 40 μm. A separation module having a shell and tube configurations was made using 14 of the porous carbon hollow fibers.

The separation module was used to perform a separation of a 50 vol %/50 vol % mixture of toluene and ethanol. The mixture of toluene and ethanol was circulated on the outside (shell side) of the fibers at a rate of 4 ml/min at a pressure of 179 barg (17.9 MPag) and a temperature of about 21° C. After reaching steady state for the flow of the toluene/ethanol mixture, the internal volume (bore or tube side) of the fibers was filled with isooctane at a pressure of about 1 barg (0.1 MPag). The isooctane acted as a draw solution to provide a forward osmosis effect acting in conjunction with the hydraulic pressure differential of 180 bar between the shell side and bore side of the membrane.

Approximately 24 hours after filling the bore with the isooctane draw solution, samples were withdrawn from the permeate side and the retentate side for analysis. Due to the thickness of the single (selective) layer of the hollow fiber membranes in the separation module (>40 μm), the total amount of permeate transported across the membrane corresponded to less than 0.1 vol % of the feed that was exposed to the separation module. However, the permeate collected during the reverse/forward osmosis separation indicated a significant increase in ethanol concentration relative to toluene in the permeate. It is noted that back diffusion of isooctane draw solution across the membrane in the opposite direction was negligible (~0.0001 vol % isooctane detected in the retentate). The separation factor ratio of ethanol to toluene in the permeate (vol/vol) was 5.14, as determined by $\{(X_{ethanol}/X_{toluene})_{permeate}/(X_{ethanol}/X_{toluene})_{retentate}\}$, where "X" is the volume of the component in either the permeate or the retentate. This corresponded to 83.7 vol % ethanol and 16.3 vol % toluene for the composition of the permeate that traversed the membrane. Although the flux across the membrane was low, the results demonstrate the suitability of the porous carbon layer for separation of ethanol from toluene. It is believed that incorporation of a similar porous carbon layer as part of an asymmetric membrane structure, as described herein, would allow for separation of ethanol from toluene at similar selectivity but at permeation rates that are more suitable for commercial scale separations.

A second separation was performed using the module described above but at an increased hydraulic pressure. The feed, draw solution, and other conditions were similar to the above, with the exception of having a hydraulic pressure of roughly 200 bar (20 MPag). Due to the increased pressure, the separation factor ratio of ethanol to toluene in the permeate (vol/vol) was 6.9 (87.3 vol % ethanol, 12.7 vol % toluene). This demonstrates the ability, known in the art for reverse osmosis processes, to increase the separation factor for the faster permeating species in a separation by increasing the applied hydraulic pressure.

A third separation was performed using the module described above, but with a different solution for separation. For the third separation, instead of using the ethanol/toluene mixture, a 50 vol %/50 vol % mixture of toluene and mesitylene was circulated on the outside (shell side) of the fibers at a pressure of 180 barg (18 MPag) and a temperature of about 21° C. The draw solution other separation conditions were otherwise similar to the above. Samples of the retentate side and permeate side were withdrawn after 25.5 hours for analysis. Similar to the ethanol/toluene separation, the ratio of the permeate flow across the membrane to the feed flow was less than 0.1 vol %. The separation factor ratio $\{(X_{toluene}/X_{mesitylene})_{permeate}/(X_{toluene}/X_{mesitylene})_{retentate}\}$ for the separation was 57.6 (98.8 vol % toluene, 1.7% mesitylene), indicating high selectivity for toluene permeation relative to mesitylene.

Additional Example B—Reverse Osmosis Separations of Salt Water Using Single Porous Carbon Layers In the following examples, a single membrane layer formed from a Matrimid® polymer or formed from a polyvinylidene fluoride polymer was used to separate water from a salt water feed under reverse osmosis conditions.

For separations using a Matrimid® polymer, a single layer hollow fiber membrane was formed under conditions similar to those described above. The polymer solution for forming the initial single layer hollow fiber polymer structure included 58.9 wt % n-methylpyrollidone (NMP), 14.9 wt % ethanol, and 26.2 wt % Matrimid®. The solution was formed by first adding the NMP, then ethanol, and then the polymer to a container. The container was then sealed and the components were mixed under a heat lamp to provide a temperature of about 40° C. to about 50° C. The mixing was performed until a single phase was formed. The polymer solution was then transferred into high-pressure syringe pump and a hollow fiber was spun using dry jet wet-quench spinning conditions. The conditions for forming the Matrimid® hollow fiber are shown in Table 2.

TABLE 2

Matrimid ® Hollow Fiber Spinning Parameters

| | |
|---|---|
| Polymer (core) flow rate (ml/hr) | 180 |
| Bore flow rate (ml/hr) | 60 |

TABLE 2-continued

Matrimid ® Hollow Fiber Spinning Parameters

| | |
|---|---|
| Bore fluid composition | NMP/H$_2$O 96 wt %/4 wt % |
| Drum take-up rate (m/min) | 50 |
| Water bath temperature (° C.) | 50 |
| Spinning temperature (° C.) | 50 |
| Air gap (cm) | 18.5 |

After forming hollow fibers, the hollow fibers were soaked in deionized water for three days, changing the water once per day. The washed hollow fibers were then soaked three times in methanol, with the methanol being changed every 30 minutes (total methanol soak time 1.5 hours). The methanol-washed fibers were then soaked with n-hexane using the same time schedule as the methanol soak. After the hexane wash, the fibers were then air dried for 2-3 hours, followed by drying in at 80° C. overnight in a vacuum oven at a pressure below 100 kPa-a (i.e., drying under vacuum).

After vacuum drying, the dried polymer hollow fibers were converted to a porous carbon membrane hollow fiber. The dried polymer hollow fibers were cut into an appropriate length to fit in a tube furnace. The fibers were then placed on a stainless steel mesh bed. A 'U' shape nickel wire was used to stabilize the fibers on the bed. The tube furnace was then sealed and the furnace was flushed with 400 ml/min Ar at room temperature until the oxygen level was down to 10 vppm. After achieving the desired oxygen level, the Ar flow rate was maintained throughout the pyrolysis process. Pyrolysis was performed by ramping the temperature of the furnace according to the following heating profile: a) 50° C.-250° C.: heating rate 13.3° C./min; b) 250° C.-535° C.: heating rate 3.8° C./min; and c) 535° C.-550° C.: heating rate 0.25° C./min. The final pyrolysis temperature of 550° C. was then maintained for 2 additional hours. The resulting porous carbon hollow fibers were then allowed to cool down inside the furnace. The resulting porous carbon hollow fibers had an outer diameter of 272.4 μm and an inner diameter of 160.2 μm.

A resulting porous carbon hollow fiber was then used as a membrane for a reverse osmosis separation of salt water. A 2 wt % salt water solution was prepared by mixing Morton® fine sea salt with deionized water. The conductivity of the salt water solution was 47.9 mS/cm. The salt water was exposed to the outside of the fiber at a hydraulic pressure of 700 psig (4.8 MPag). The resulting flux across the hollow fiber was 8.1×10$^{-4}$, L/m$^2$-hr with a salt rejection rate of 62.4% (i.e., the permeate water included 62.4 wt % less salt than the salt water feed to the membrane). The salt rejection rate was determined based on conductivity of the permeate. The ability to reject sea salt under reverse osmosis conditions demonstrates the capability of using a porous carbon membrane for separations of water from solutions containing various ionic salts.

Additional tests for performing reverse osmosis separations on salt water were performed using a porous carbon membrane made from PVDF according to conditions similar to those in Additional Example A above. It is noted that the porous carbon membranes in Additional Example A showed a selectivity for separation of He from N$_2$ of greater than 6, while the porous carbon membrane used in this example for salt water reverse osmosis only had a selectivity of about 3 for He versus N$_2$. Without being bound by any particular theory, the lower selectivity for separating He versus N$_2$ was believed to be due to defects in the membrane, which can result in some non-selective flow through the membrane.

The porous carbon membrane formed from PVDF hollow fiber was used for salt water separation under conditions similar to those described above. A 2 wt % salt water solution was prepared by mixing Morton® fine sea salt with deionized water. The conductivity of the salt water solution was 47.9 mS/cm. The salt water was circulated on the outside of the fiber at a rate of 0.16 mg/s. The reverse osmosis separation was performed at a hydraulic pressures of 300 psig (2.1 MPag) and 500 psig (3.4 MPag). At 2.1 MPag, the flux of permeate across the membrane was 0.084 L/m$^2$-hr, which corresponded to a mass flow rate of about 0.16 mg/s. The salt rejection rate was ~8.0%. At 3.4 MPag, the mass flow rate of permeate was about 0.36 mg/s, but with a rejection rate of ~5.5%. The lower rejection rate at increased pressure is believed to reflect the presence of defects within the membrane, as was also indicated by the reduced selectivity for He relative to N$_2$. In particular, as shown in Additional Example A, selectivity for separation of ethanol from toluene increased with increasing pressure, as would be expected from a reverse osmosis process. However, it is also generally known that non-selective flow (such as through membrane defects) can lead to decreases in selectivity with increasing pressure. The ability to reject a portion of the sea salt is believed to indicate the presence of some separation by reverse osmosis, with the influence of defects in the membrane increasing with increasing pressure.

ADDITIONAL EMBODIMENTS

Embodiment 1

A method for separating water by osmosis, comprising: performing a membrane separation on a feed stream comprising water and a second component comprising a hydrocarbon, a hydrocarbonaceous compound, an ionic compound, an inorganic compound, or a combination thereof to form a permeate enriched in the first component and a retentate depleted in the first component, wherein performing the membrane separation comprises exposing the hydrocarbonaceous stream to a membrane structure comprising a first membrane layer and a second membrane layer under reverse osmosis conditions or forward osmosis conditions, the reverse osmosis conditions or forward osmosis conditions comprising a feed pressure of at least 1.0 MPag, the second membrane layer comprising a porous carbon layer having a pore size distribution comprising a smallest substantial pore size peak having a median pore size of about 3.0 Angstroms to about 6.0 Angstroms.

Embodiment 2

A method for separating a feed stream, comprising: performing a membrane separation on a feed stream comprising a first component and a second component, the first component and the second component comprising a hydrocarbon, a hydrocarbonaceous compound, an inorganic compound, or a combination thereof, the feed stream comprising 5 wt % to 95 wt % of the first component, to form a permeate enriched in the first component and a retentate depleted in the first component, wherein performing the membrane separation comprises exposing the feed stream to a membrane structure comprising a first membrane layer and a second membrane layer under reverse osmosis conditions or forward osmosis conditions, the reverse osmosis conditions or forward osmosis conditions comprising a feed pressure of at least 0.2 MPag, the second membrane layer comprising a porous carbon layer having a pore size distribution comprising a smallest substantial pore size peak having a median pore size of about 3.0 Angstroms to about 50 Angstroms, or about 3.0 Angstroms to about 10 Angstroms, or about 5.8 Angstroms to about 6.8 Angstroms.

Embodiment 3

The method of Embodiment 1 or 2, wherein the substantial pore size peak corresponding to the smallest median pore size has a median pore size when the membrane structure is exposed to a liquid for separation that differs by 10% or less, or 5% or less, or 2% or less from the median pore size when the membrane structure is not exposed to the liquid for separation.

Embodiment 4

The method of any of the above embodiments, wherein the reverse osmosis conditions or forward osmosis conditions comprise a feed pressure of about 200 barg (~20 MPag) or less.

Embodiment 5

The method of any of the above embodiments, wherein the reverse osmosis conditions or forward osmosis conditions comprise a feed pressure of about 15 barg (~1.5 MPag) to about 200 barg (~20 MPag), or about 40 barg (~4.0 MPag) to about 200 barg (~20 MPag), or about 50 barg (~5.0 MPag) to about 150 barg (~15 MPag).

Embodiment 6

The method of any of the above embodiments, wherein the feed stream comprises less than about 1.0 wt % water, or less than about 0.1 wt %; or wherein the feed stream comprises about 0.1 wt % to about 30 wt % water, or about 0.1 wt % to 20 wt %, or about 1.0 wt % to about 10 wt %, and optionally wherein the reverse osmosis conditions or forward osmosis conditions comprise a feed pressure of about 10 barg (~1.0 MPag) to about 100 barg (~10 MPag), or about 15 barg (~1.5 MPag) to about 70 barg (~7.0 MPag), or about 10 barg (~1.0 MPag) to about 50 barg (~5.0 MPag).

Embodiment 7

The method of any of the above embodiments, wherein the feed stream comprises less than about 1.0 wt % of the second component, or less than about 0.1 wt % of the second component, or about 0.1 wt % to about 30 wt % of the second component, or about 0.1 wt % to 20 wt % of the second component, or about 1.0 wt % to about 10 wt % of the second component, and optionally wherein the reverse osmosis conditions comprise a feed pressure of about 10 MPag to about 40 MPag, or about 10 MPag to about 25 MPag, or about 20 MPag to about 40 MPag.

Embodiment 8

The method of any of the above embodiments, wherein the first membrane layer and the second membrane layer comprise porous carbon layers, or wherein the first membrane layer comprises a porous metal structure (i.e., porous metal layer) and the second membrane layer comprises a porous carbon layer.

Embodiment 9

The method of any of the above embodiments, wherein the smallest substantial pore size peak has a median pore size of about 4.0 Angstroms to about 6.0 Angstroms, or about 3.5 Angstroms to about 5.5 Angstroms.

Embodiment 10

The method of any of Embodiments 2-9, wherein the first component comprises sulfuric acid and the second component comprises acid soluble oils, and optionally wherein the smallest substantial pore size peak has a median pore size of about 5.0 Angstroms to about 10 Angstroms.

Embodiment 10

The method of any of the above embodiments, wherein the smallest substantial pore size peak has a median pore size of about 6.0 Angstroms to about 7.0 Angstroms, wherein the first component comprises para-xylene, or a combination thereof.

Embodiment 11

The method of any of the above embodiments, wherein the second component comprises a homogeneous catalyst, and optionally wherein the wherein the smallest substantial pore size peak has a median pore size of about 4.0 Angstroms to about 7.0 Angstroms.

Embodiment 12

The method of any of the above embodiments, wherein the smallest substantial pore size peak has a median pore size of about 4.5 Angstroms to about 6.1 Angstroms, or about 4.5 Angstroms to about 5.2 Angstroms, or about 4.7 Angstroms to about 6.1 Angstroms, and optionally wherein a) the first component comprises ethanol, b) the first component comprises isobutane, and/or c) the second component comprises 2,2,4 trimethyl pentane.

Embodiment 13

The method of any of the above embodiments, wherein the second component comprises methylmethacrylate, methacrylic acid, or a combination thereof.

Embodiment 14

The method of any of the above embodiments, wherein the smallest substantial pore size peak has a median pore size of about 3.0 Angstroms to about 6.0 Angstroms, or about 4.0 Angstroms to about 6.0 Angstroms, or about 3.5 Angstroms to about 5.5 Angstroms, and optionally wherein i) the first component is water and the second component is isopropyl alcohol or ii) the first component comprises a $C_4$-$C_8$ paraffin and the second component comprises a $C_{10}$-$C_{20}$ paraffin.

Embodiment 15

The method of any of the above embodiments, wherein the smallest substantial pore size peak has a median pore size of about 3.2 Angstroms to about 4.2 Angstroms and optionally wherein the first component comprises at least one of ethylene, propylene, and n-butylene, and the second component comprises at least one of ethane, propane, and n-butane (for example, wherein the first component comprises ethylene and the second component comprises ethane, or wherein the first component comprises propylene and the second component comprises propane, or wherein the first component comprises n-butylene and the second component comprises n-butane).

Embodiment 16

The method of any Embodiments 2-15, wherein the first component and the second component comprise hydrocarbon isomers.

Embodiment 17

The method of any of any of the above embodiments, wherein the first membrane layer has a pore volume of at least 0.2 cm$^3$/g of pores with a median pore size of at least 20 nm.

Embodiment 18

The method of any of any of the above embodiments, wherein the second membrane layer has a BET surface area of at least about 100 m$^2$/g, or at least about 200 m$^2$/g, or at least about 300 m$^2$/g, or at least about 400 m$^2$/g, or at least about 500 m$^2$/g.

Embodiment 19

A method for separating hydrocarbons and/or hydrocarbonaceous compounds, comprising: performing a membrane separation an hydrocarbonaceous stream comprising a first component and a second component, the hydrocarbonaceous stream comprising 5 wt % to 95 wt % of the first component, to form a permeate enriched in the first component and a retentate depleted in the first component, wherein performing the membrane separation comprises exposing the hydrocarbonaceous stream to a membrane structure comprising a plurality of porous carbon layers, a first membrane layer of the membrane structure having a pore volume of at least 0.2 cm$^3$/g of pores with a median pore size of at least 20 nm, a second membrane layer of the membrane structure having a BET surface area of at least about 300 m$^2$/g (or at least about 400 m$^2$/g, or at least about 500 m$^2$/g), the second membrane layer having a pore size distribution comprising a smallest substantial pore size peak having a median pore size of about 5.8 Angstroms to about 6.8 Angstroms, or about 6.0 Angstroms to about 6.5 Angstroms.

Embodiment 20

The method of Embodiment 19, wherein the hydrocarbonaceous stream comprises an effluent stream from a xylene isomerization process, a hydrocarbon stream, or a combination thereof.

Embodiment 21

The method of Embodiment 19 or 20, wherein the hydrocarbonaceous stream comprises C$_{8+}$ aromatics, the hydrocarbonaceous stream comprising 5 wt % to 95 wt % p-xylene, the first component being p-xylene and the second component being at least one of m-xylene and o-xylene.

Embodiment 22

The method of any of the above embodiments, wherein a size difference between the first component and the second component is about 3.0 Angstroms or less, or about 2.0 Angstroms or less, or about 1.1 Angstroms or less.

Embodiment 23

The method of any of the above embodiments, wherein a peak width of the smallest substantial pore size peak at half of the peak height is about 75% or less of the size difference between the first component and the second component, or about 50% or less.

Embodiment 24

The method of any of any of the above embodiments, wherein performing the membrane separation comprises exposing the feed stream to the membrane structure under reverse osmosis conditions.

Embodiment 25

The method of any of any of the above embodiments, wherein the mole fraction of the first component in the liquid phase can be
at least 200% greater in the permeate when the molar concentration in the feed is in a range from 0.1% to 10%,
at least 100% greater in the permeate when the molar concentration in the feed is in a range from 10% to 20%,
at least 75% greater in the permeate when the molar concentration in the feed is in a range from 20% to 40%,
at least 50% greater in the permeate when the molar concentration in the feed is in a range from 40% to 60%,
at least 20% greater in the permeate when the molar concentration in the feed is in a range from 60% to 80%,
at least 10% greater in the permeate when the molar concentration in the feed is in a range from 80% to 90%,
or a combination of any two or more of the above.

Embodiment 26

The method of any of any of the above embodiments, wherein a selectivity is defined as Selectivity=[$\chi_A$(Permeate)/$\chi_B$(Permeate)]/[$\chi_A$(Permeate)/$\chi_B$(Permeate)]

where $\chi_A$ (Permeate) is the mole fraction of A in the permeate, $\chi_B$ (Permeate) is the mole fraction of B in the permeate, $\chi_A$ (Feed) is the mole fraction of A in the feed, and $\chi_B$ (Feed) is the mole fraction of B in the feed, and wherein the selectivity for the first component relative to the second component under the osmosis conditions is greater than 2, or 5, or 10, or 20, or 40, or 100.

Embodiment 27

The method of any of any of the above embodiments, wherein the membrane structure comprises a hollow fiber membrane structure.

Embodiment 28

The method of any of any of the above embodiments, wherein the second membrane layer of the membrane structure has a thickness of about 3 microns or less or about 1 micron or less, or about 0.5 microns or less.

Embodiment 29

The method of any of any of the above embodiments, wherein the membrane structure comprises a storage modulus of at least about 200 MPa at 300° C., or at least about 300 MPa at 100° C., or at least about 300 MPa at 200° C.

Embodiment 30

The method or membrane structure of any of the above embodiments, wherein a median pore size is a median pore width, wherein a pore size peak is a pore width peak, and/or wherein a pore size distribution is a pore width distribution.

Embodiment 31

The method of any of the above embodiments, wherein the mole fraction of the first component in the liquid phase can be
at least 200% greater in the permeate when the molar concentration in the feed is in a range from 0.1% to 10%,
at least 100% greater in the permeate when the molar concentration in the feed is in a range from 10% to 20%,
at least 75% greater in the permeate when the molar concentration in the feed is in a range from 20% to 40%,
at least 50% greater in the permeate when the molar concentration in the feed is in a range from 40% to 60%,
at least 20% greater in the permeate when the molar concentration in the feed is in a range from 60% to 80%,
at least 10% greater in the permeate when the molar concentration in the feed is in a range from 80% to 90%,
or a combination of any two or more of the above.

Embodiment 32

The method of any of the above embodiments, wherein a selectivity is defined as $$\text{Selectivity}=[\chi_A(\text{Permeate})/\chi_B(\text{Permeate})]/[\chi_A(\text{Permeate})/\chi_B(\text{Permeate})]$$

where $\chi_A$ (Permeate) is the mole fraction of A in the permeate, $\chi_B$ (Permeate) is the mole fraction of B in the permeate, $\chi_A$ (Feed) is the mole fraction of A in the feed, and $\chi_B$ (Feed) is the mole fraction of B in the feed, and wherein the selectivity for the first component relative to the second component under the osmosis conditions is greater than 2, or 5, or 10, or 20, or 40, or 100.

Embodiment 33

The method of any of the above embodiments, wherein for hydrocarbons with a molecular dimension greater than the median pore size of the smallest substantial pore size peak by at least one of i) about 0.5-0.6 Angstroms ii) about 1.0-1.2 Angstroms iii) about 2.0-2.2 Angstroms iv) about 5.0-5.3 Angstroms, the permeances $\mathcal{N}_i/(P^{feed}-P^{permeate})$ of the hydrocarbons at temperatures between 20° C. and 100° C. and at least one of a) pressures between 2 MPa and 5.5 MPa and b) pressures between 50 kPa and 1000 kPa, increase by a) less than a factor of 5 when the feed pressure is doubled and by less than a factor of 10 when the feed pressure is quadrupled; or b) less than a factor of 3 when the feed pressure is doubled and by less than a factor of 6 when the feed pressure is quadrupled; or c) less than a factor of 2 when the feed pressure is doubled and by less than a factor of 4 when the feed pressure is quadrupled; or d) less than a factor of 1.15 when the feed pressure is doubled and by less than a factor of 1.25 when the feed pressure is quadrupled.

Embodiment 34

A method for separating hydrocarbons and/or hydrocarbonaceous compounds, comprising: performing a membrane separation on a hydrocarbonaceous stream comprising a first component and a second component, the first component and the second component being hydrocarbon isomers, the hydrocarbonaceous stream comprising 5 wt % to 95 wt % of the first component, to form a permeate enriched in the first component and a retentate depleted in the first component, wherein performing the membrane separation comprises exposing the hydrocarbonaceous stream to a membrane structure comprising a first membrane layer and a second membrane layer under pervaporation conditions or perstraction conditions, the second membrane layer having a pore size distribution comprising a smallest substantial pore size peak having a median pore size of about 3.0 Angstroms to about 50 Angstroms, and wherein the substantial pore size peak corresponding to the smallest median pore size has a median pore size when the membrane structure is exposed to a liquid for separation that differs by 10% or less, or 5% or less, or 2% or less from the median pore size when the membrane structure is not exposed to the liquid for separation.

Embodiment 35

The method of Embodiment 33, wherein the first membrane layer and the second membrane layer comprise porous carbon layers, or wherein the first membrane layer comprises a porous metal structure and the second membrane layer comprises a porous carbon layer.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A method for separating a feed stream, comprising:
performing a membrane separation on a feed stream comprising a first component and a second component, the first component and the second component comprising a hydrocarbon, a hydrocarbonaceous compound, an inorganic compound, or a combination thereof, the feed stream comprising 5 wt % to 95 wt % of the first component, to form a permeate enriched in the first component and a retentate depleted in the first component,
wherein performing the membrane separation comprises exposing the feed stream to a membrane structure comprising a first membrane layer and a second membrane layer under at least one of reverse osmosis conditions or forward osmosis conditions, the reverse osmosis conditions or forward osmosis conditions comprising a feed pressure of at least 0.2 MPag, the first component being in the liquid phase in the feed and in the permeate for at least one position along the length of the membrane, the first membrane layer having a pore volume of at least 0.2 cm$^3$/g of pores with a median pore size of at least 20 nm, the second membrane layer comprising a porous carbon layer having a BET surface area of at least about 100 m$^2$/g and having a pore size distribution comprising a smallest substantial pore size peak having a median pore size of about 3.0 Angstroms to about 50 Angstroms.

2. The method of claim 1, wherein the first membrane layer comprises a porous carbon layer, or wherein the first membrane layer comprises a porous metal structure.

3. The method of claim 1, wherein the first component comprises sulfuric acid and the second component comprises acid soluble oils, and wherein the smallest substantial pore size peak has a median pore size of about 5.0 Angstroms to about 10 Angstroms.

4. The method of claim 1, wherein the smallest substantial pore size peak has a median pore size of about 5.8 Angstroms to about 6.8 Angstroms.

5. The method of claim 1, wherein the second component comprises a homogeneous catalyst, and wherein the wherein the smallest substantial pore size peak has a median pore size of about 4.0 Angstroms to about 7.0 Angstroms.

6. The method of claim 1, wherein the smallest substantial pore size peak has a median pore size of about 4.5 Angstroms to about 6.1 Angstroms, and a) wherein the first component comprises ethanol, or b) wherein the first component comprises isobutane, or wherein the second component comprises 2,2,4 trimethyl pentane, or a combination thereof.

7. The method of claim 1, wherein the second component comprises methylmethacrylate, methacrylic acid, or a combination thereof, or wherein the second component comprises a sugar.

8. The method of claim 1, wherein the smallest substantial pore size peak has a median pore size of about 3.0 Angstroms to about 6.0 Angstroms, and wherein a) the first component is water and the second component is isopropyl alcohol, or b) wherein the first component comprises a $C_4$-$C_8$ paraffin and the second component comprises a $C_{io}$-$C_{20}$ paraffin.

9. The method of claim 1, wherein the smallest substantial pore size peak has a median pore size of about 3.2 Angstroms to about 4.2 Angstroms, and wherein the first component comprises at least one of ethylene, propylene, and n-butylene, and the second component comprises at least one of ethane, propane, and n-butane.

10. The method of claim 1, wherein the first component and the second component comprise hydrocarbonaceous compounds, or wherein the first component and the second component comprise hydrocarbon isomers.

11. The method of claim 1, wherein the substantial pore size peak corresponding to the smallest median pore size has a median pore size when the membrane structure is exposed to a liquid for separation that differs by 10% or less from the median pore size when the membrane structure is not exposed to the liquid for separation.

12. A method for separating a feed stream, comprising:
performing a membrane separation on a feed stream comprising a first component and a second component, the first component and the second component comprising a hydrocarbon, a hydrocarbonaceous compound, or a combination thereof, the feed stream comprising 5 wt % to 95 wt % of the first component, to form a permeate enriched in the first component and a retentate depleted in the first component,
wherein performing the membrane separation comprises exposing the feed stream to a membrane structure comprising a first membrane layer and a second membrane layer under at least one of reverse osmosis and forward osmosis conditions, the reverse osmosis conditions or forward osmosis conditions comprising a feed pressure of at least 0.2 MPag, the first component being in the liquid phase in the feed and in the permeate for at least one position along the length of the membrane, the first membrane layer having a pore volume of at least 0.2 cm$^3$/g of pores with a median pore size of at least 20 nm, the first membrane layer comprising a porous carbon layer or comprising a porous metal structure, the second membrane layer of the membrane structure comprising a porous carbon layer having a BET surface area of at least about 300 m$^2$/g, the second membrane layer having a pore size distribution comprising a smallest substantial pore size peak having a median pore size of about 5.8 Angstroms to about 6.8 Angstroms.

13. The method of claim 12, wherein the hydrocarbonaceous stream comprises $C_{8+}$ aromatics, the hydrocarbonaceous stream comprising 5 wt % to 95 wt % p-xylene, the first component being p-xylene and the second component being at least one of m-xylene and o-xylene.

14. The method of claim 12, wherein a size difference between the first component and the second component is about 2.0 Angstroms or less; or wherein a peak width of the smallest substantial pore size peak at half of the peak height is about 75% or less of the size difference between the first component and the second component; or a combination thereof.

15. A method for separating a feed stream, comprising:
performing a membrane separation on a feed stream comprising a first component and a second component, the first component and the second component comprising a hydrocarbon, a hydrocarbonaceous compound, or a combination thereof, the feed stream comprising 5 wt % to 95 wt % of the first component, to form a permeate enriched in the first component and a retentate depleted in the first component,
wherein performing the membrane separation comprises exposing the feed stream to a membrane structure comprising a first membrane layer and a second membrane layer under at least one of reverse osmosis and forward osmosis conditions, the reverse osmosis conditions or forward osmosis conditions comprising a feed pressure of at least 0.2 MPag, the first component being in the liquid phase in the feed and in the permeate for at least one position along the length of the membrane, the first membrane layer having a pore volume of at least 0.2 cm$^3$/g of pores with a median pore size of at least 20 nm, the first membrane layer comprising a porous carbon layer or comprising a porous metal structure, the second membrane layer of the membrane structure comprising a porous carbon layer having a BET surface area of at least about 300 m$^2$/g, the second membrane layer having a pore size distribution comprising a smallest substantial pore size peak having a median pore size of about 3.0 Angstroms to about 10 Angstroms.

* * * * *